US011123102B2

(12) United States Patent
Dang et al.

(10) Patent No.: US 11,123,102 B2
(45) Date of Patent: *Sep. 21, 2021

(54) NATURAL ORIFICE SURGERY SYSTEM

(71) Applicant: Applied Medical Resources Corporation, Rancho Santa Margarita, CA (US)

(72) Inventors: Kevin K. Dang, Garden Grove, CA (US); Jeremy J. Albrecht, Rancho Santa Margarita, CA (US); Blaze Brown, Rancho Santa Margarita, CA (US); Adam Hoke, Shelbyville, MI (US); Adeeb Saiduddin, Irvine, CA (US); Gary M. Johnson, Rancho Santa Margarita, CA (US); Jacob J. Filek, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 16/374,526

(22) Filed: Apr. 3, 2019

(65) Prior Publication Data

US 2019/0223906 A1  Jul. 25, 2019

Related U.S. Application Data

(63) Continuation of application No. 15/845,002, filed on Dec. 18, 2017, now Pat. No. 10,271,875, which is a (Continued)

(51) Int. Cl.
*A61B 17/34* (2006.01)
*A61B 1/32* (2006.01)
(Continued)

(52) U.S. Cl.
CPC ............ *A61B 17/3423* (2013.01); *A61B 1/32* (2013.01); *A61B 17/0218* (2013.01);
(Continued)

(58) Field of Classification Search
CPC . A61B 17/02; A61B 17/0293; A61B 17/0218; A61B 17/34; A61B 17/3431
See application file for complete search history.

(56) References Cited

U.S. PATENT DOCUMENTS

| 558,364 A | 4/1896 | Doolittle |
|---|---|---|
| 1,157,202 A | 10/1915 | Bates et al. |

(Continued)

FOREIGN PATENT DOCUMENTS

| DE | 26 05 148 A1 | 8/1977 |
|---|---|---|
| DE | 33 36 279 C2 | 1/1986 |

(Continued)

OTHER PUBLICATIONS

U.S. Appl. No. 10/381,220, filed Mar. 20, 2003; Title: Surgical Access Apparatus and Method, now U.S. Pat. No. 7,473,221 issued Jan. 6, 2009.

(Continued)

*Primary Examiner* — Christopher J Beccia
(74) *Attorney, Agent, or Firm* — Thomas Nguyen; Patrick Ikehara

(57) ABSTRACT

Embodiments of a surgical access port system that comprises a retractor that is adapted for being coupled to a cap and that is particularly useful in natural orifice surgery are described. The retractor comprises an outer ring, wherein the outer ring is configured to be disposed proximate the natural orifice of the patient and substantially surround the orifice; a tubular body; a funnel segment extending between and coupling the outer ring and the tubular body, wherein the funnel segment provides a diametric reduction between the (Continued)

relatively large diameter of the outer ring and the relatively smaller diameter of the tubular body, which is sized to fit within a natural orifice with minimal distention of the orifice; and an inflatable member disposed around the distal end of the tubular body, the inflatable member sized and configured to fit snugly around the tubular body in the deflated condition and to expand against the wall of the natural orifice in the inflated state to thereby stabilize and retain the retractor within the orifice.

13 Claims, 46 Drawing Sheets

Related U.S. Application Data continuation of application No. 15/016,080, filed on Feb. 4, 2016, now Pat. No. 9,872,702, which is a continuation of application No. 13/865,854, filed on Apr. 18, 2013, now Pat. No. 9,289,115, and a continuation-in-part of application No. 13/250,398, filed on Sep. 30, 2011, now Pat. No. 9,289,200.

(60) Provisional application No. 61/636,492, filed on Apr. 20, 2012, provisional application No. 61/389,091, filed on Oct. 1, 2010, provisional application No. 61/485,321, filed on May 12, 2011.

(51) Int. Cl.
*A61B 17/02* (2006.01)
*A61B 17/00* (2006.01)

(52) U.S. Cl.
CPC ...... *A61B 17/0293* (2013.01); *A61B 17/3421* (2013.01); *A61B 17/3431* (2013.01); *A61B 2017/00557* (2013.01); *A61B 2017/00889* (2013.01); *A61B 2017/00907* (2013.01); *A61B 2017/0225* (2013.01); *A61B 2017/345* (2013.01); *A61B 2017/347* (2013.01); *A61B 2017/3419* (2013.01); *A61B 2017/3429* (2013.01); *A61B 2017/3443* (2013.01); *A61B 2017/3445* (2013.01); *A61B 2017/3452* (2013.01); *A61B 2017/3466* (2013.01); *A61B 2017/3482* (2013.01); *A61B 2017/3486* (2013.01); *A61B 2017/3492* (2013.01)

(56) References Cited

U.S. PATENT DOCUMENTS

| | | |
|---|---|---|
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,729,027 A | 4/1973 | Bare |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,083,370 A | 4/1978 | Taylor |
| 4,096,853 A | 6/1978 | Weigand |
| 4,112,932 A | 9/1978 | Chiulli |
| 4,117,847 A | 10/1978 | Clayton |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |

(56) References Cited

U.S. PATENT DOCUMENTS

| | | |
|---|---|---|
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III et al. |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Soya et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |

(56) References Cited

U.S. PATENT DOCUMENTS

| | | |
|---|---|---|
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Durdal et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Strouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchliffe et al. |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |

(56) References Cited

U.S. PATENT DOCUMENTS

| | | |
|---|---|---|
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,816 A | 5/2000 | Moenning |
| 6,066,117 A | 5/2000 | Fox et al. |
| 6,068,639 A | 5/2000 | Fogarty et al. |
| 6,076,560 A | 6/2000 | Stahle et al. |
| 6,077,288 A | 6/2000 | Shimomura |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B2 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |

(56) References Cited

U.S. PATENT DOCUMENTS

| | | |
|---|---|---|
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Liu et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 | 11/2010 | Keller |
| 7,850,667 B2 | 12/2010 | Gresham |
| 7,867,164 B2 | 1/2011 | Butler et al. |
| 7,878,974 B2 | 2/2011 | Brustad et al. |
| 7,896,889 B2 | 3/2011 | Mazzocchi et al. |
| 7,909,760 B2 | 3/2011 | Albrecht et al. |
| 7,930,782 B2 | 4/2011 | Chen |
| 8,328,717 B2 * | 12/2012 | Battles ............... A61B 17/3462 600/206 |
| 9,289,200 B2 * | 3/2016 | Dang ................. A61B 17/0218 |
| 9,872,702 B2 * | 1/2018 | Dang ................. A61B 17/0218 |
| 10,271,875 B2 * | 4/2019 | Dang ................. A61B 17/3431 |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlbert et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkier, II et al. |
| 2005/0090713 A1 | 4/2005 | Gozales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |

(56) References Cited

U.S. PATENT DOCUMENTS

| | | |
|---|---|---|
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0088204 A1 | 4/2007 | Albrecht |
| 2007/0093695 A1 | 4/2007 | Bonadio et al. |
| 2007/0118175 A1 | 5/2007 | Butler et al. |
| 2007/0149859 A1 | 6/2007 | Albrecht |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270752 A1 | 11/2007 | Labombard |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0182282 A1 | 7/2009 | Okihisa |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegel et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2010/0312063 A1* | 12/2010 | Hess ............... A61B 17/3423 600/204 |
| 2010/0312066 A1* | 12/2010 | Cropper ........... A61B 17/3423 600/207 |
| 2011/0021877 A1 | 1/2011 | Fortier et al. |
| 2011/0028891 A1 | 2/2011 | Okoniewski |
| 2011/0034935 A1* | 2/2011 | Kleyman ......... A61B 17/3423 606/108 |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |
| 2012/0095297 A1 | 4/2012 | Dang et al. |

FOREIGN PATENT DOCUMENTS

| | | |
|---|---|---|
| DE | 37 39 532 | 12/1988 |
| DE | 37 37 121 | 5/1989 |
| DE | 296 00 939 | 6/1996 |
| DE | 19828009 | 12/1999 |
| EP | 0 113 520 | 7/1984 |
| EP | 0 142 262 | 5/1985 |
| EP | 0 517 248 | 12/1992 |
| EP | 0 537 768 | 4/1993 |
| EP | 0 807 416 | 11/1997 |
| EP | 0 849 517 | 6/1998 |
| EP | 0950376 | 10/1999 |
| EP | 1 118 657 | 7/2001 |
| EP | 1 125 552 | 8/2001 |
| EP | 1 312 318 | 5/2003 |
| EP | 1 407 715 | 4/2004 |
| EP | 2 044 889 | 4/2009 |
| EP | 2 272 450 A2 | 1/2011 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |

(56) References Cited

FOREIGN PATENT DOCUMENTS

| | | |
|---|---|---|
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/045568 | 6/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2007/044849 | 4/2007 |
| WO | WO 2008/015566 | 2/2008 |
| WO | WO 2008/093313 | 8/2008 |
| WO | WO 2008/121294 | 10/2008 |
| WO | WO 2010/045253 | 4/2010 |
| WO | WO 2010/082722 | 7/2010 |
| WO | WO 2010/104259 | 9/2010 |

OTHER PUBLICATIONS

U.S. Appl. No. 10/436,522, filed May 13, 2003; Title: Laparoscopic Illumination Apparatus and Method, now U.S. Pat. No. 6,939,296 issued Sep. 6, 2005.

U.S. Appl. No. 10/399,209, filed Aug. 22, 2003; Title: Wound Retraction Apparatus and Method, now U.S. Pat. No. 6,958,037 issued Oct. 25, 2005.

U.S. Appl. No. 11/218,412, filed Sep. 1, 2005; Title: Wound Retraction Apparatus and Method, now U.S. Pat. No. 7,238,154 issued Jul. 3, 2007.

U.S. Appl. No. 10/399,057, filed Apr. 11, 2003; Title: Sealed Surgical Access Device, now U.S. Pat. No. 7,052,454 issued May 30, 2006.

U.S. Appl. No. 10/666,579, filed Sep. 17, 2003; Title: Surgical Instrument Access Device, now U.S. Pat. No. 7,163,510 issued Jan. 16, 2007.

U.S. Appl. No. 10/052,297, filed Jan. 18, 2002; Title: Hand Access Port Device, now U.S. Pat. No. 6,908,430 issued Jun. 21, 2005.

U.S. Appl. No. 08/015,765, filed Feb. 10, 1993; Title: Gas-Tight Seal Accomodating Surgical Instruments With a Wide Range of Diameters, now U.S. Pat. No. 5,407,433 issued Apr. 18, 1995.

U.S. Appl. No. 08/040,373, filed Mar. 30, 1993; Title: Gas-Tight Seal Accomodating Surgical Instruments With a Wide Range of Diameters, now U.S. Pat. No. 5,411,483 issued May 2, 1995.

U.S. Appl. No. 10/902,756, filed Jul. 29, 2004; Title: Hand Access Port Device, now abandoned.

U.S. Appl. No. 10/802,125, filed Mar. 15, 2004; Title: Surgical Guide Valve, now abandoned.

U.S. Appl. No. 10/516,198, filed Nov. 30, 2004; Title: Wound Retractor, now U.S. Pat. No. 7,650,887 issued Jan. 26, 2010.

U.S. Appl. No. 10/927,551, filed Aug. 25, 2004; Title: Surgical Access System, now abandoned.

U.S. Appl. No. 11/244,647, filed Oct. 5, 2005; Title: Surgical Access Apparatus and Method, now U.S. Pat. No. 7,481,765 issued Jan. 27, 2009.

U.S. Appl. No. 11/548,746, filed Oct. 12, 2006; Title: Method of Making a Hand Access Laparoscopic Device, now U.S. Pat. No. 7,749,415 issued Jul. 6, 2010.

U.S. Appl. No. 11/548,765, filed Oct. 12, 2006; Title: Split Hoop Wound Retractor, now U.S. Pat. No. 7,815,567 issued Oct. 26, 2010.

U.S. Appl. No. 11/548,767, filed Oct. 12, 2006; Title: Circular Surgical Retractor now U.S. Pat. No. 7,704,207 issued Apr. 27, 2010.

U.S. Appl. No. 11/548,781, filed Oct. 12, 2006; Title: Wound Retractor With Gel Cap, now U.S. Pat. No. 7,727,146 issued Jun. 1, 2010.

U.S. Appl. No. 11/548,955, filed Oct. 12, 2006; Title: Hand Access Laparoscopic Device, now U.S. Pat. No. 7,736,306 issued Jun. 15, 2010.

U.S. Appl. No. 11/755,305, filed May 30, 2007; Title: Wound Retraction Apparatus and Method, now U.S. Pat. No. 7,377,898 issued May 27, 2008.

U.S. Appl. No. 11/548,758, filed Oct. 12, 2007; Title: Split Hoop Wound Retractor With Gel Pad, now U.S. Pat. No. 7,909,760 issued Mar. 22, 2011.

U.S. Appl. No. 12/693,242, filed Jan. 1, 2010; Title: Wound Retractor, now U.S. Pat. No. 7,913,697 issued Mar. 29, 2011.

U.S. Appl. No. 12/768,328, filed Apr. 27, 2010; Title: Circular Surgical Retractor, now U.S. Pat. No. 7,892,172 issued Feb. 22, 2011.

U.S. Appl. No. 12/791,666, filed Jun. 1, 2010; Title: Wound Retractor With Gel Cap, now U.S. Pat. No. 7,883,461 issued Feb. 8, 2011.

U.S. Appl. No. 12/815,986, filed Jun. 15, 2010; Title: Hand Access Laparoscopic Device, now U.S. Pat. No. 7,878,974 issued Feb. 1, 2011.

(56) References Cited

OTHER PUBLICATIONS

U.S. Appl. No. 10/695,295, filed Oct. 28, 2003; Title: Surgical Gel Seal.
U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011; Title: Hand Access Laparoscopic Device.
U.S. Appl. No. 13/008,728, filed Jan. 18, 2011; Title: Wound Retractor With Gel Cap.
U.S. Appl. No. 13/023,334, filed Feb. 8, 2011; Title: Circular Surgical Retractor.
U.S. Appl. No. 13/031,892, filed Feb. 22, 2011; Title: Wound Retractor.
U.S. Appl. No. 13/050,042, filed Mar. 17, 2011; Title: Split Hoop Wound Retractor With Gel Pad.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc., dated 1999.
European Patent Office, European Search Report for European Application No. EP 10 18 4681, entitled "Wound Retraction Apparatus and Method", dated Nov. 22, 2010.
European Patent Office, European Search Report for European Application No. EP 10 18 4608, entitled "Wound Retraction Apparatus and Method", dated Nov. 22, 2010.
European Patent Office, European Search Report for European Application No. EP 10 18 4648, entitled "Wound Retraction Apparatus and Method", dated Nov. 22, 2010.
European Patent Office, European Search Report for European Application No. EP 10 18 4731, entitled "Wound Retraction Apparatus and Method", dated Nov. 22, 2010.
European Patent Office, European Search Report for European Application No. EP 10 18 4661, entitled "Wound Retraction Apparatus and Method", dated Nov. 22, 2010.
European Patent Office, European Search Report for European Application No. EP 10 18 4677, entitled "Wound Retraction Apparatus and Method", dated Nov. 22, 2010.
European Patent Office, European Search Report for European Application No. EP 10 18 9325, entitled "Split Hoop Wound Retractor", dated Dec. 14, 2010.
European Patent Office, European Search Report for European Application No. EP 10 18 9327, entitled "Split Hoop Wound Retractor", dated Dec. 14, 2010.
European Patent Office, European Search Report for European Application No. EP 10 18 9328, entitled "Split Hoop Wound Retractor", dated Dec. 15, 2010.
European Patent Office, European Search Report for European Application No. EP 04 00 2888, entitled "Hand Access Port Device", dated Sep. 10, 2004.
European Patent Office, European Search Report for European Application No. EP 04 00 2889, entitled "Hand Access Port Device", dated Sep. 13, 2004.
European Patent Office, International Search Report and the Written Opinion of the International Searching Authority for International Application No. PCT/US2006/040154, dated Jan. 30, 2007.
European Patent Office, International Search Report and the Written Opinion of the International Searching Authority for International Application No. PCT/US2006/040073, dated Jan. 26, 2007.
European Patent Office, International Search Report and the Written Opinion of the International Searching Authority for International Application No. PCT/US2006/039905, dated Jan. 17, 2007.
European Patent Office, International Search Report and the Written Opinion of the International Searching Authority for International Application No. PCT/US2006/039883, dated Jan. 31, 2007.
European Patent Office, International Search Report and the Written Opinion of the International Searching Authority for International Application No. PCT/US2006/039800, dated Apr. 16, 2007.
European Patent Office, International Search Report and the Written Opinion of the International Searching Authority for International Application No. PCT/US2006/039799, dated Mar. 27, 2007.
European Patent Office, European Search Report for European Application No. EP 08253236 dated Feb. 10, 2009.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484, dated Nov. 12, 2004.
International Searching Authority/US, International Search Report and the Written Opinion of the International Searching Authority for International Application No. PCT/US01/29682, dated Jun. 14, 2002.

(56) References Cited

OTHER PUBLICATIONS

McSweeney, Cannulation of the Rumen in Cattle and Buffaloes, Australian Veterniary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan, dated 1992.
The International Bureau of WIPO, International Preliminary Report on Patentability for International Application No. PCT/US2004/028250, dated Aug. 29, 2006.
The International Bureau of WIPO, International Preliminary Report on Patentability for International Application No. PCT/US2006/039799, dated Apr. 16, 2008.
The International Bureau of WIPO, International Preliminary Report on Patentability for International Application No. PCT/US2006/039800 dated Apr. 16, 2008.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, Laparascopic cholecystecomy via two ports, using the "Twin-Port" system, J. Hepatobiliary Pancreat Surg (2001) 8:76-80, dated Feb. 20, 2001.
Declaration of John R. Brustad dated Dec. 10, 2009, submitted in U.S. Appl. No. 11/548,955, including Appendices A-D regarding product sales brochures and production drawings from 2001 and 2005.
International Search Report and Written Opinion for PCT/IE2005/000113, dated Feb. 22, 2006.
International Searching Authority-US, International Search Report and Written Opinion of the International Searching Authority for International Application No. PCT/US04/25511, dated Nov. 7, 2007.
International Bureau of WIPO, International Report on Patentability for International Application No. PCT/US04/25511, dated Dec. 6, 2007.
International Search Report and Written Opinion for PCT/IE2007/000050 dated Aug. 13, 2007.
The International Searching Authority, The International Search Report and Written Opinion of the International Searching Authority for International Application No. PCT/US08/63445, dated Sep. 29, 2008.
The International Searching Authority, The International Search Report and Written Opinion of the International Searching Authority for International Application No. PCT/US08/063463 dated Sep. 10, 2008.
The International Bureau of WIPO, International Preliminary Report on Patentability for International Application No. PCT/US2008/063463, entitled "Surgical Retractor", dated Nov. 17, 2009.
The International Bureau of WIPO, International Preliminary Report on Patentability for International Application No. PCT/US08/63445, entitled "Surgical Retractor with Gel Pad", dated Nov. 17, 2009.
International Searching Authority—European Patent Office, The International Search Report and Written Opinion for International Application No. PCT/US2011/054266, dated Feb. 9, 2012.
European Patent Office, European Search Report for European Patent No. 11172709.5, dated Aug. 16, 2011.
European Patent Office, European Search Report for European Patent No. 11172706.1, dated Aug. 16, 2011.
European Patent Office, European Search Report for European Patent No. 12151288, dated Feb. 10, 2012.
European Patent Office, European Search Report for European Patent No. 08755332, dated Apr. 18, 2012.
European Patent Office, Supplementary European Search Report for European Patent Application No. 08755322, dated Apr. 18, 2012.
European Patent Office, Supplementary European Search Report for European Patent Application No. 08755336, dated Jun. 15, 2012.
Harold W. Harrower, M.D., Isolation of Incisions into Body Cavities, The American Journal of Surgery, vol. 116, pp. 824-826, Dec. 1968.
International Searching Authority—European Patent Office, The International Search Report and Written Opinion for International Application No. PCT/US2012/60997, dated Mar. 7, 2013.
The International Bureau of WIPO, International Preliminary Report on Patentability for International Application No. PCT/US2011/054266, titled "Natural Orifice Surgery System", dated Apr. 2, 2013.
European Patent Office, The International Search Report and Written Opinion for International Application No. PCT/US2013/037213, titled "Natural Orifice Surgery System" dated Jul. 3, 2013.
The International Bureau of WIPO, International Preliminary Report on Patentability for Application No. PCT/US2013/037213, titled "Natural Orifice Surgery System", dated Oct. 21, 2014.

\* cited by examiner

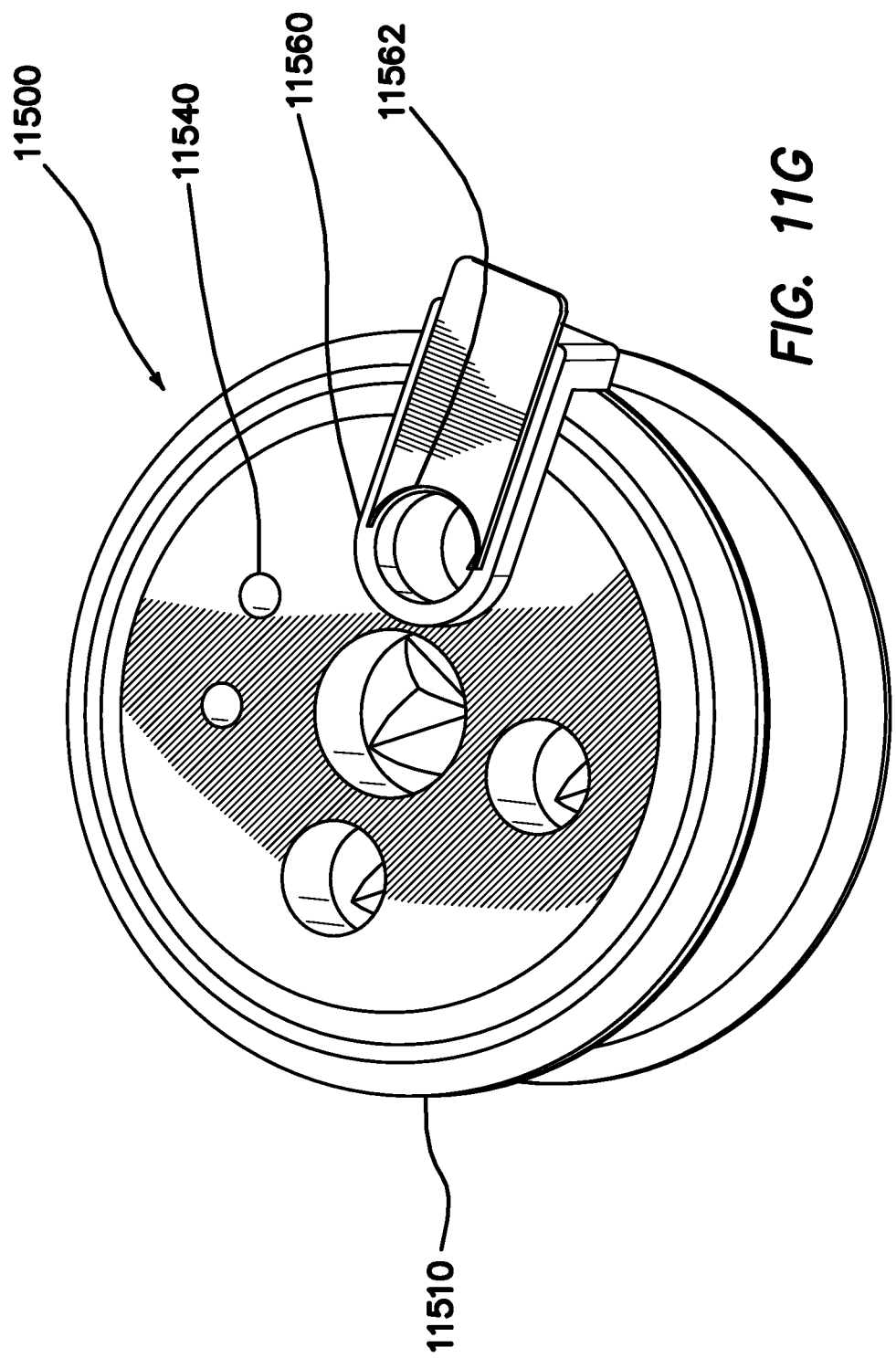

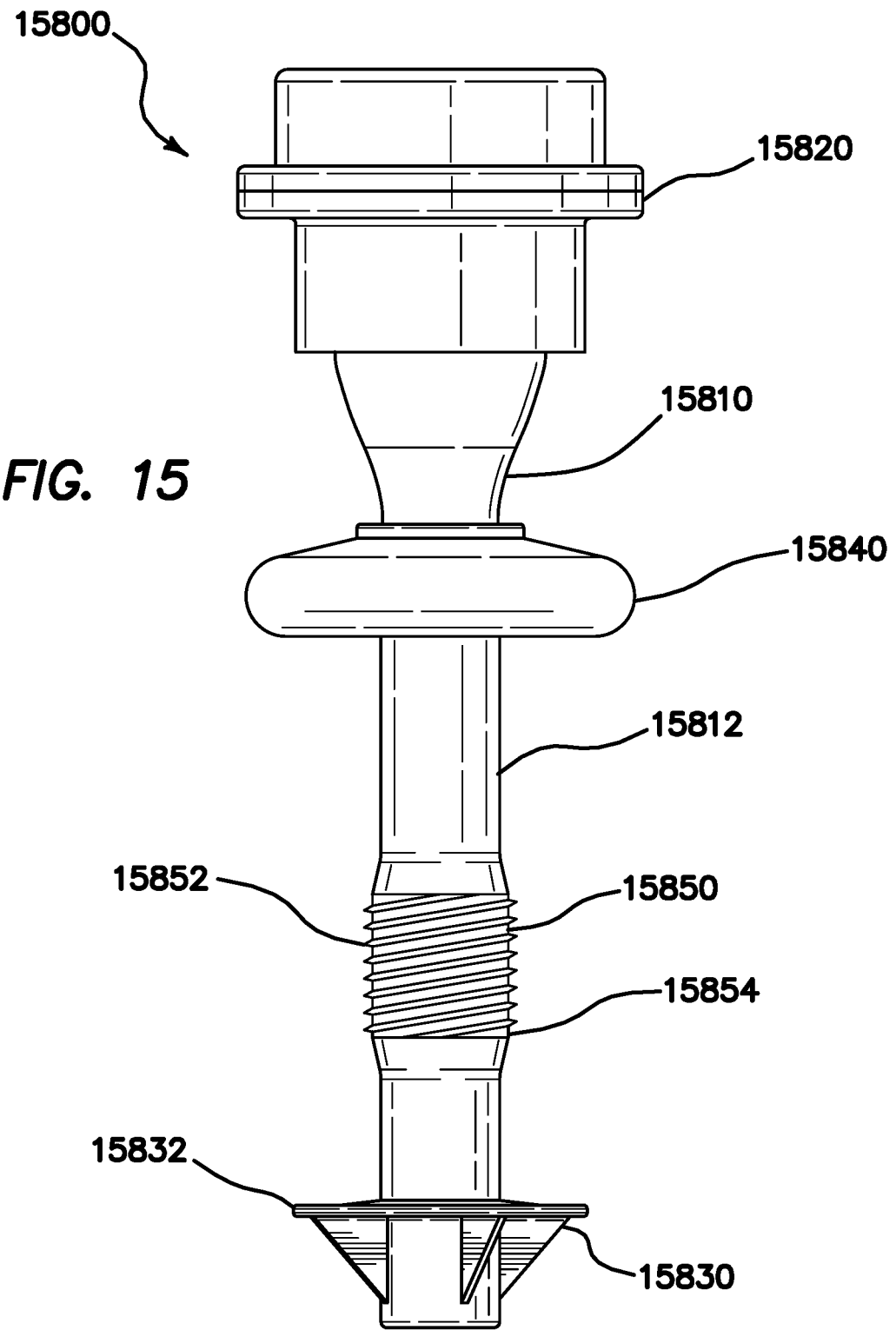

NATURAL ORIFICE SURGERY SYSTEM

CROSS REFERENCE TO RELATED APPLICATIONS

This application is a continuation of U.S. application Ser. No. 15/845,002, entitled "NATURAL ORIFICE SURGERY SYSTEM," filed Dec. 18, 2017, which claims the benefit of continuation of U.S. application Ser. No. 15/016,080, entitled "NATURAL ORIFICE SURGERY SYSTEM," filed Feb. 4, 2016, which claims the benefit of continuation of U.S. application Ser. No. 13/865,854, entitled "NATURAL ORIFICE MICROSURGERY SYSTEM," filed Apr. 18, 2013, which claims the benefit of U.S. Provisional Application Ser. No. 61/636,492, entitled "NATURAL ORIFICE MICROSURGERY SYSTEM," filed Apr. 20, 2012 and which is a continuation-in-part of U.S. application Ser. No. 13/250,398, entitled "NATURAL ORIFICE MICROSURGERY SYSTEM," filed Sep. 30, 2011, which claims the benefit of U.S. Provisional Application Ser. No. 61/389,091 entitled "TRANSANAL ENDOSCOPIC MICROSURGERY SYSTEM," filed Oct. 1, 2010 and U.S. Provisional Application Ser. No. 61/485,321, entitled "TRANSANAL ENDOSCOPIC MICROSURGERY SYSTEM," filed May 12, 2011. The above-referenced applications are hereby incorporated by reference herein in their entirety.

BACKGROUND

Technical Field

This application is generally directed to surgical devices, and more particularly, to a retractor adapted for use with a cap, that is useful in natural orifice single-port surgical procedures.

Description of the Related Art

Access devices are commonly used in surgery to facilitate the introduction of various surgical instruments into natural biological vessels, conduits, orifices, cavities, and other interior regions of the body. These access devices include, for example, devices that facilitate the introduction of a needle into a vessel, and trocars that facilitate the introduction of laparoscopic instruments into the abdomen of the body.

Some of these access devices are introduced into regions that include a fluid or gas under pressure. In the case of a needle access device, the pressure may be from a liquid, such as blood. In the case of a trocar, the pressure may be from a gas, such as an insufflation gas. In either case, it is desirable to provide for the introduction of the surgical instrument into the cavity without permitting the escape of the pressurized fluid or gas.

In the case of trocars, a cannula at the distal end of the trocar is typically connected to a seal housing at the proximal end of the trocar. Together the cannula and housing form a working channel through which various instruments can be inserted to access the cavity. Seal mechanisms are commonly disposed in the housing and include a septum valve that seals the working channel when an instrument is in place, and a zero closure valve that seals the working channel when the instrument is removed.

Current surgical access ports allow for single instrument access through each port, or allow for multiple instrument access through a rigid cannula. Some devices, such as transanal endoscopic microsurgery (TEMS) units require that the device be attached to the surgical table to support the weight of the device, as well as to locate the position of the device respective to the patient. These devices do not provide flexibility to the surgeon in selecting instrument size, and they restrict instrument movement with their rigid cannulas. Additionally, surgeons are performing laparoscopic surgical procedures through a single or a limited number of access ports. The procedures may be performed through a single two (2) centimeter incision at the umbilicus, or in certain cases, trans-vaginally or trans-anally. What is needed is a system that meets the needs of these new procedures, facilitating more flexible movement of laparoscopic instruments through a single or limited number of ports while preventing the escape of pressured fluids or gasses and permitting large specimen removal.

SUMMARY OF THE INVENTION

The invention is directed to a surgical access port system that comprises a retractor that is adapted for being coupled to a cap and that is particularly useful in natural orifice surgery. The retractor comprises an outer ring, wherein the outer ring is configured to be disposed proximate the natural orifice of the patient and substantially surround the orifice; a tubular body; a funnel segment extending between and coupling the outer ring and the tubular body, wherein the funnel segment provides a diametric reduction between the relatively large diameter of the outer ring and the relatively smaller diameter of the tubular body, which is sized to fit within a natural orifice with minimal distention of the orifice; and an inflatable member disposed around the distal end of the tubular body, the inflatable member sized and configured to fit snugly around the tubular body in the deflated condition and to expand against the wall of the natural orifice in the inflated state to thereby stabilize and retain the retractor within the orifice.

In one aspect, the tubular body comprises a substantially flexible material, such as a KRATON® material, a PELLETHANE® material or a silicone rubber material. In another aspect, the tubular body comprises a more rigid material, such as polycarbonate. The tubular body defines a generally cylindrical passage large enough to accommodate at least one laparoscopic instrument there through, and preferably is sufficiently large such that two or more surgical instruments positioned there through can be translated or pivoted relative to one another. In one aspect, the tubular body comprises one or more coatings, such as an antimicrobial coating. In one aspect, the tubular body has an adjustable length, where, for example, it comprises interlocking sections or perforations. In another aspect, the tubular body has opening or windows along the length of the body, to provide access by surgical instruments to the body cavity or orifice.

In one aspect, the funnel segment comprises an inner surface that can provide a bearing surface for an obturator used to advance to the retractor into a body cavity. The funnel segment can have a substantially linear taper between the relatively large diameter of the outer ring and the relatively smaller diameter of the tubular body. In one aspect, the funnel segment has a curved profile between the relatively large diameter and the relatively smaller diameter.

In one aspect, the tubular body can be formed from a relatively flexible material and the funnel segment and the outer ring from a relatively rigid material. The surgical access port system can further comprise an obturator.

In one aspect, the surgical access port system further comprises a removable cap, wherein the cap is adapted to sealingly engage the outer ring. In one aspect, the cap has a sealable access surface, such as a gel pad, and can include at least one fluid or gas port. In one aspect, the surgical access port system further comprises at least one trocar access device, wherein the trocar access device is adapted to be positioned through the sealable access surface. The trocar access device preferably contains at least one sealing valve, such as a septum seal or duck bill valve. In one aspect, the trocar access device has a low profile.

These and other features and advantages of the invention will become more apparent with a discussion of embodiments in reference to the associated drawings.

BRIEF DESCRIPTION OF THE DRAWINGS

FIG. 9A is a perspective view of an embodiment of a natural orifice access device including a cap having a plurality of trocars extending there through. FIG. 9B is a perspective view of another embodiment of a natural orifice access device including a cap having a plurality of trocars extending there through.

FIG. 11G is a top perspective view of an embodiment of gel cap comprising a fixed camera or laparoscope port.

FIG. 15 is a side view of another embodiment of a trocar comprising a fixation cannula.

Similar components have similar reference numbers throughout.

DETAILED DESCRIPTION OF CERTAIN EMBODIMENTS

Figure 1:
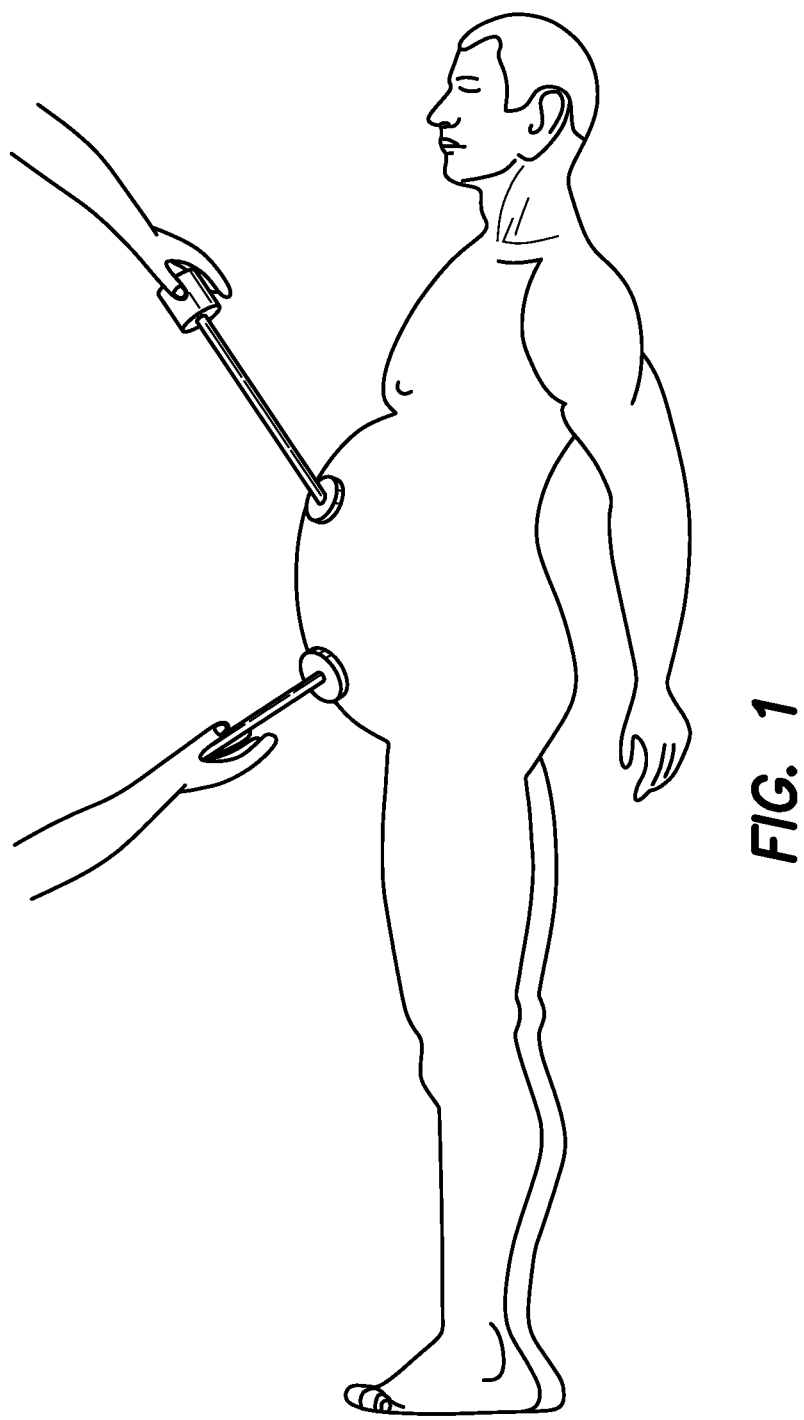
FIG. 1 is a side view of a patient in surgery illustrating an embodiment of the access device positioned on the abdomen and in use.
Figure 2:
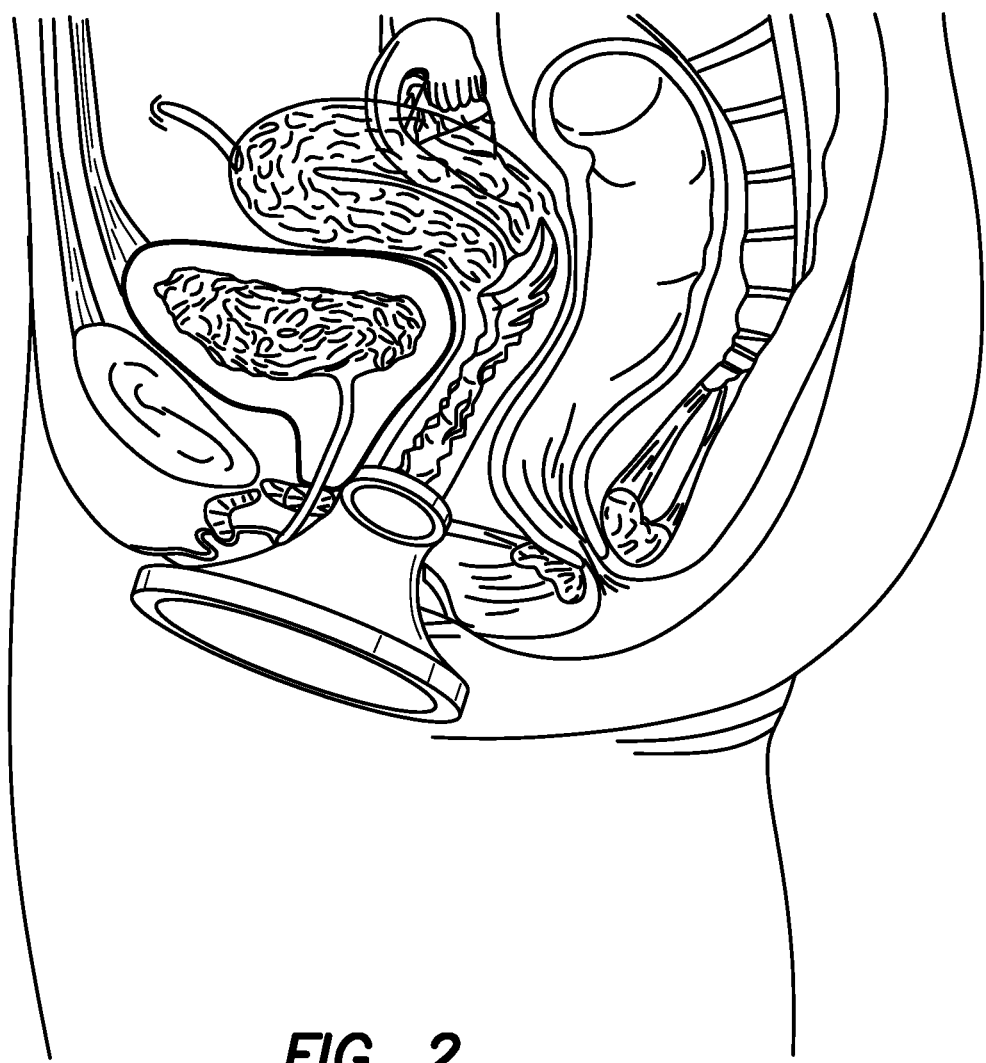
FIG. 2 is a cross-sectional side view illustrating an embodiment of the access device, with the wound retractor retracting the vagina of a patient, and the gel cap sealing the opening of the wound retractor.
Figure 3:
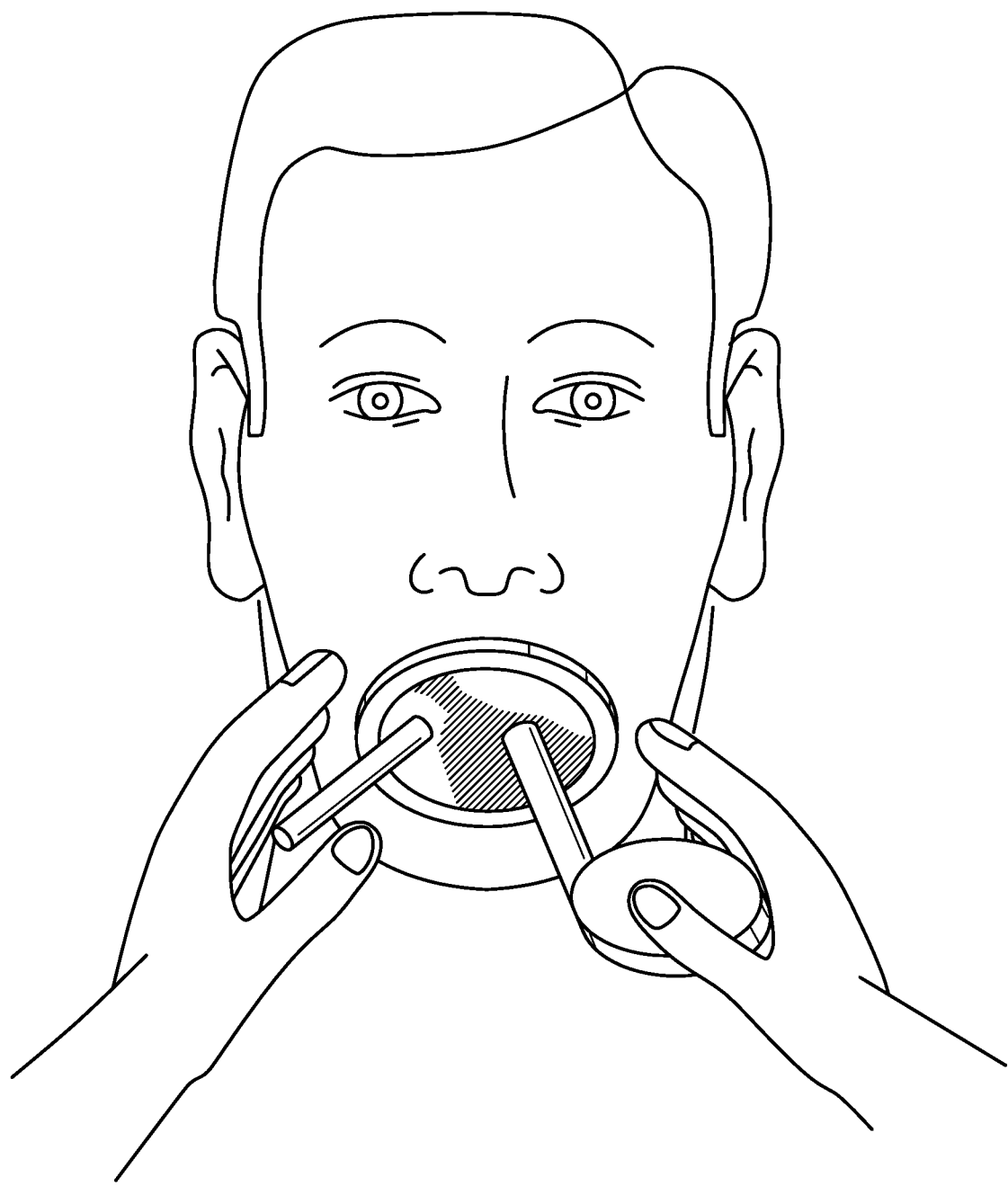
FIG. 3 is a front view illustrating an embodiment of the access device deployed and in use at the mouth of the patient.

Embodiments of a surgical instrument access device system are useful, for example, for single incision, single port, and/or limited port laparoscopic surgical procedures, for example, abdominal (FIG. 1), transvaginal (FIG. 2), transoral (FIG. 3), and transanal (FIG. 4) procedures. Various surgical instrument access devices are described in U.S. Patent Application Publication No. 2009/0187079, entitled "SURGICAL INSTRUMENT ACCESS DEVICE," filed Jan. 22, 2009, and U.S. Pat. No. 7,727,146, entitled "WOUND RETRACTOR WITH GEL CAP," both of which are incorporated by reference in their entireties herein.

Figure 5:
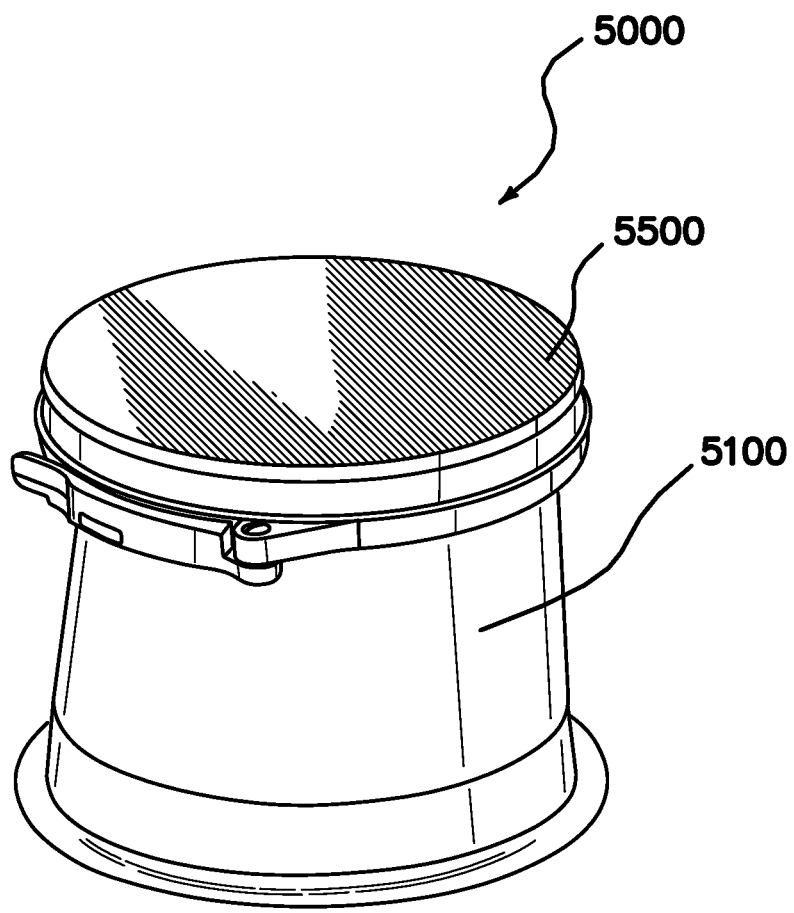
FIG. 5 is a perspective view of an embodiment of an access device comprising a cap and a retractor.

FIG. 5 illustrates a perspective view of an embodiment of an access device system 5000 comprising a retractor 5100 and a cap 5500, which is useful in single port and/or limited port procedures. The retractor or surgical wound retractor 5100 is placed and/or positioned into, across, and/or through a surgical incision and/or body orifice to enlarge, reshape, and/or isolate the incision or body orifice. The cap 5500 provides an artificial body wall through which instruments access the interior of a patient's body, for example, a body cavity. The components of the access device 5000 comprise any suitable biologically compatible materials.

Two embodiments of natural orifice access ports or retractors 6100, 7100 sharing certain similarities are illustrated in FIGS. 6-9. One embodiment of retractor 6100 is illustrated in FIGS. 6A-6C, 7A, 8A-8C, and 9A. Another embodiment of retractor 7100 is illustrated in FIGS. 6D-6F, 7B, 8D, and 9B The embodiment of the natural orifice access port or retractor 6100 illustrated in a side view in FIG. 6A can be adapted for use in a transanal surgical procedure. The retractor 6100 comprises an inner or distal ring 6110, an outer or proximal ring 6120, a tubular body 6130, and a funnel segment 6140 extending between and coupling the inner ring 6110 and the outer ring 6120. The tubular body 6130 comprises a relatively flexible material such as a KRATON® material or a silicone rubber material, which is substantially cylindrical in the illustrated embodiment. In other embodiments, the tubular body 6130 has another shape, for example, an oval cross section. Some embodiments of the tubular body 6130 comprise one or more coatings that provide additional functionality, for example, an anti-microbial coating.

Embodiments of the inner ring 6110 are sufficiently flexible and compliant to be compressed and/or deformed for insertion into a body orifice such as a patient's anus during a transanal surgical procedure. When subsequently released within an associated body cavity, the inner ring 6110 substantially returns to its original shape or footprint. In some embodiments, the inner ring 6110 assumes a substantially circular shape in a relaxed state, for example, when released within a body cavity. In other embodiments, the inner ring 6110 has another shape in the relaxed state, for example, an oval. The inner ring 6110 assumes a different shape when compressed for insertion through an incision or body orifice, for example, a substantially oval shape, a generally linear shape, a tear-drop shape, or another suitable shape. Those skilled in the art will recognize that in other embodiments, the inner ring 6110 in the relaxed state has a shape other than round, for example, oval, elliptical, or D-shaped. In other embodiments, the inner ring 6110 is substantially rigid, that is, non-compliant under the ordinary conditions under which it is used. In some embodiments, the inner ring extends outward from the surface of the tubular body, as shown, for example, in FIG. 6A, to thereby aid in retaining the retractor in the body cavity after it is deployed.

Embodiments of the inner ring 6110 can comprise a generally circular cross section. In other embodiments, the inner ring 6110 comprises another cross-sectional shape, for example, at least one of oval or elliptical, tear-drop shaped, and D-shaped. For example, in embodiments illustrated in FIGS. 6D-6F, the inner ring 7110 can have a cross-sectional shape that is substantially flush with the tubular body 7130 of the retractor 7100 as further described herein. Those skilled in the art will understand that other cross sections are used in other embodiments. As further discussed herein with respect to the flexion region of the inner ring 6110, some embodiments of the inner ring 6110 comprise at least one notch and/or weak spot, which facilitate folding or deforming the inner ring 6110, thereby facilitating insertion and/or removal of the inner ring 6110.

Returning to FIG. 6A, the outer ring 6120 is proximal the funnel section 6140. In the illustrated embodiment, the outer ring 6120 has a substantially circular footprint. As further discussed herein, the outer ring 6120 can be sized and configured to sealingly couple to a cap or other access device thereon. In some embodiments, one or more suture points 6160 can be disposed on the retractor 6110 adjacent the outer ring 6120.

Figure 6A:
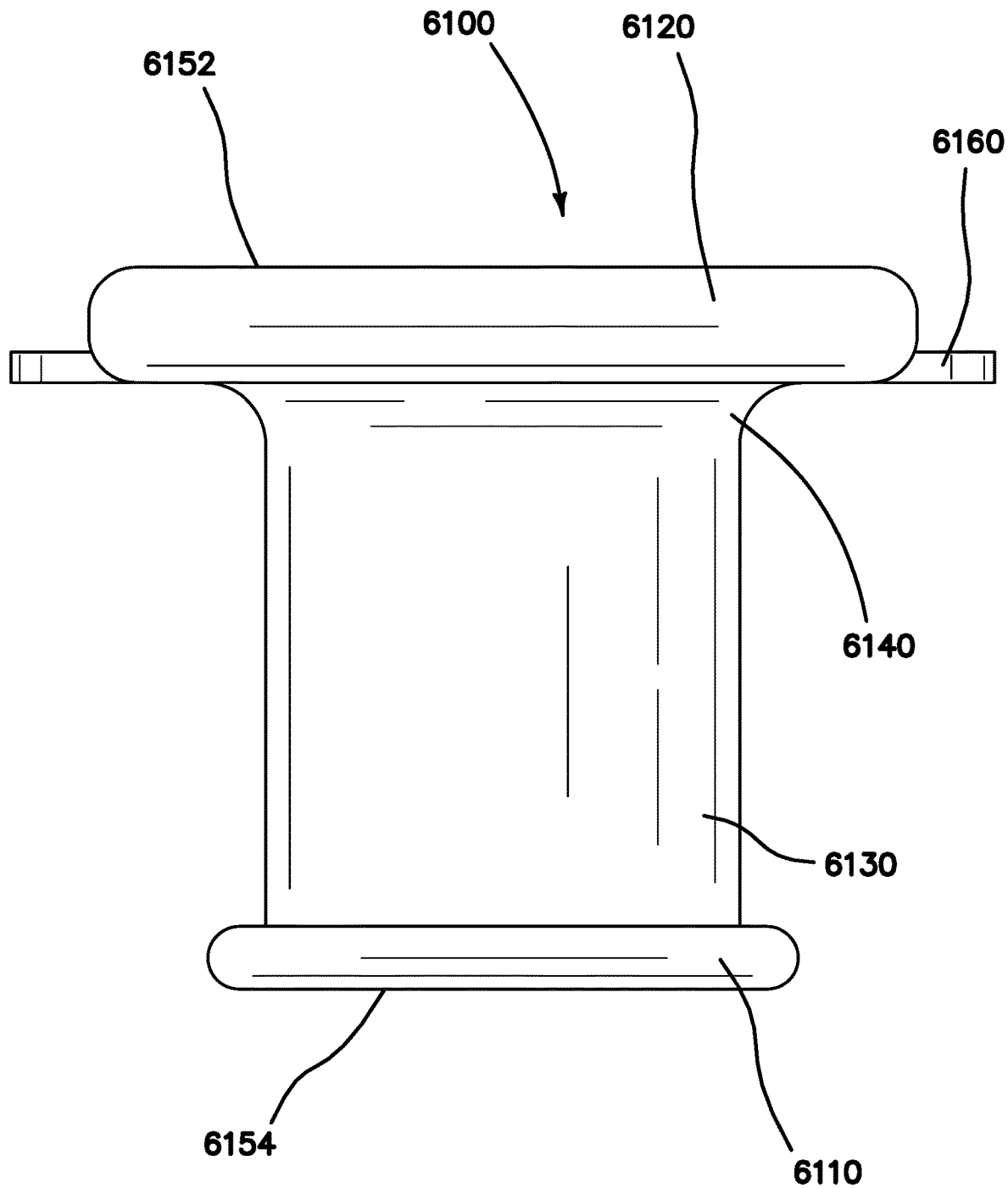
FIG. 6A is a side view of an embodiment of a natural orifice retractor.
Figure 6B:
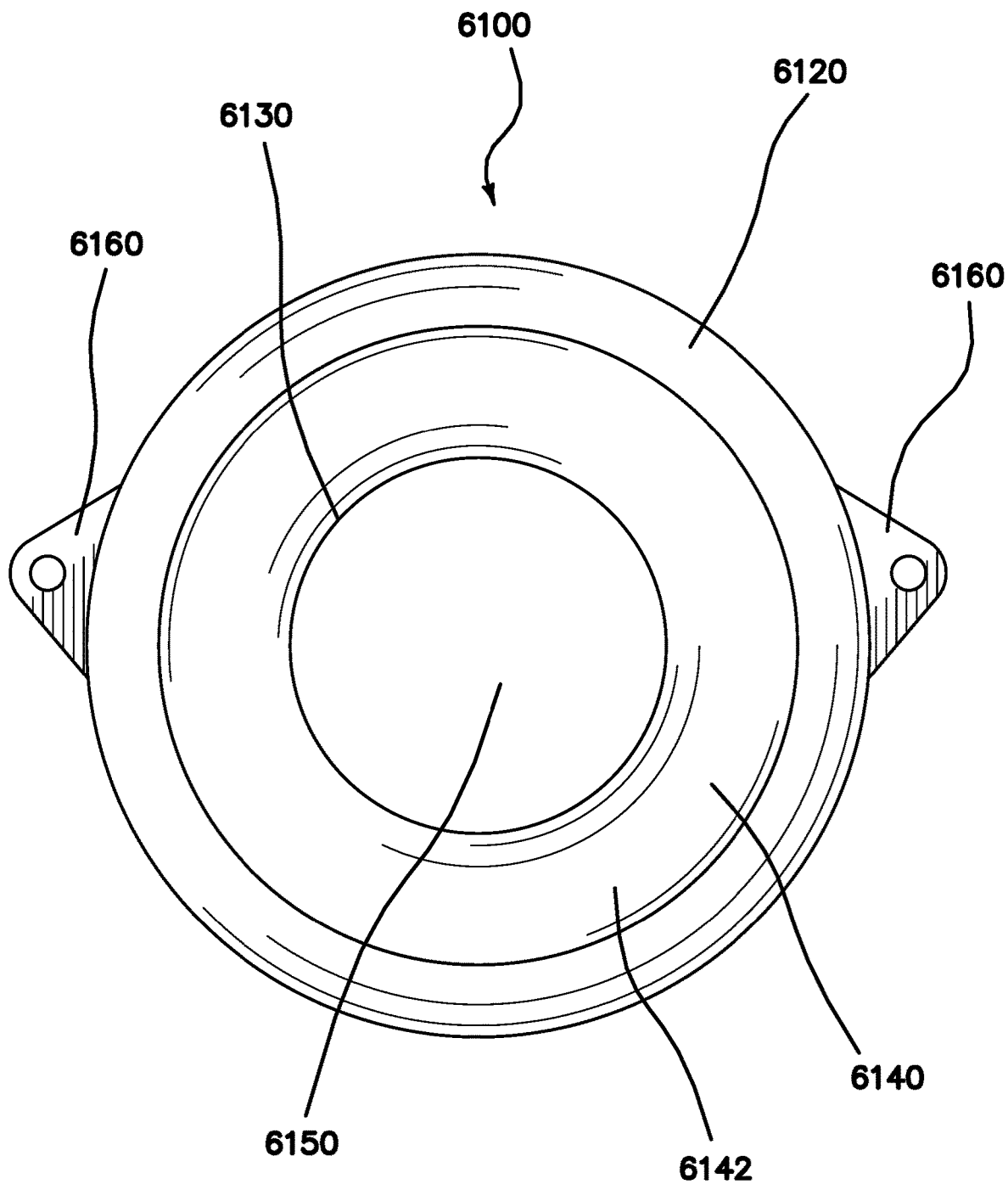
FIG. 6B is a top view of the natural orifice retractor of FIG. 6A.

With reference to FIG. 6B, a top view of retractor 6100 is illustrated. In the illustrated embodiment, outer ring 6120 has a generally circular profile. Additionally, in the illustrated embodiment, two suture points 6160 are generally diametrically opposed relative to the generally circular profile of the outer ring 6120. In other embodiments, the retractor can include more or fewer than two suture points disposed of various locations relative to the outer ring 6120.

With continued reference to FIG. 6B, the tubular body 6130 has a generally circular profile defining a generally cylindrical passage 6150. The generally cylindrical passage 6150 is desirably large enough to accommodate more than one laparoscopic instrument there through such that a single natural orifice access device can be used to provide access for multiple surgical instruments in a body cavity. Moreover, generally cylindrical passage 6150 is desirably large enough such that multiple surgical instruments positioned there through can be translated or pivoted relative to one another, allowing a surgeon to manipulate the instruments as desired during a surgical procedure. The generally cylindrical passage extends between a proximal end 6152 of the retractor 6100 adjacent the outer ring 6120 to a distal end 6154 of the retractor 6100 adjacent the inner ring 6110 (FIG. 6A).

With continued reference to FIG. 6B, in the illustrated embodiment, the funnel segment 6140 provides a diametric reduction between the relatively large diameter of the outer ring 6120, which is sized and configured to be removably coupled to an access device such as a cap, and the relatively smaller diameter of the passage 6150, which is sized to fit within a natural orifice with minimal distention of the orifice. The funnel segment 6140 has an inner surface 6142 which can provide a bearing surface for an obturator used to advance to the retractor 6100 into a body cavity. In some embodiments, the funnel segment 6140 can have a substantially linear taper between the relatively large diameter and the relatively smaller diameter such that the inner surface 6142 is a frusto-conical segment. In other embodiments, the funnel segment 6140 can have a curved profile between the relatively large diameter and the relatively smaller diameter.

Figure 6C:
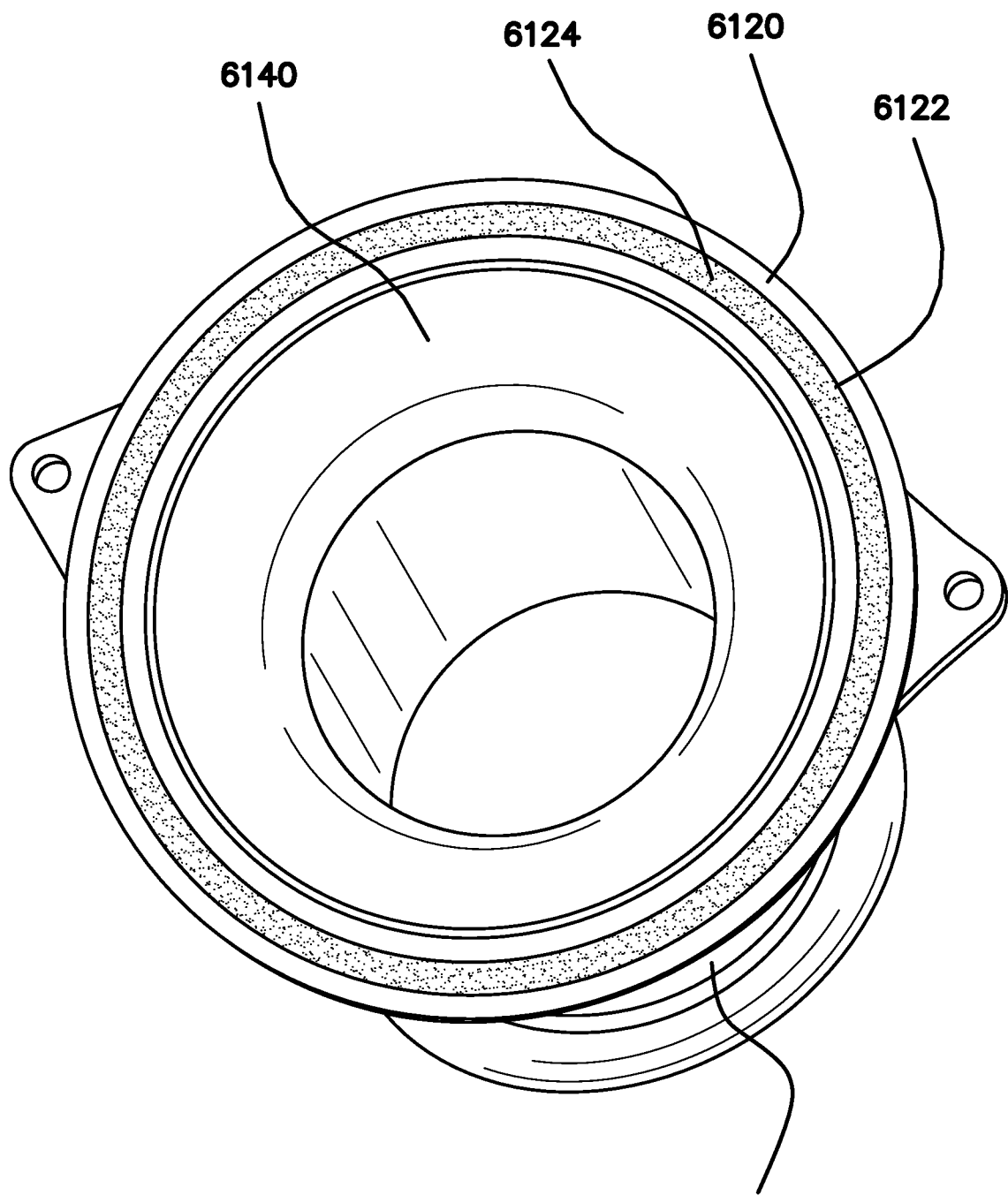
FIG. 6C is a partial cut away of the natural orifice retractor of FIG. 6A.
Figure 6D:
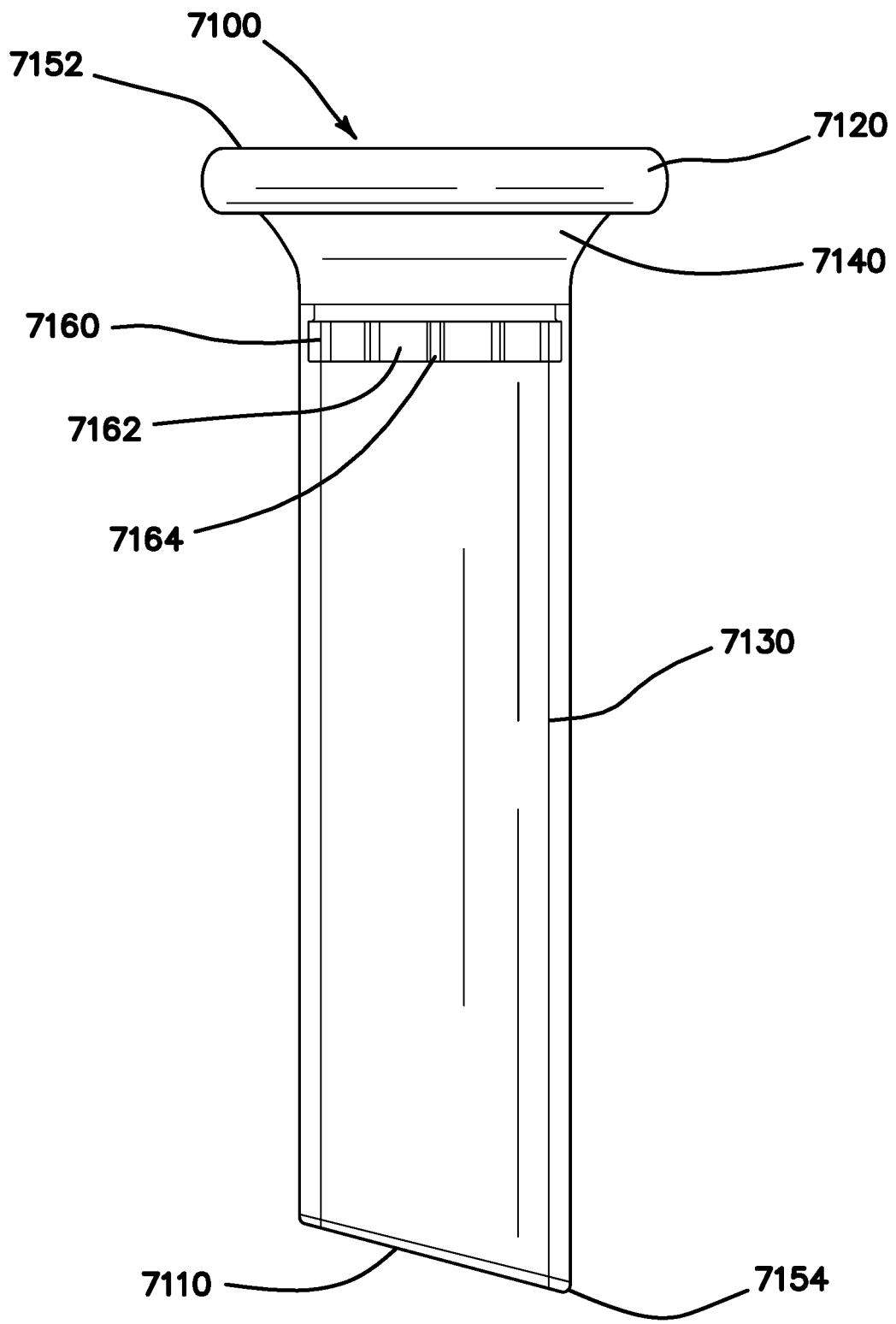
FIG. 6D is a side view of another embodiment of a natural orifice retractor.
Figure 6E:
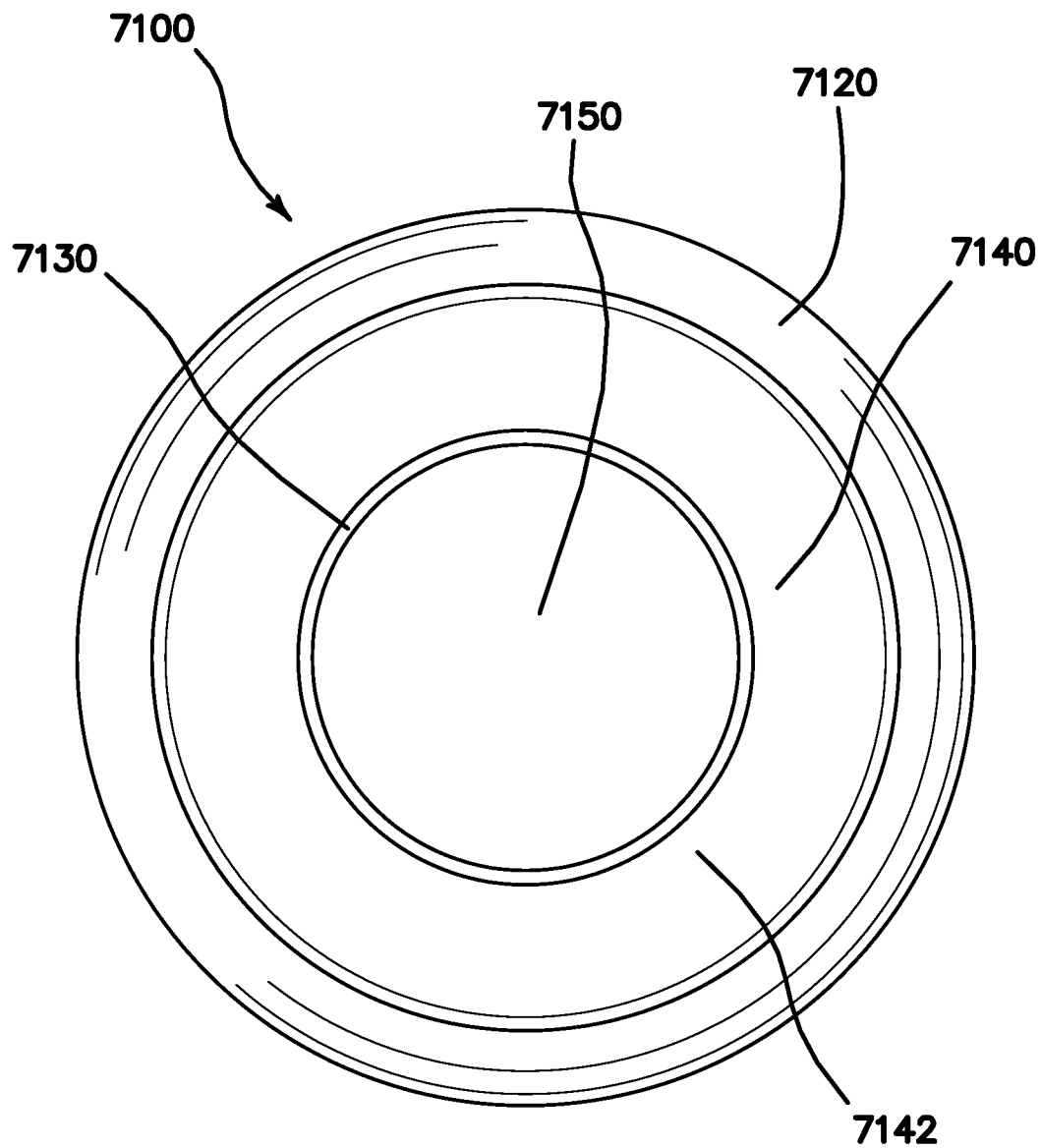
FIG. 6E is a top view of the natural orifice retractor of FIG. 6D.
Figure 6F:
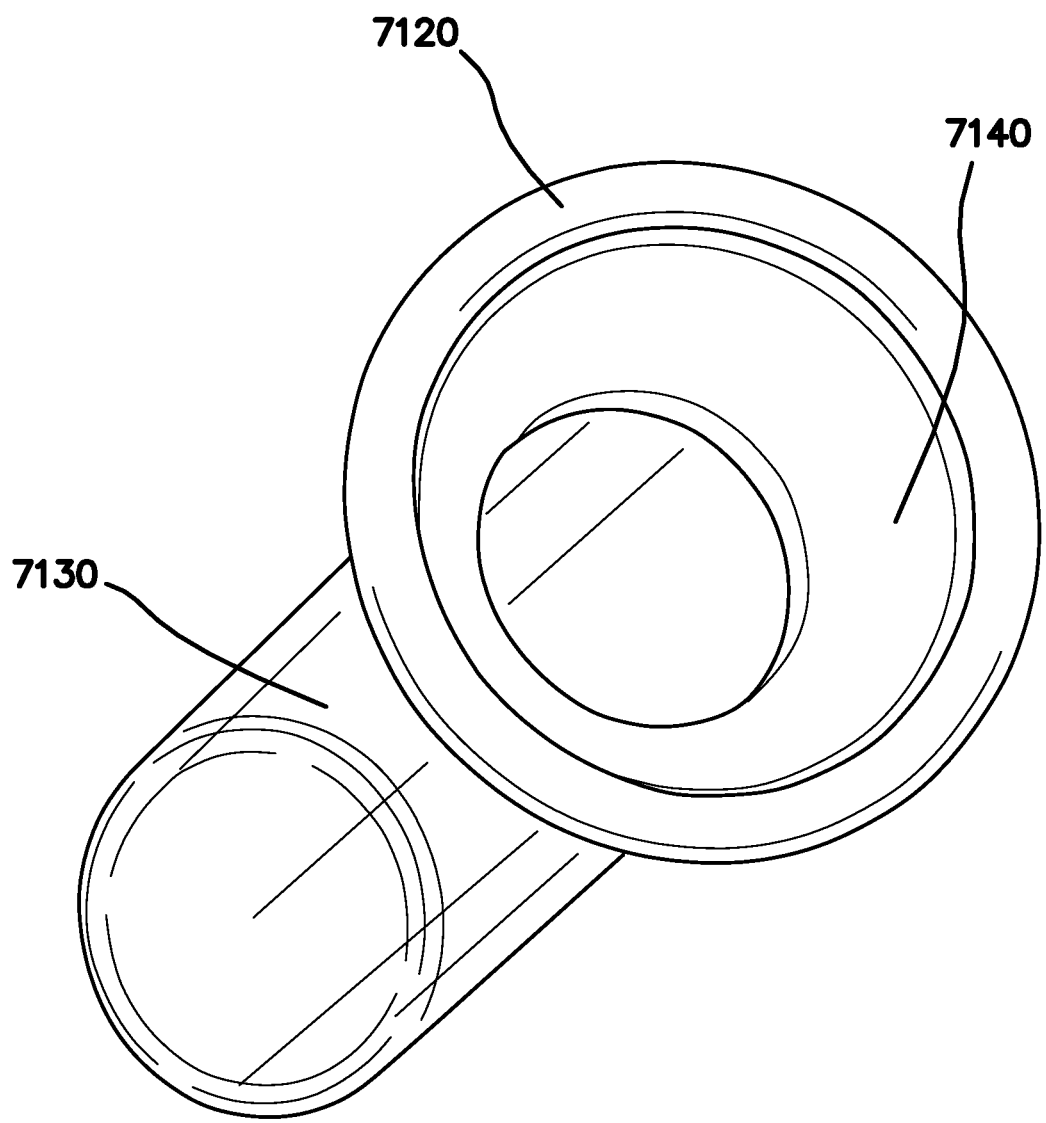
FIG. 6F is a perspective view of the natural orifice retractor of FIG. 6A.
Figure 6G:
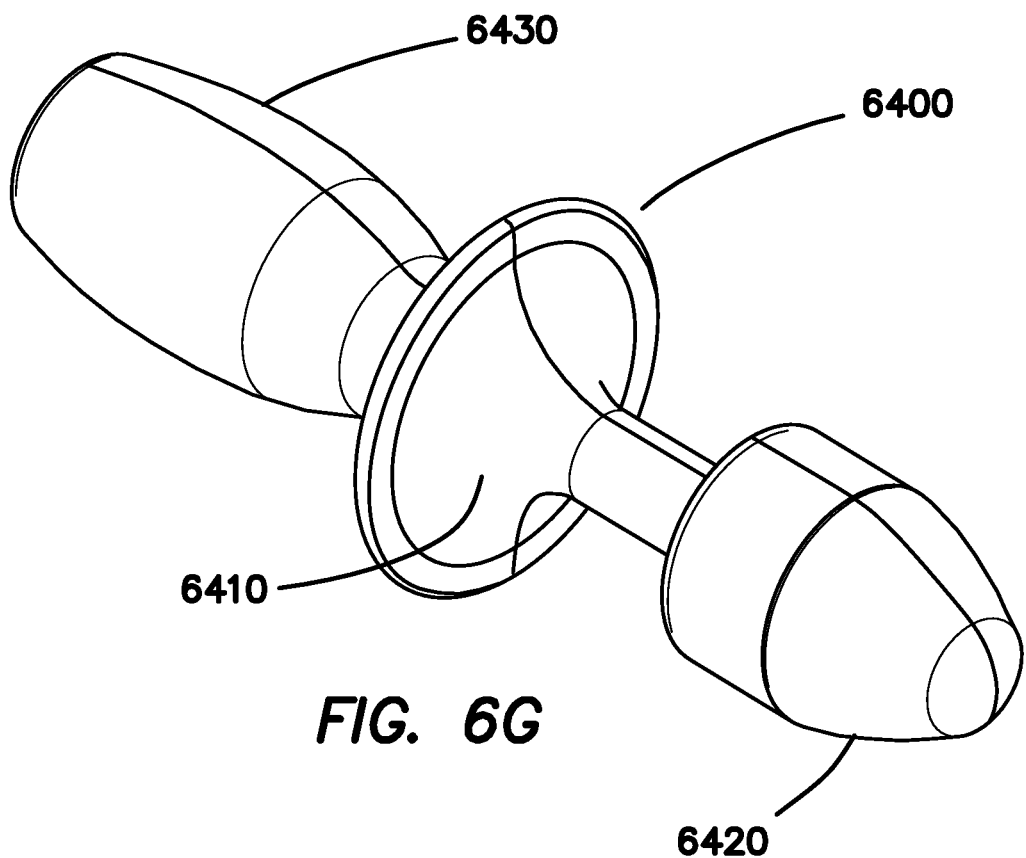
FIG. 6G is a perspective view of an obturator adapted to facilitate introduction of a natural orifice retractor into a body orifice such as an anus.
Figure 6H:
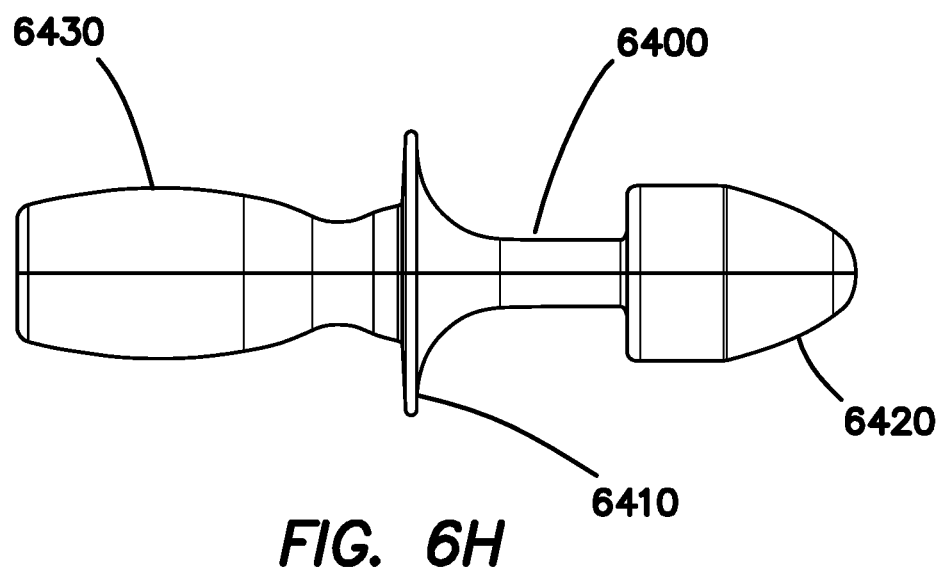
FIG. 6H is a side view of the obturator of FIG. 6G.

In some embodiments, a natural orifice access system can include a retractor 6100 and an optional obturator 6400 (FIG. 6G-6H). The obturator can have a proximal bearing surface 6410 sized and configured to bear against the inner surface 6142 of the funnel segment 6140 and a distal dilation surface 6420 sized and configured to expand a natural orifice for passage of the retractor 6100. Thus, during insertion of the retractor 6100 into a natural orifice, the dilation surface 6420 expands a pathway to a surgical site in a body cavity while the obturator bears on the inner surface 6142 of the funnel segment 6140 to advance the retractor 6100 into position in the surgical site. Furthermore, in some embodiments, the obturator can have a handle 6430 at a proximal end thereof adapted to facilitate selective twisting or rotation of the obturator about a longitudinal axis thereof during insertion.

It can be desirable that the outer ring 6120 is relatively stiff compared with the relatively flexible tubular body 6130 of the retractor 6100 so that the outer ring 6120 can sealingly engage an access device such as a cap. With reference to FIG. 6C, a perspective view of the retractor is illustrated with a partial cutaway of the outer ring 6120. In the illustrated embodiment, the outer ring 6120 includes an annular groove 6122 formed therein in which a reinforcing member 6124 is disposed. In some embodiments, the reinforcing member 6124 can comprise a metallic member such as a wire formed into a ring shape. For example, in some embodiments the reinforcing member 6124 can comprise a stainless steel ring positioned within the groove 6122 during manufacture of the retractor 6100. In other embodiments, the reinforcing number 6124 can comprise an injectable nonmetallic member. For example, in some embodiments, a glass filled polymer or polycarbonate material can be injected into the groove 6122 during manufacture of the retractor 6100.

While the illustrated embodiments of retractor 6100 include a reinforcing member to enhance the rigidity of the outer ring 6120, in other embodiments, the retractor 6100 can be formed in a multiple-shot molding process. For example, in some embodiments, an inner segment of the retractor defined by the tubular body 6130 and the inner ring 6110 is formed in one molding operation from a flexible material, and an outer segment of the retractor 6100 defined by the funnel segment 6140 and the outer ring 6120 is formed in another molding operation from a relatively rigid material such as a polycarbonate material or other suitable material. One embodiment of retractor 7100 formed in a multiple-shot molding process is illustrated in FIGS. 6D-F, 7B, 8D, and 9B.

With continued reference to FIG. 6C, the illustrated embodiment includes a continuous generally annular groove. In other embodiments, a plurality of noncontiguous recesses can each receive one of a plurality of reinforcing members. Moreover, in some embodiments, the outer ring can include two or more concentric generally annular grooves, which each receive a corresponding reinforcing member.

Figure 7A:
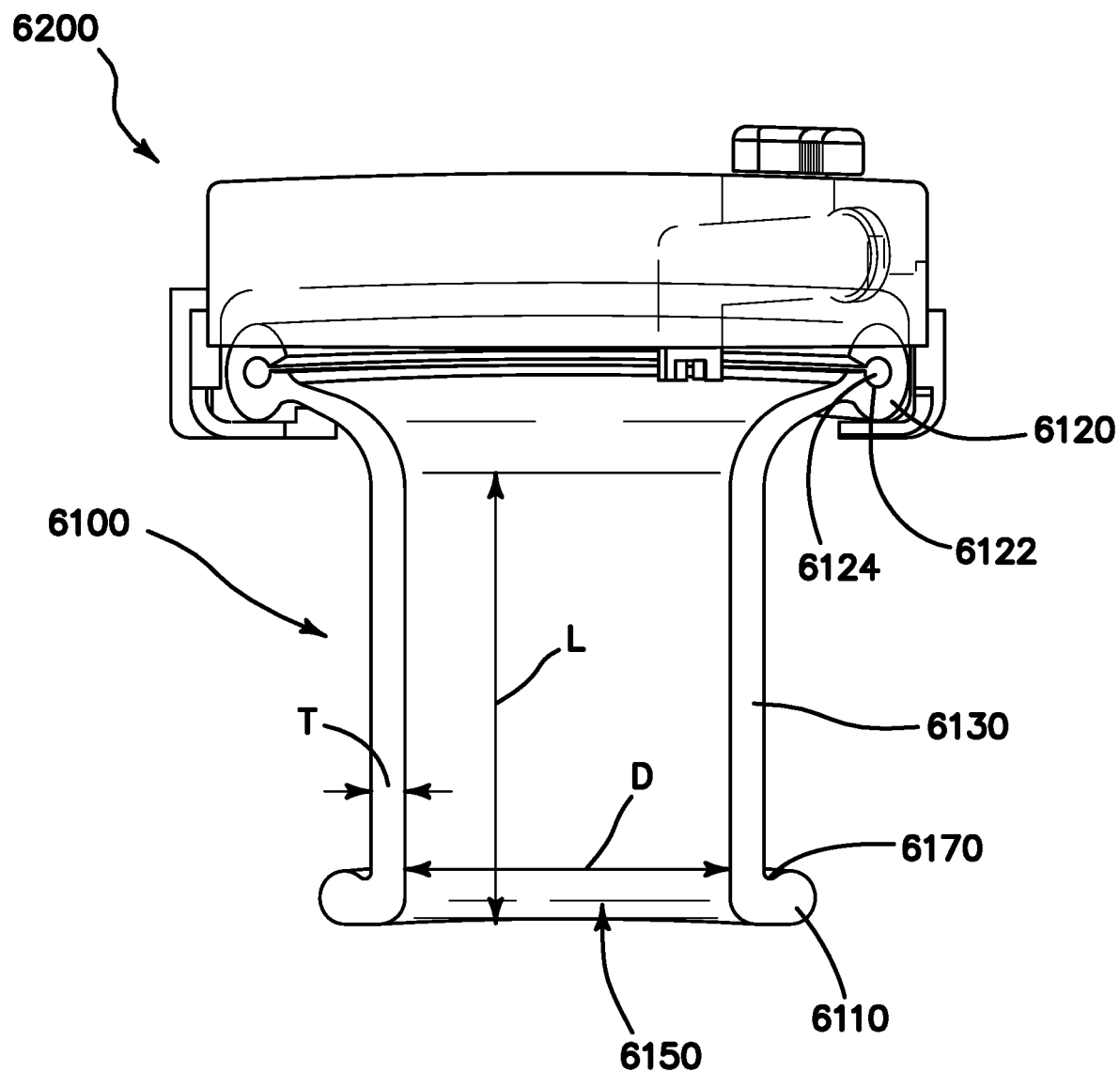
FIG. 7A is a partial side cross section of the natural orifice retractor of FIG. 6A with a gel cap coupled therewith to form one embodiment of natural orifice access device.

With reference to FIG. 7A, a cross-sectional view of a natural orifice access device including a retractor 6100 and a removable cap 6200 is shown. In the illustrated embodiment, the tubular body 6130 is formed of a flexible material having a predetermined fixed length L, inner diameter D, and wall thickness T. The fixed length L, inner diameter D, and wall thickness T are selected to accommodate the anatomy of a natural orifice, such as the anal orifice of a majority of patients. It is contemplated that the retractor 6100 can be scaled to different sizes for patients of different ages. Furthermore, in some embodiments, it is contemplated that the retractor can include a telescopic tubular body such that the tubular body can be selectively positioned at a variety of lengths depending on patient anatomy and the location of the surgical site within the body cavity. Desirably, the wall thickness T and material of the tubular body 6130 are selected such that the tubular body 6130 is resilient enough to maintain the passage 6150 there through when positioned in the natural orifice. Moreover, desirably, the inner diameter, D is sufficiently large to accommodate multiple surgical instruments. For example, in embodiments of the retractor 6100 adapted for use in a TEMS procedure, the inner diameter D and thickness T can be sized such that an outer diameter of the retractor can be between approximately 30 mm and 70 mm, desirably between approximately 35 mm and 50 mm, and in one embodiment approximately 40 mm. Additionally, desirably, the fixed length L is sufficiently long such that the inner ring 6110 can be positioned at a surgical site within a body cavity and the outer ring 6120 can be positioned outside the natural orifice. In some embodiments, the fixed length L is of a length such that the device has an overall length between the proximal end 6152 and the distal end 6154 of between approximately 10 mm and approximately 100 mm, desirably between approximately 20 mm and 80 mm, more desirably between approximately 30 mm and 60 mm, and in one embodiment, approximately 40 mm.

With continued reference to FIG. 7A, in some embodiments, the annular groove 6122 can be open to an inner surface of the outer ring 6120. Thus, the retractor 6100 can be formed of a flexible material in a single molding operation with the annular groove 6122 having an opening, and the reinforcing member 6124 can be subsequently inserted into the upper groove 6122.

With continued reference to FIG. 7A, in some embodiments, the retractor 6100 can include a flexion region between the tubular body 6130 and the inner ring 6110, such as an undercut 6170. Advantageously, the flexion region can allow the inner ring 6110 to flex or rotate relative to the tubular body 6130 during insertion such that the inner ring 6110 presents a relatively small outer diameter in an insertion configuration and a relatively larger outer diameter in an undisturbed configuration.

Figure 7B:
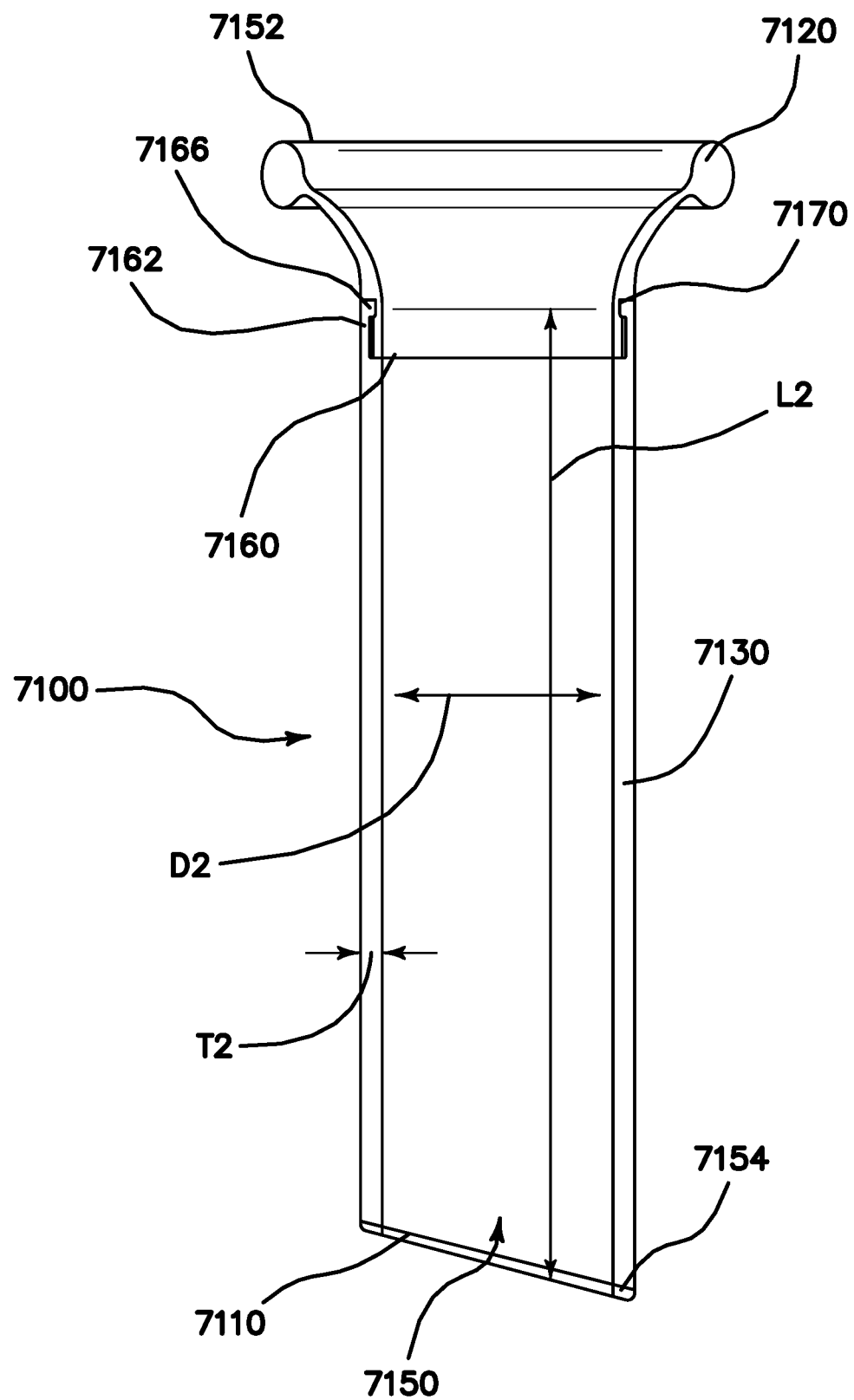
FIG. 7B is a side cross section of the natural orifice retractor of FIG. 6D.
Figure 7C:
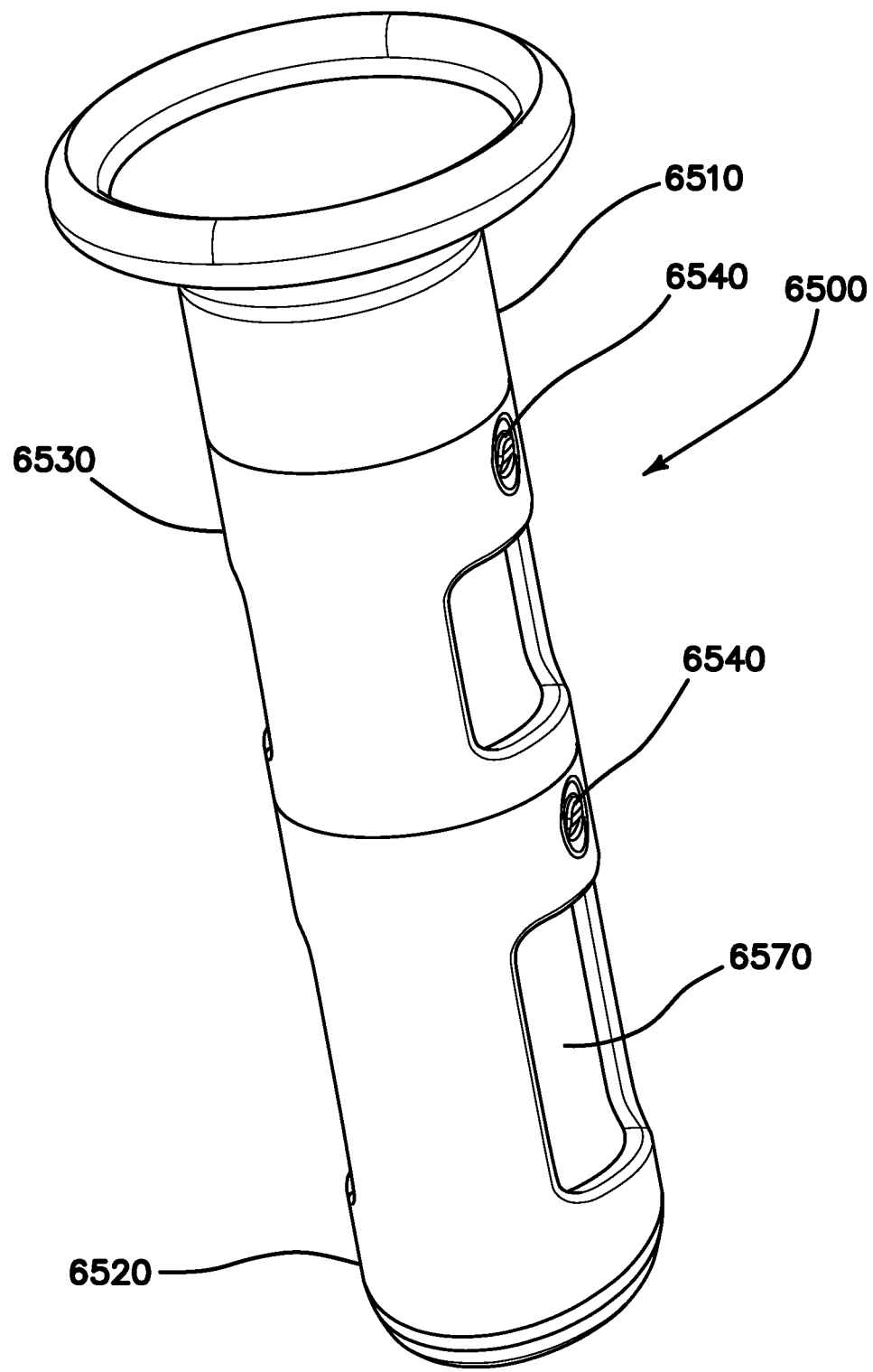
FIG. 7C is a perspective view of a natural orifice retractor formed from sections and having cut-out portions or windows in the tubular body of the retractor.
Figure 7D:
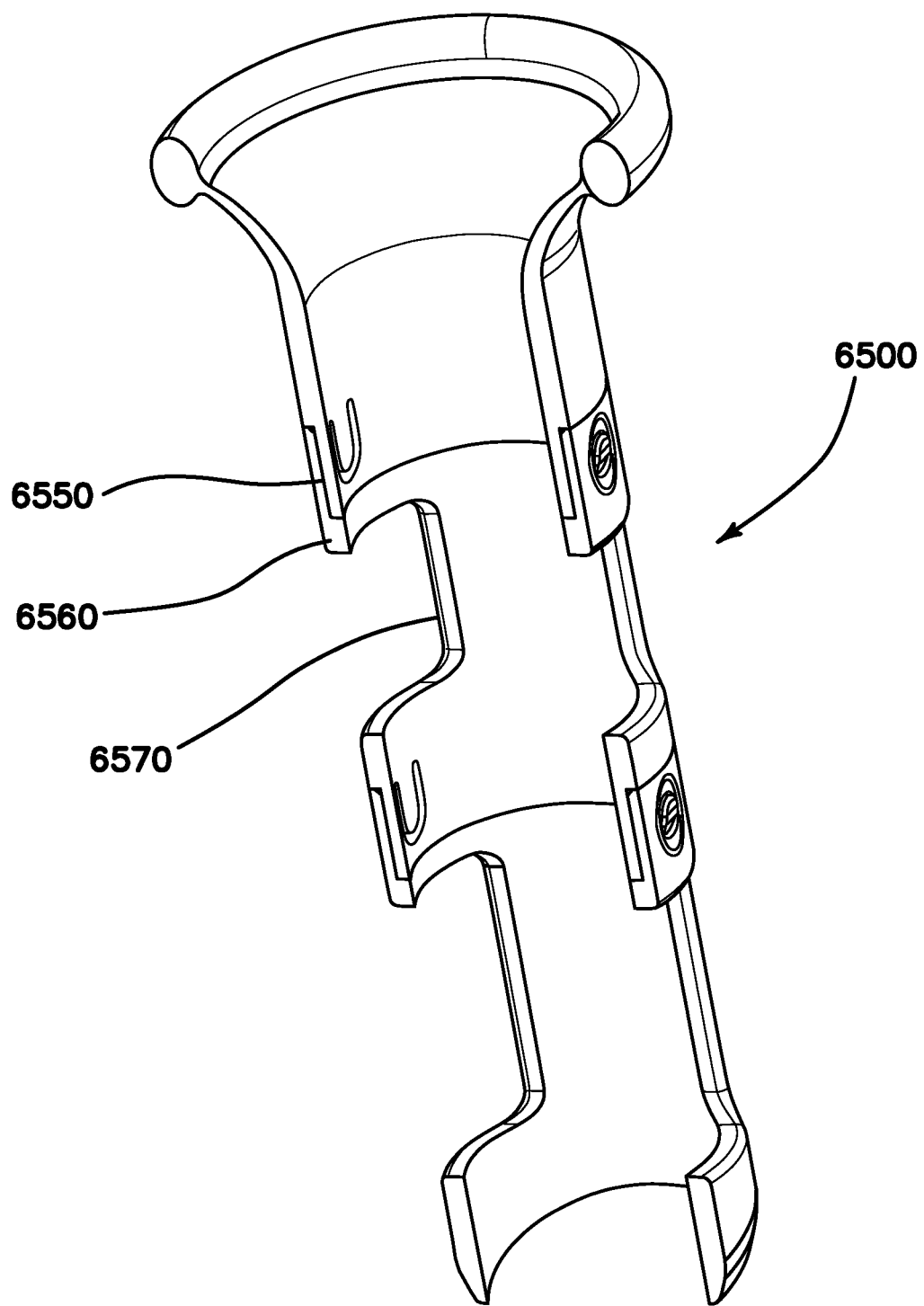
FIG. 7D is a cutaway view of the retractor of FIG. 7C showing the slidable engagement of the sections.
Figure 7E:
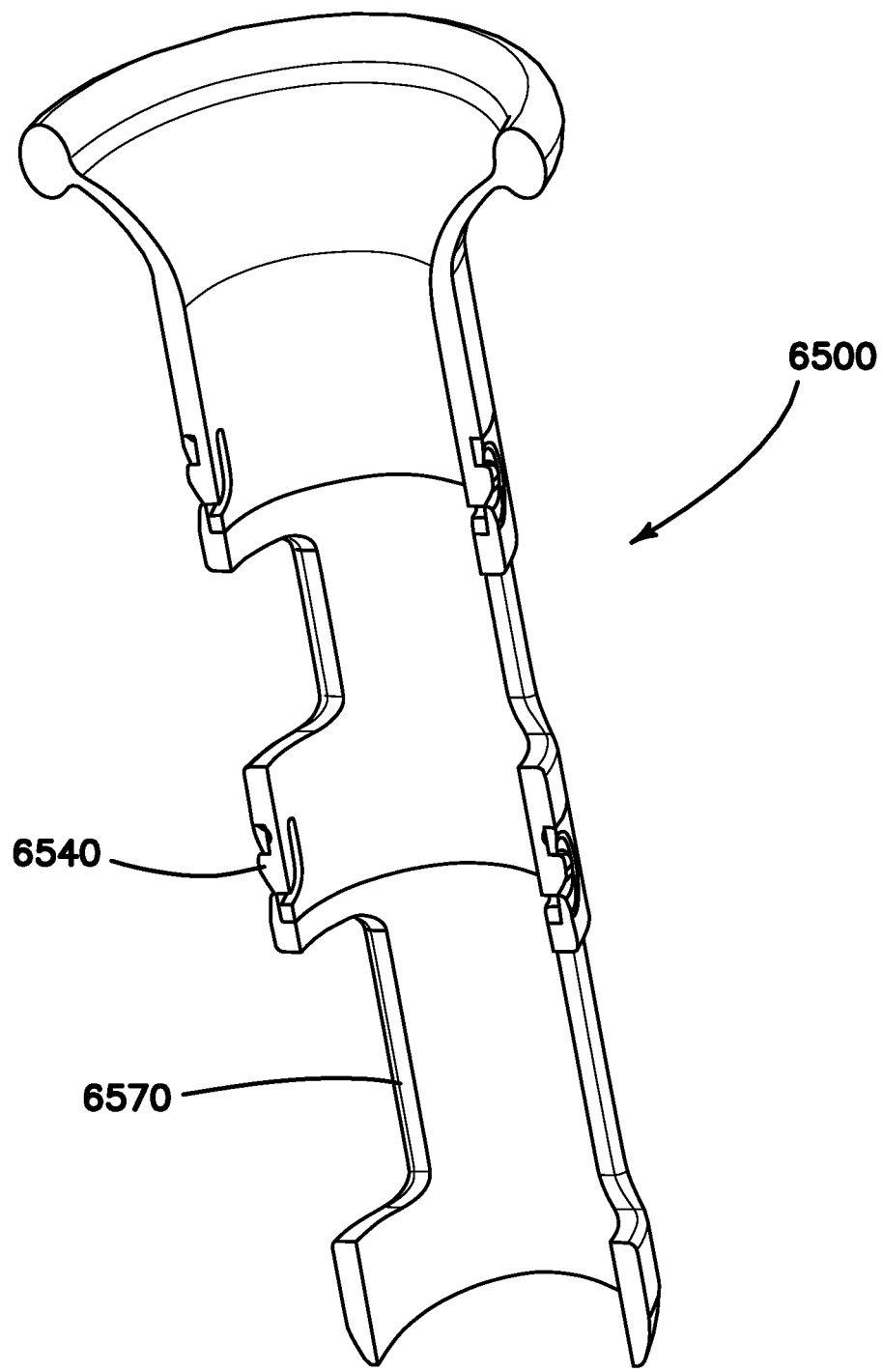
FIG. 7E is a cutaway view of the retractor of FIG. 7C showing the snap-lock mechanism securing the sections together.
Figure 7F:
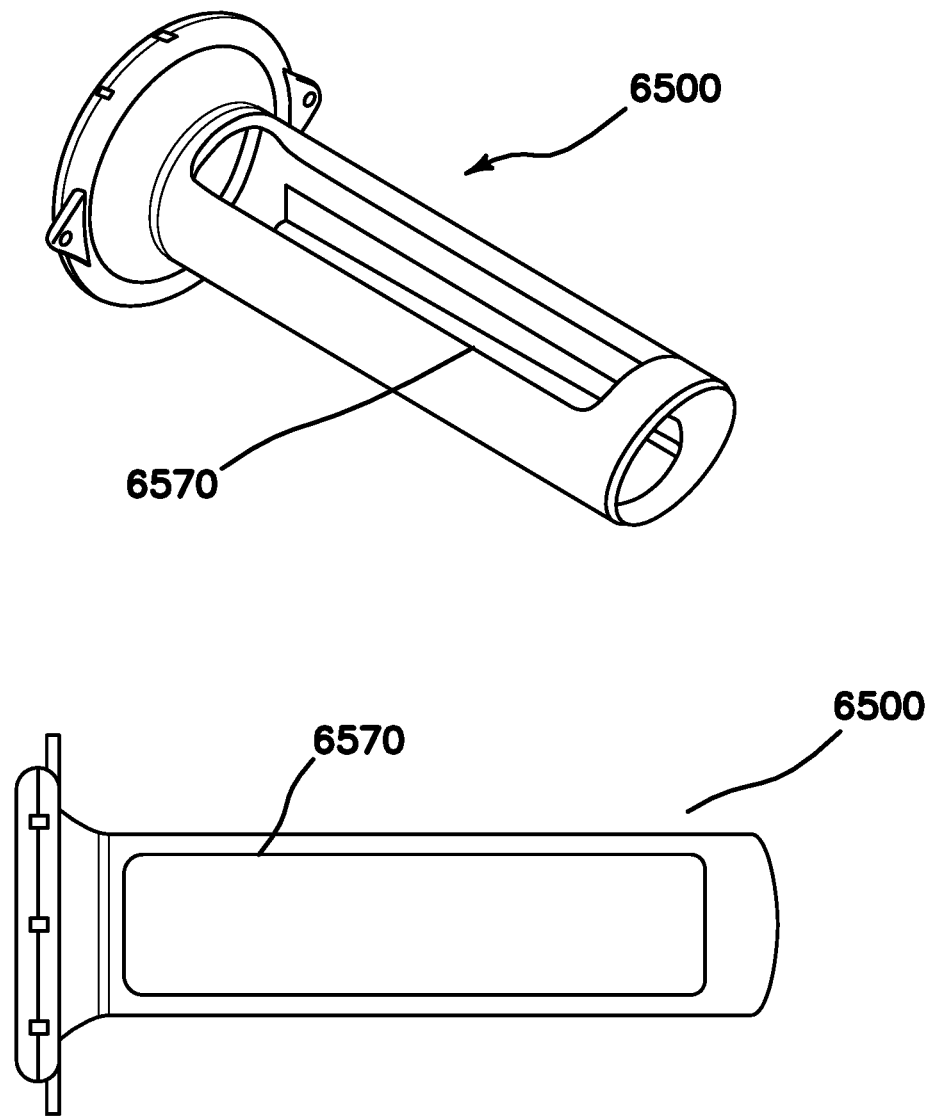
FIG. 7F is a perspective view and a side view of an alternative embodiment of a retractor having cut-out portions or windows in the tubular body of the retractor.
Figure 7G:
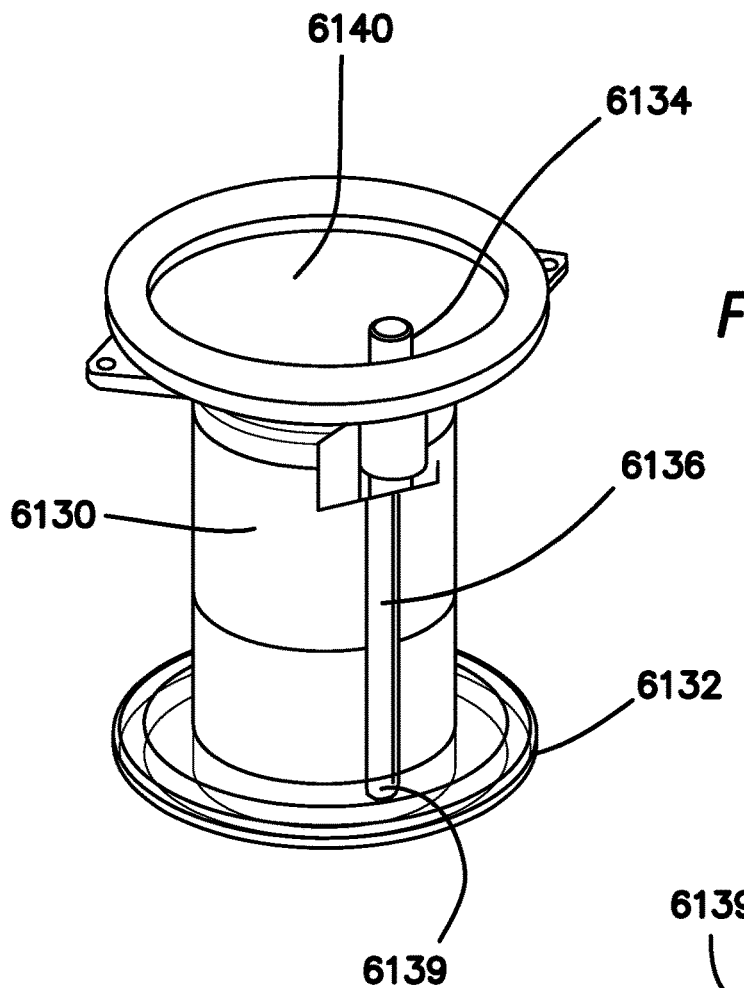
FIG. 7G is a perspective view of an alternative embodiment of a retractor having an inflatable member.

In other embodiments, shown in FIG. 7G, the inner ring can comprise an inflatable member 6132 such as an annular balloon coupled to a gas or fluid source that can be selectively inflated and deflated between a deflated, relatively small diameter state for insertion and removal, and an inflated, relatively high diameter state for retention in a body cavity. An inflation port 6134, for example a check valve, affixed to the funnel portion 6140 of the retractor, is connected to the inflatable member 6132 through a channel 6136 within the wall of the tubular body 6130. Fluid or gas introduced through the inflation port flows through the channel into the inflatable member to thereby inflate the member.

The channel 6136 runs through the tubular body, generally parallel to the longitudinal axis of the tubular body, with a proximal opening interacting with the inflation port 6134 and a distal opening 6139 into outer surface of the tubular body at the inflatable member. In one aspect, the inflation port 6134 may include a normally closed check valve having a spring-loaded plunger. In a further aspect, the check valve may include a Luer lock. It is contemplated that other inflation ports that are well known in the art may be used.

Figure 7H:
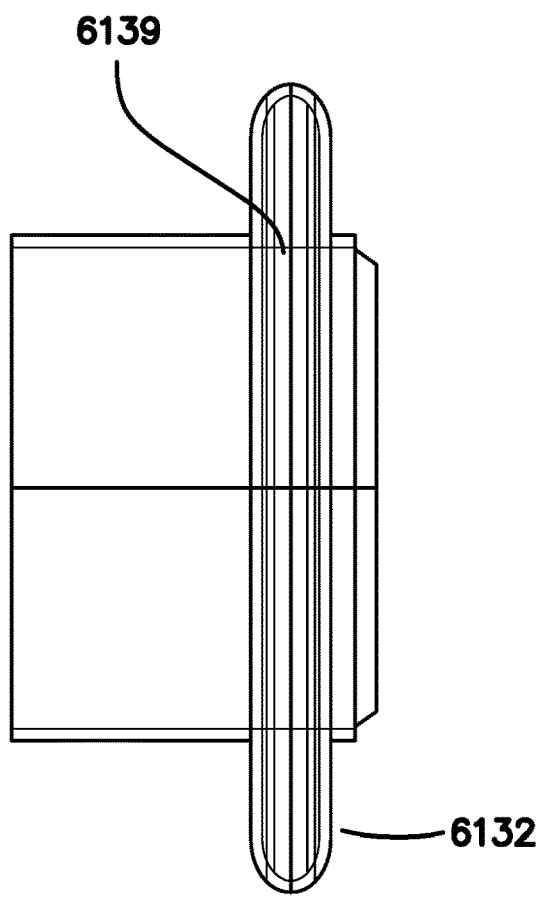
FIG. 7H shows a close-up view of the inflatable member.

In this embodiment, the tubular body 6130 is preferably comprised of a relatively rigid material, such as a polycarbonate. The tubular body has an inflatable member at the distal end that may be created by heat shrinking polyolefin tubing around the outside of the tubular body. The distal end of the body/tubing assembly is then heated for approximately 30 to 40 seconds, and then placed inside a mold and injected with air to give the inflatable member an annular balloon shape as seen in FIG. 7H, or any other desired shape, depending on the configuration of the mold. The inflatable member 6132 should have sufficient impermeability properties to substantially prevent inflation gas or fluid from permeating through a wall of the inflatable member.

In one embodiment, the inflatable member 6132 may include a substantially toroid shape upon inflation. In another embodiment, the inflatable member may include a disc shape upon inflation. In another embodiment, the inflatable member 6132 may be a fluted balloon. Other shapes suitable for particular natural orifices will be appreciated by one skilled in the art.

Figure 7I:
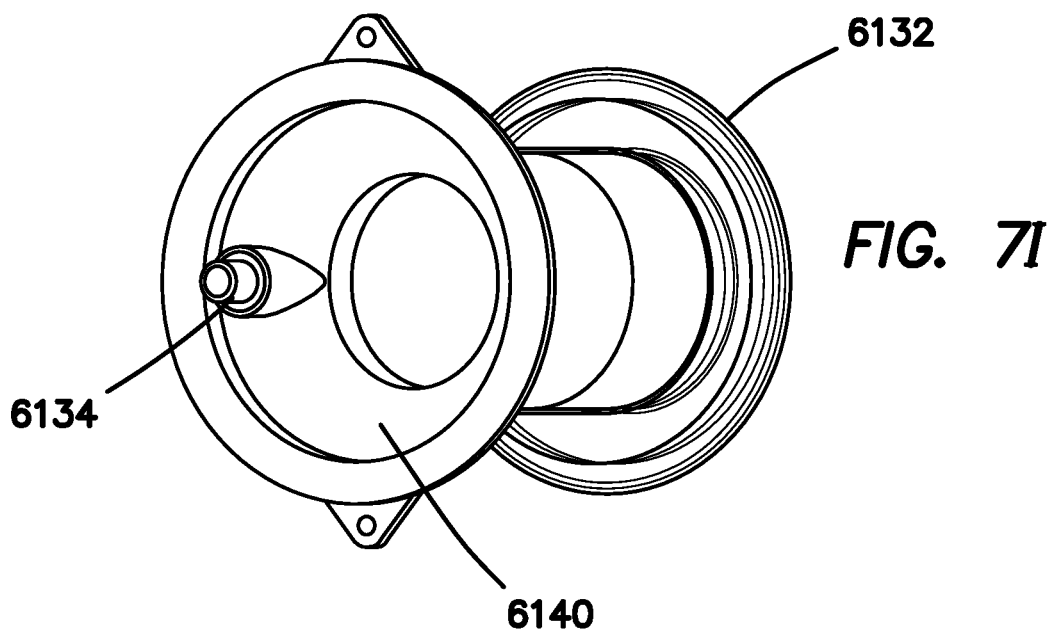
FIG. 7I is a top-down perspective view of a retractor showing the check valve port of inflating the inflatable member.
Figure 7J:
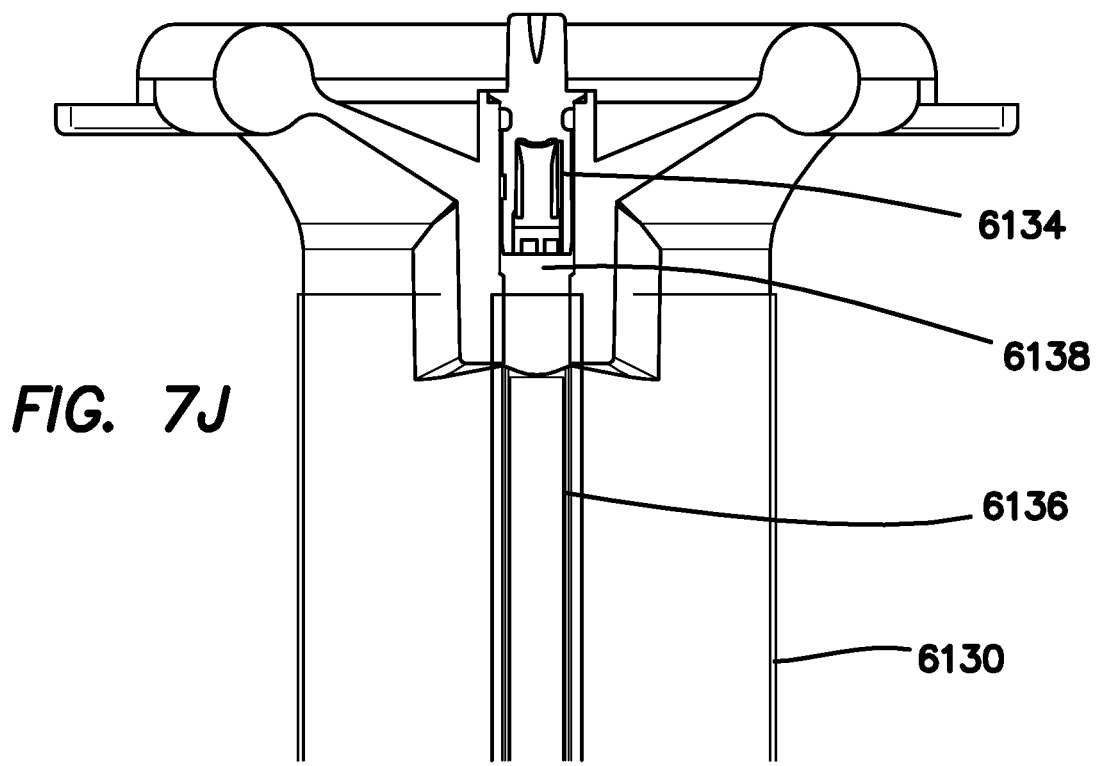
FIG. 7J is a cutaway side view showing the check valve and channel disposed in the tubular body of the retractor.
Figure 7K:
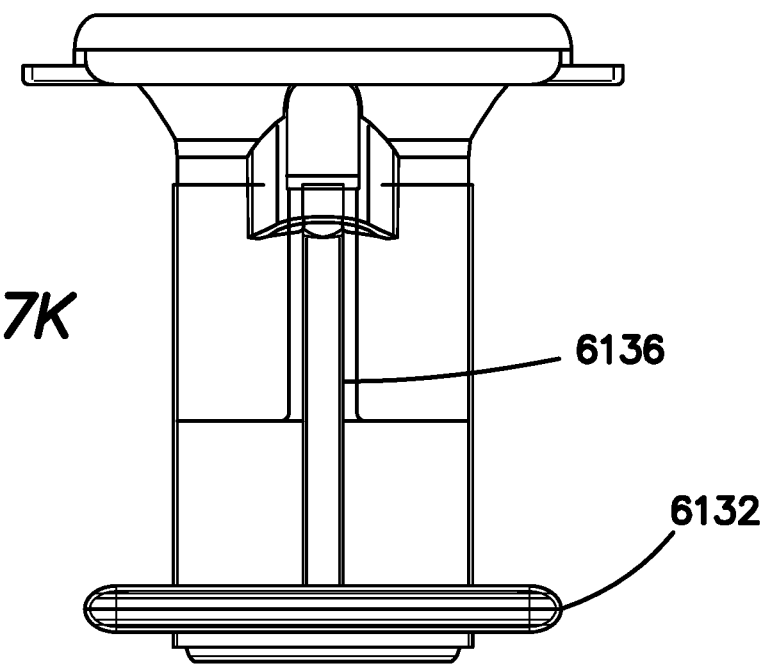
FIG. 7K is a side view of a retractor showing the channel disposed between the check valve and the inflatable member.
Figure 7L:
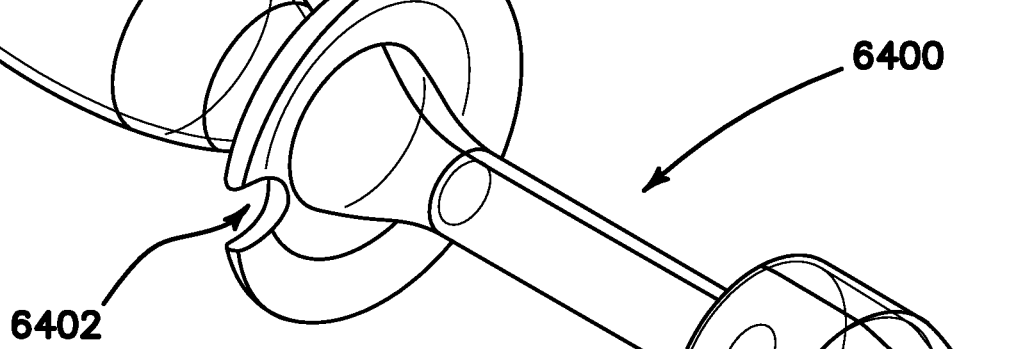
FIG. 7L is a perspective view of an obturator, modified with an indent to provide clearance for the inflation port shown in FIGS. 7J and 7K and adapted to facilitate introduction of a natural orifice retractor into a body orifice such as an anus.

In use, the inflatable member may be inflated after the retractor is disposed within the natural orifice by inserting a syringe into the valve 6134 located at the proximal end 6138 of the channel within the tubular body (see FIG. 7I). As shown in FIGS. 7J and 7K, the port leads into the channel 6136, which allows the fluid or gas from the syringe to travel to the inflatable member 6132. In this embodiment, the optional obturator 6400 may be modified with an indent 6139 to provide clearance for the inflation port, as shown in FIG. 7L.

Figure 8A:
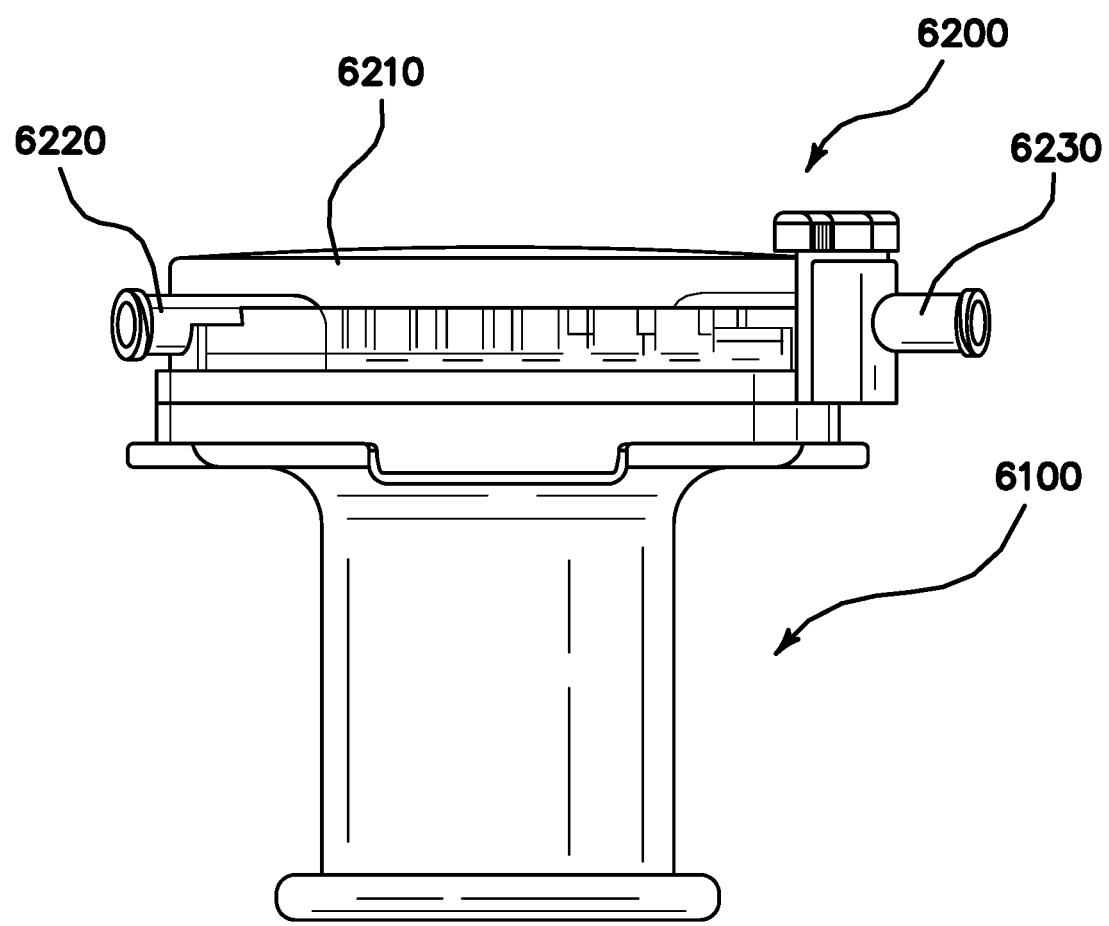
FIG. 8A is a side view of the natural orifice access device of FIG. 7A.

With reference to FIG. 8A, a side view of a natural orifice access device having a cap 6200 removably coupled to a retractor 6100 is illustrated. In the illustrated embodiment, the cap 6200 comprises a sealable access surface 6210 such as a gel pad surface as described in further detail herein. In certain embodiments, the cap 6200 can also comprise at least one gas or fluid port 6220, 6230. In the illustrated embodiment, the cap 6200 comprises two gas or fluid ports 6220, 6230, such that one port can be used for gas insufflation and the other port can be used for ventilation for example when electrosurgery is performed through the access device. In certain embodiments, at least one of the gas or fluid ports 6220, 6230 comprises a valve such as a stopcock valve to selectively control the flow of fluid there through.

Figure 8B:
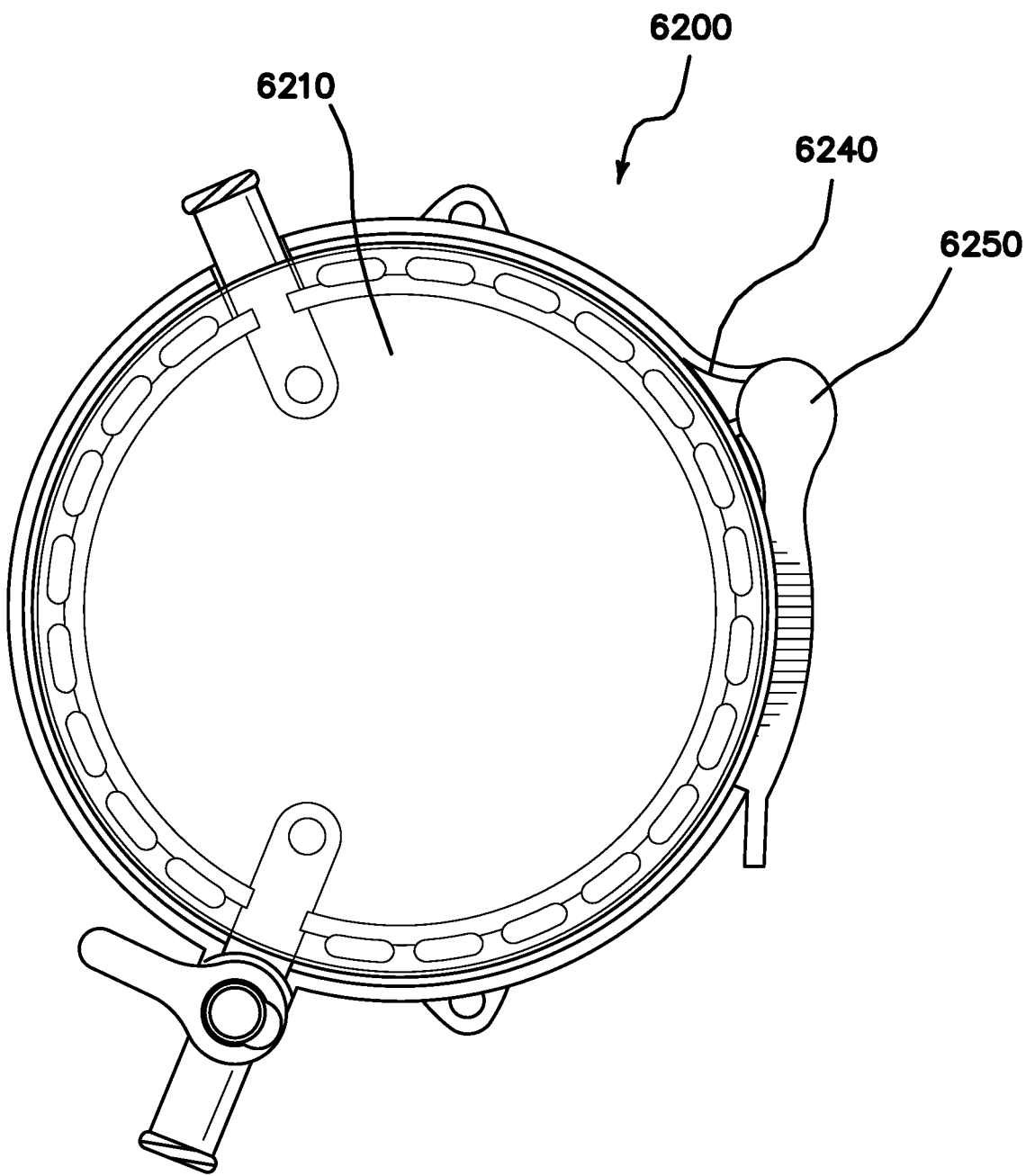
FIG. 8B is a top view of the natural orifice access device illustrated in FIG. 7A.

With reference to FIG. 8B, a top view of the natural orifice access device is illustrated. The sealable access surface 6210 can be encircled by and restrained by an annular frame 6240 such as a split ring having a clamp 6250. The clamp 6250 can be movable between an open configuration in which the cap 6200 is selectively removable from the retractor 6100 and a clamped configuration in which the cap 6200 can be secured to the retractor 6100. For example, the annular frame 6240 can be positioned peripherally around the outer ring 6120 with the clamp 6250 in the open configuration and the clamp moved to the clamped configuration to sealingly fix the cap 6200 to the retractor 6100. Accordingly, the cap 6200 can be easily removed during a surgical procedure to facilitate removal of excised tissue from a surgical site through the retractor 6100.

Figure 8C:
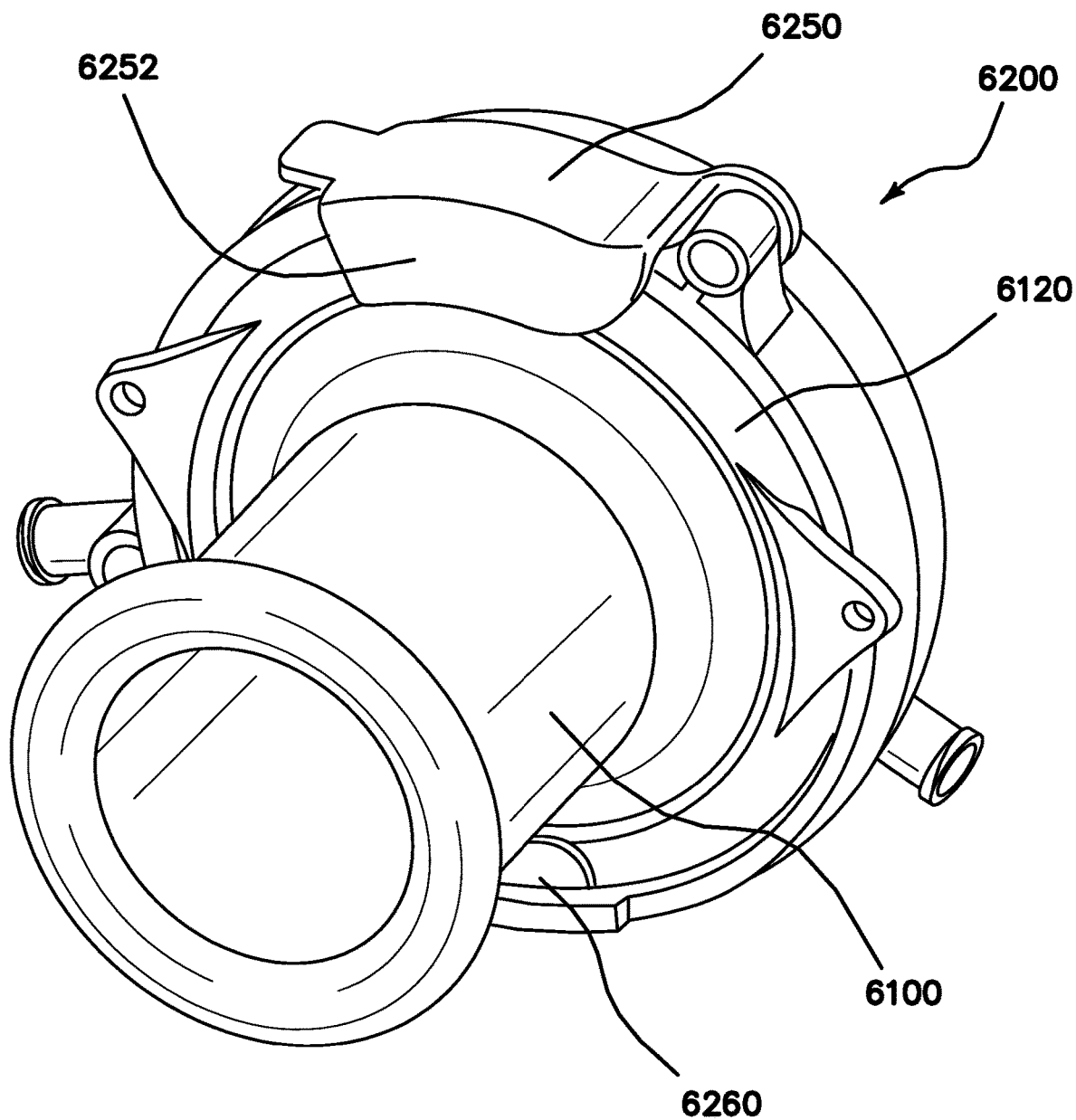
FIG. 8C is a perspective view of the natural orifice access device illustrated in FIG. 7A.

With reference to FIG. 8C, a perspective view of the natural orifice access device is illustrated. In the illustrated embodiment, the clamp 6250 can have a distal flange 6252 positioned to interface with the outer ring 6120 of the retractor when the clamp is in the clamped configuration. As illustrated, the clamp 6250 engages a distal surface of the outer ring 6120 of the retractor 6100. In some embodiments, the annular frame 6240 can further comprise at least one distal flange sized and positioned to interface with a retractor. In the illustrated embodiment, the annular frame 6240 comprises a distal flange 6260 positioned to engage a distal surface of the outer ring 6120 of the retractor. As illustrated, the flange 6260 is generally diametrically opposed to the distal flange of the clamp 6250. In other embodiments, the annular frame 6240 can include more than one distal flange positioned substantially equally spaced about the periphery of the annular frame 6240 or spaced irregularly about the periphery of the annular frame.

With reference to FIG. 9A, another embodiment of natural orifice access device is illustrated with a cap 6300 removably coupled to a retractor 6100 such as that described above with respect to FIGS. 6A-6C, 7A, 8A-8C, and 9A. In the illustrated embodiment, the cap 6300 includes multiple trocar access devices 6310 positioned through an access surface 6320 thereof. Advantageously, the multiple trocar access devices 6310 allow for easy placement and manipulation of multiple laparoscopic instruments in a surgical site through a single natural orifice.

In some embodiments, the inner ring 6110 and the outer ring 6120 independently have different footprint shapes and/or footprint diameters. For example, in the embodiment illustrated in the embodiment of retractor 7100 illustrated in FIGS. 6D-F, 7B, 8D, and 9B, the inner ring 7110 can be substantially flush with the tubular body 7130 while the outer ring 7120 can be an annular member having a generally circular cross-section. An inner ring 6110 with a larger diameter permits a greater retraction force, but is more difficult to insert and remove from a body cavity.

With reference to FIGS. 6D-6F, in some embodiments, a natural orifice access port or retractor 7100 can be adapted for use in a transanal endoscopic microsurgery (TEMS) procedure. The retractor 7100 comprises an inner or distal ring 7110, an outer or proximal ring 7120, a tubular body 7130, and a funnel segment 7140 extending between and coupling the inner ring 7110 and the outer ring 7120. The tubular body 7130 comprises a relatively flexible material such as a KRATON® material or a silicone rubber material, which is substantially cylindrical in the illustrated embodiment. In other embodiments, the tubular body 7130 has another shape, for example, an oval cross section. Some embodiments of the tubular body 7130 comprise one or more coatings that provide additional functionality, for example, an anti-microbial coating.

In the illustrated embodiment, the inner ring 7110 is substantially flush with a distal end of the tubular body 7130 such that the retractor 7100 has a generally tubular configuration extending distally of the funnel segment 7140 to the distal end. Embodiments of the inner ring 7110 are sufficiently flexible and compliant to be compressed and/or deformed for insertion into a body orifice such as a patient's anus during a transanal surgical procedure. When subsequently released within an associated body cavity, the inner ring 7110 substantially returns to its original shape or footprint. In some embodiments, the inner ring 7110 assumes a substantially circular shape substantially flush with the generally cylindrical tubular body 7130 in a relaxed state, for example, when released within a body cavity. In other embodiments, the inner ring 7110 has another shape in the relaxed state, for example, an oval. The inner ring 7110 assumes a different shape when compressed for insertion through an incision or body orifice, for example, a substantially oval shape, a generally linear shape, a tear-drop shape, or another suitable shape. In other embodiments, the inner ring 7110 is substantially rigid, that is, non-compliant under the ordinary conditions under which it is used.

With continued reference to FIGS. 6D-6F, in some embodiments, the inner ring 7110 can be shaped and configured to facilitate insertion through a natural orifice. For example, in the illustrated embodiment, the inner ring 7110 can include a radiused edge to facilitate atraumatic entry through a natural orifice. In other embodiments, the inner ring 7110 can include a beveled edge to facilitate entry through a natural orifice. Furthermore, in the illustrated embodiment, the inner ring 7110 can be formed at an angle transverse to a longitudinal axis defined by the tubular body

7130. Advantageously, such an angled inner ring 7110 can facilitate insertion of the retractor 7100 through a natural orifice. In other embodiments, the inner ring 7110 can be substantially perpendicular to the longitudinal axis defined by the tubular body.

With continued reference to FIGS. 6D-6F, the outer ring 7120 is proximal the funnel section 7140. In the illustrated embodiment, the outer ring 7120 has a substantially circular footprint. As further discussed herein, the outer ring 7120 can be sized and configured to sealingly couple to a cap or other access device thereon. In some embodiments, as discussed above with reference to the embodiments of FIGS. 6A-6C, one or more suture points can be disposed on the retractor 7100 adjacent the outer ring 7120.

With continued reference to FIGS. 6D-6F, the tubular body 7130 can have a generally circular profile defining a generally cylindrical passage 7150. The generally cylindrical passage 7150 is desirably large enough to accommodate more than one laparoscopic instrument there through such that a single natural orifice access device can be used to provide access for multiple surgical instruments in a body cavity. Moreover, generally cylindrical passage 7150 is desirably large enough such that multiple surgical instruments positioned there through can be translated or pivoted relative to one another, allowing a surgeon to manipulate the instruments as desired during a surgical procedure. The generally cylindrical passage extends between a proximal end 7152 of the retractor 7100 adjacent the outer ring 7120 to a distal end 7154 of the retractor 7100 adjacent the inner ring 7110 (FIG. 6D).

With reference to FIG. 6D, in the illustrated embodiment, the funnel segment 7140 provides a diametric reduction between the relatively large diameter of the outer ring 7120, which is sized and configured to be removably coupled to an access device such as a cap, and the relatively smaller diameter of the passage 7150, which is sized to fit within a natural orifice with minimal distention of the orifice. The funnel segment 7140 has an inner surface 7142 which can provide a bearing surface for an obturator used to advance to the retractor 7100 into a body cavity. In some embodiments, the funnel segment 7140 can have a substantially linear taper between the relatively large diameter and the relatively smaller diameter such that the inner surface 7142 is a frusto-conical segment. In other embodiments, the funnel segment 7140 can have a curved profile between the relatively large diameter and the relatively smaller diameter.

In some embodiments, a natural orifice access system can include a retractor 7100 and an optional obturator, such as described above with reference to FIG. 6G. The obturator can have a proximal bearing surface 6410 sized and configured to bear against the inner surface 7142 of the funnel segment 7140 and a distal dilation surface 6420 sized and configured to expand a natural orifice for passage of the retractor 7100. Thus, during insertion of the retractor 7100 into a natural orifice, the dilation surface expands a pathway to a surgical site in a body cavity while the obturator bears on the inner surface 7142 of the funnel segment 7140 to advance the retractor 7100 into position in the surgical site. Furthermore, in some embodiments, the obturator can have a handle 6430 at a proximal end thereof adapted to facilitate selective twisting or rotation of the obturator about a longitudinal axis thereof during insertion.

Figure 6I:
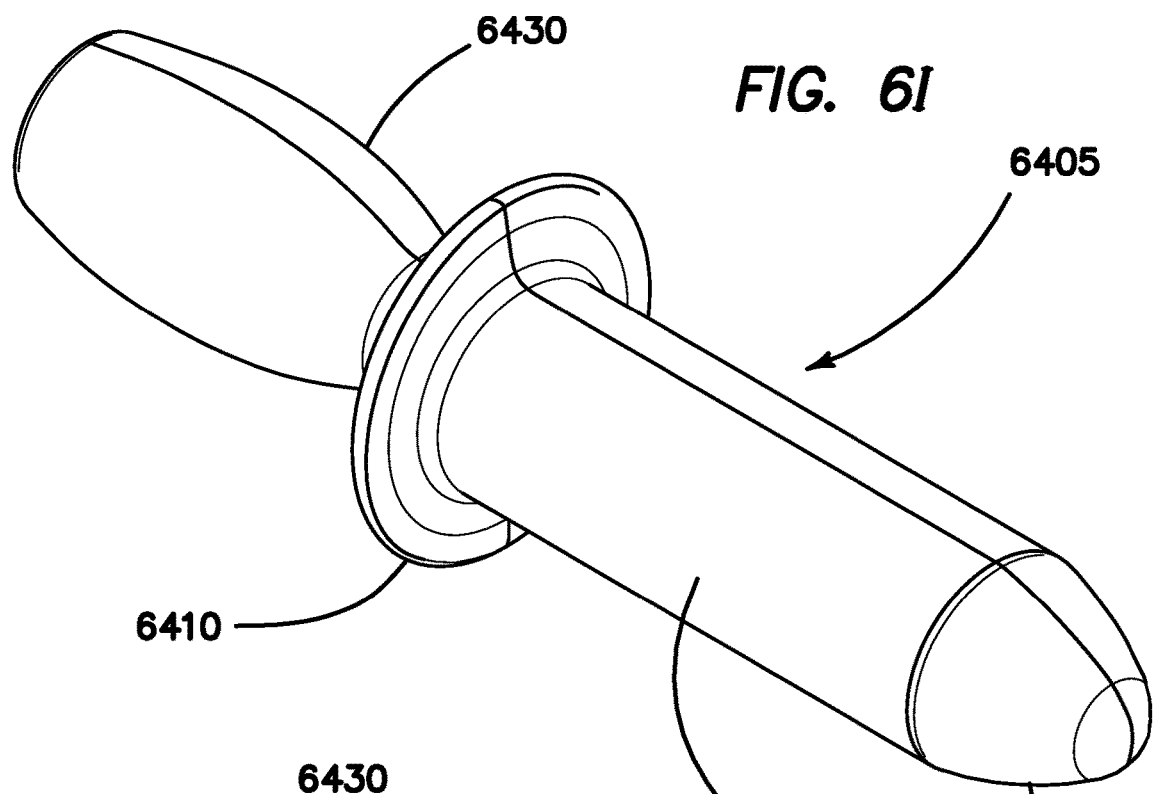
FIG. 6I is a perspective view of an obturator having a straight shaft piece, adapted to facilitate introduction of a natural orifice retractor into a body orifice such as an anus.
Figure 6J:
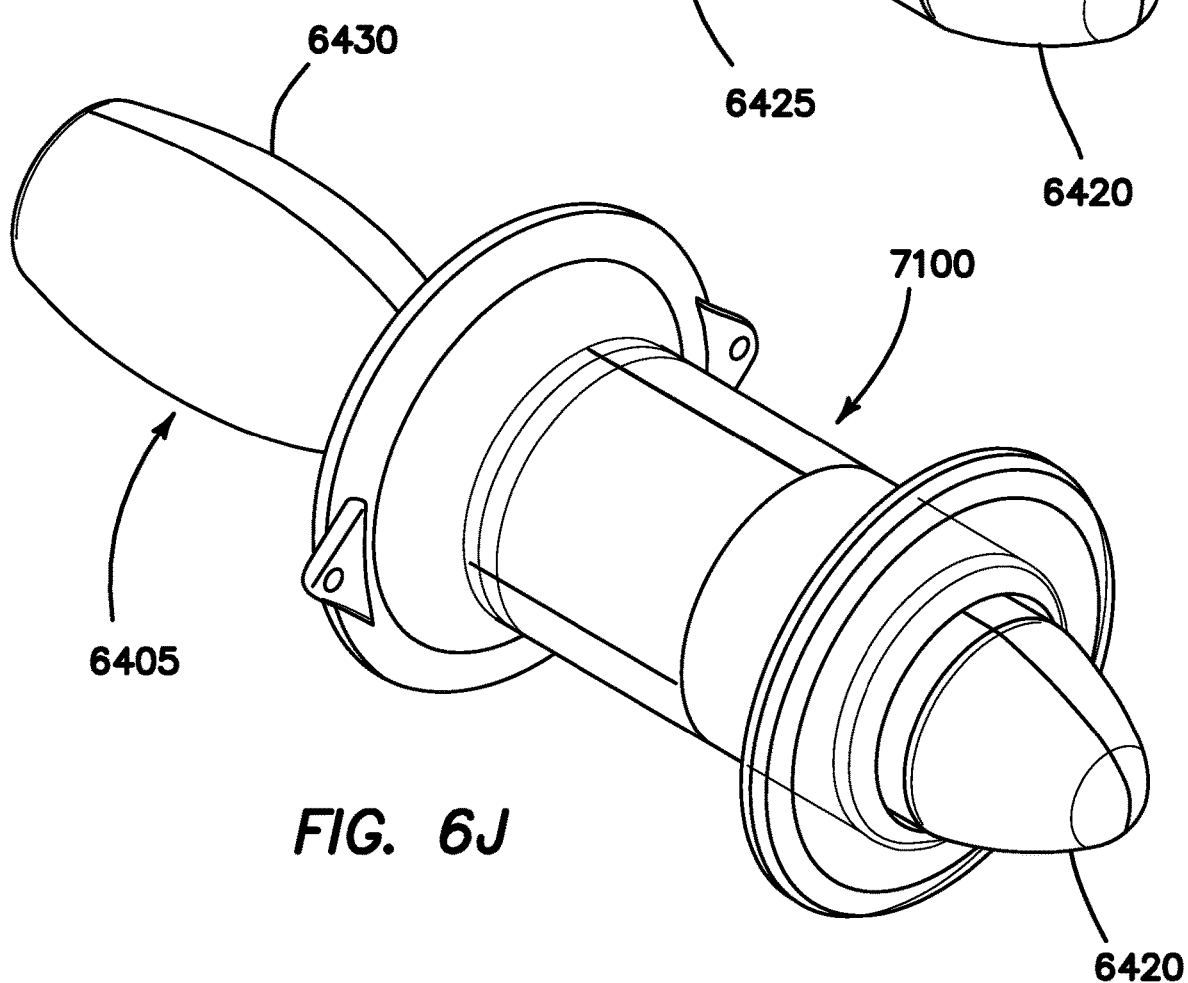
FIG. 6J is a perspective view of a retractor disposed on the obturator of FIG. 6I.

In an alternative embodiment, shown in FIG. 6I, the obturator 6405 includes a straight shaft piece 6425 between the distal dilation surface 6420 and the proximal bearing surface 6410 that facilitates dilation of the natural orifice prior to inserting the retractor. It can then be combined with the retractor 7100 to help ease insertion, as shown in FIG. 6J.

With reference to FIG. 7B, it can be desirable that the outer ring 7120 is relatively stiff compared with the relatively flexible tubular body 7130 of the retractor 7100 so that the outer ring 7120 can sealingly engage an access device such as a cap. In the illustrated embodiment, the retractor 7100 is formed in a multiple-shot molding process. For example, in the illustrated embodiment, an inner segment of the retractor 7100 defined by the tubular body 7130 and the inner ring 7110 is formed in one molding operation from a flexible material, and an outer segment of the retractor 7100 defined by the funnel segment 7140 and the outer ring 7120 is formed in another molding operation from a relatively rigid material such as a polycarbonate material or other suitable material.

In other embodiments, a multiple-shot molding process can be varied such that the resulting inner and outer segments are different from those of the illustrated embodiment. For example, in certain embodiments, the inner segment can include the tubular body 7130, the inner ring 7110, and a portion of the funnel segment 7140, while the outer segment can include a portion of the funnel segment 7140 and the outer ring 7120. In certain other embodiments, the inner segment can include the inner ring 7110 and a portion of the tubular body 7130, while the outer segment can include a portion of the tubular body 7130, the funnel segment 7140, and the outer ring 7120.

With reference to FIGS. 6D and 7B, a retractor 7100 formed in a multiple-shot molding process can include one or more retention members 7160 on the inner segment and the outer segment to maintain the position of the inner segment relative to the outer segment. For example, in some embodiments, a distal end of the outer segment can include one or more protrusions 7162 extending radially outwardly from the funnel segment 7140 and one or more recesses 7164 recessed radially inwardly from the funnel segment 7140 at an interface region of the inner segment and the outer segment of the retractor 7100. In the illustrated embodiment, the distal end of the outer segment includes a plurality of protrusions 7162 alternating with a plurality of recesses 7164 there between. Moreover, in some embodiments, the outer segment can include an annular groove 7170 formed in the funnel segment 7140 at an interface region of the inner segment and the outer segment of the retractor 7100. The inner segment of the retractor 7100 can include an annular member 7166 disposed within and matingly engaging the groove 7170 to maintain the position of the inner segment relative to the outer segment.

With reference to FIG. 7B, a cross-sectional view of retractor 7100 is shown. In the illustrated embodiment, the tubular body 7130 is formed of a flexible material having a predetermined fixed length L2, inner diameter D2, and wall thickness T2. The fixed length L2, inner diameter D2, and wall thickness T2 are selected to accommodate the anatomy of a natural orifice, such as the anal orifice of a majority of patients. It is contemplated that the retractor 7100 can be scaled to different sizes for patients of different ages. Furthermore, in some embodiments, it is contemplated that the retractor can include a telescopic tubular body such that the tubular body can be selectively positioned at a variety of lengths depending on patient anatomy and the location of the surgical site within the body cavity. Desirably, the wall thickness T2 and material of the tubular body 7130 are selected such that the tubular body 7130 is resilient enough to maintain the passage 7150 there through when positioned in the natural orifice. Moreover, desirably, the inner diameter, D2 is sufficiently large to accommodate multiple surgical instruments. For example, in embodiments of the retractor 7100 adapted for use in a transanal surgical procedure, the inner diameter D2 and thickness T2 can be sized such that an outer diameter of the retractor can be between approximately 30 mm and 70 mm, desirably between approximately 35 mm and 50 mm, and in one embodiment approximately 40 mm. Additionally, desirably, the fixed length L2 is sufficiently long such that the inner ring 7110 can be positioned at a surgical site within a body cavity and the outer ring 7120 can be positioned outside the natural orifice. In some embodiments, the fixed length L2 is of a length such that the device has an overall length between the proximal end 7152 and the distal end 7154 of between approximately 100 mm and approximately 200 mm, desirably between approximately 120 mm and 180 mm, more desirably between approximately 140 mm and 160 mm, and in one embodiment, approximately 150 mm.

Figure 8D:
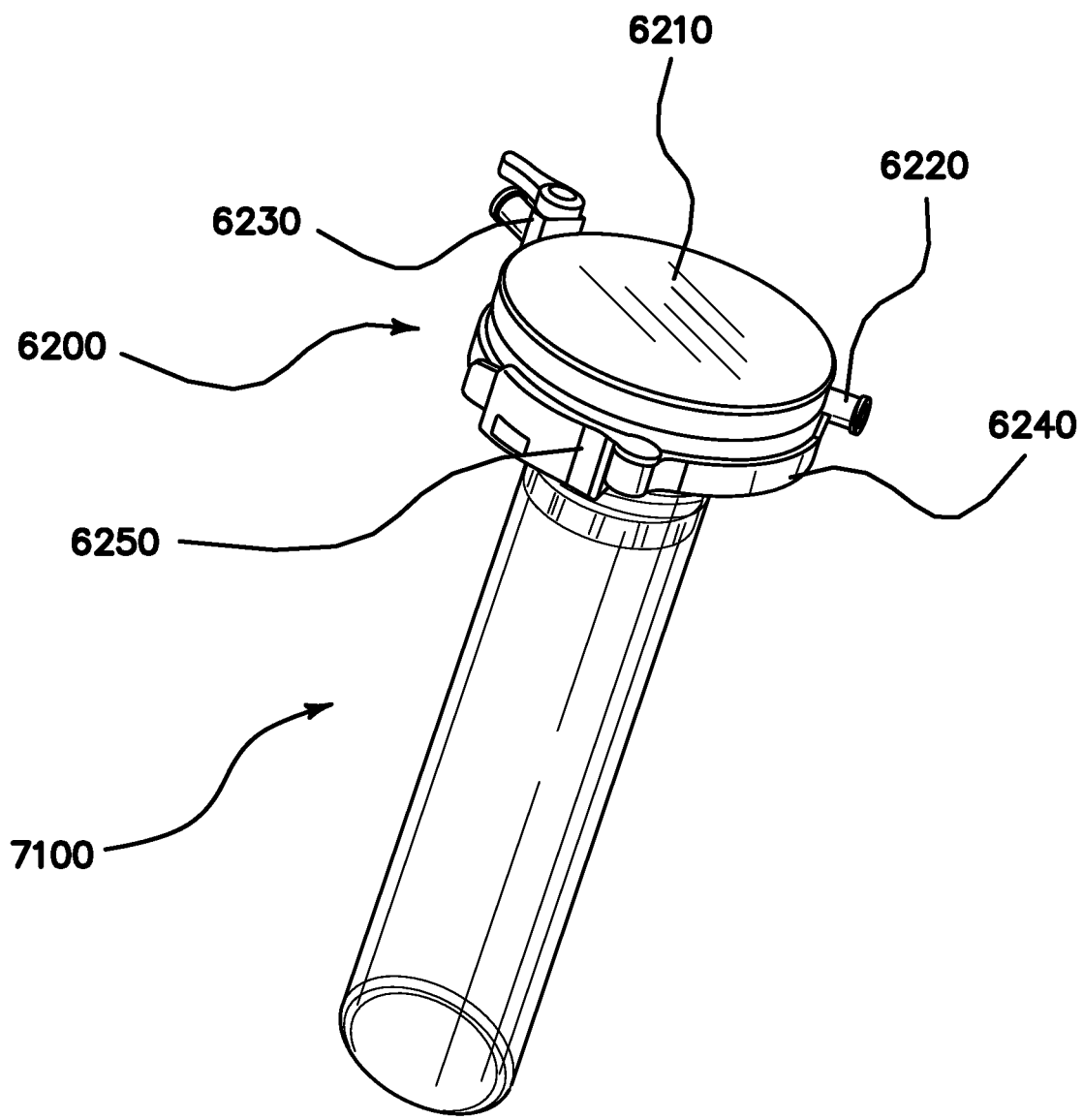
FIG. 8D is a perspective view of the natural orifice retractor of FIG. 6D with a gel cap therewith to form one embodiment of natural orifice access device.

With reference to FIG. 8D, a perspective view of a natural orifice access device having a cap 6200 substantially similar to that described with respect to FIGS. 8A-8C removably coupled to a retractor 7100 is illustrated. In the illustrated embodiment, the cap 6200 comprises a sealable access surface 6210 such as a gel pad surface as described in further detail herein. In certain embodiments, the cap 6200 can also comprise at least one gas or fluid port 6220, 6230. In the illustrated embodiment, the cap 6200 comprises two gas or fluid ports 6220, 6230, such that one port can be used for gas insufflation and the other port can be used for ventilation for example when electrosurgery is performed through the access device. In certain embodiments, at least one of the gas or fluid ports 6220, 6230 comprises a valve such as a stopcock valve to selectively control the flow of fluid there through.

With continued reference to FIG. 8D, a top view of the natural orifice access device is illustrated. The sealable access surface 6210 can be encircled by and restrained by an annular frame 6240 such as a split ring having a clamp 6250. The clamp 6250 can be movable between an open configuration in which the cap 6200 is selectively removable from the retractor 7100 and a clamped configuration in which the cap 6200 can be secured to the retractor 7100. For example, the annular frame 6240 can be positioned peripherally around the outer ring 7120 with the clamp 6250 in the open configuration and the clamp moved to the clamped configuration to sealingly fix the cap 6200 to the retractor 7100. Accordingly, the cap 6200 can be easily removed during a surgical procedure to facilitate removal of excised tissue from a surgical site through the retractor 7100.

Figure 9A:
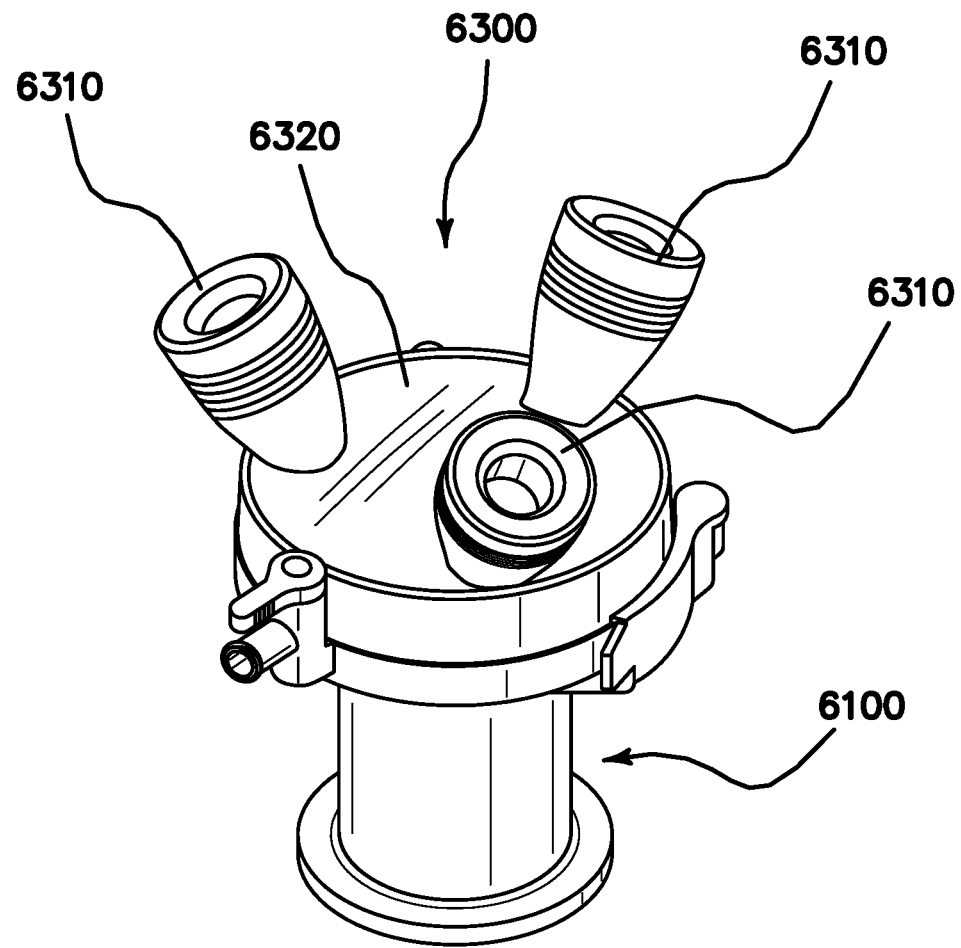
Figure 9B:
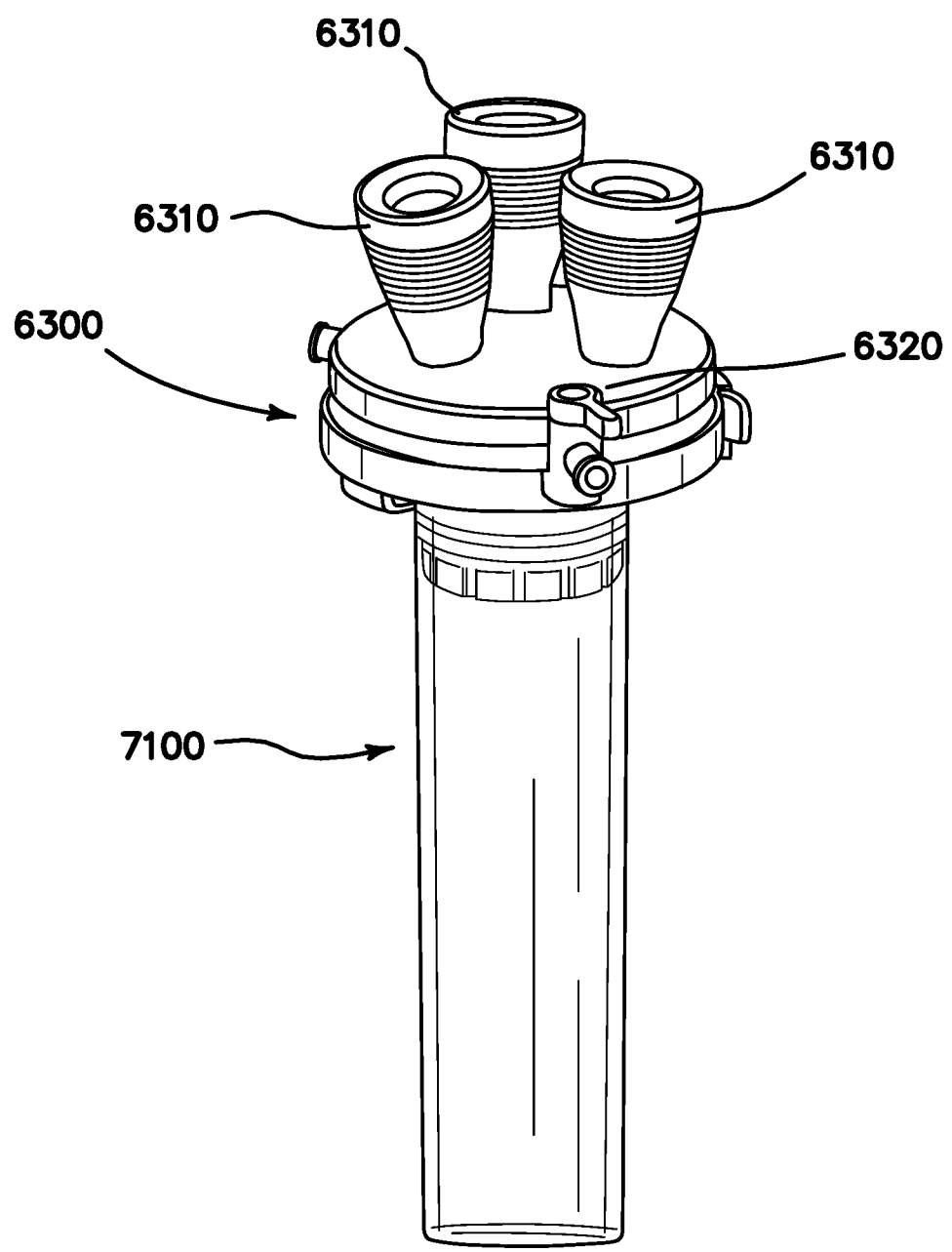

With reference to FIG. 9B, another embodiment of natural orifice access device is illustrated can include a cap 6300 substantially similar to that described above with reference to FIG. 9A removably coupled to a retractor 7100 such as that described above with respect to FIGS. 6D-F, 7B, and 8D. The cap 6300 can include multiple trocar access devices 6310 positioned through an access surface 6320 thereof. Advantageously, the multiple trocar access devices 6310 allow for easy placement and manipulation of multiple laparoscopic instruments in a surgical site through a single natural orifice.

As discussed herein, the retractors shown in FIGS. 7A and 7B can include a telescopic tubular body such that the tubular body can be selectively positioned at a variety of lengths depending on patient anatomy and the location of the surgical site within the body cavity. In another embodiment, illustrated in FIG. 7C, the tubular body may be formed in sections of varying length that slidingly engage and snap lock together to provide a variety of lengths, depending of the number and size of the sections selected and assembled. With reference to FIG. 7C, a perspective view of a retractor 6500 is shown having three sections: an outer ring section 6510, an inner ring section 6520, and an intermediate section 6530 disposed between the other two sections. The three sections are held together by a snap lock mechanism 6540. Each section terminates at the distal end with an annular groove 6550 that slidingly engages with the proximal end 6560 of the next section, best shown in the cross section view of FIG. 7D. The snap lock mechanism is shown in cross-section in FIG. 7E. The tubular body of the embodiment shown in FIG. 7C-E is preferably formed from a relatively stiff material, such as a polycarbonate.

Optionally, as shown in FIG. 7C-7F, the tubular body of the retractor can include cut-out portions or windows 6570, to provide access to regions of the anatomy that would otherwise be obscured by the tubular body while the retractor is in place. Thus, the retractor can be inserted into the body orifice or incision to provide retraction and to protect the lining of the body cavity, and then manipulated to align the window(s) to the sites of interest in the body cavity for access by surgical instruments.

Figure 7M:
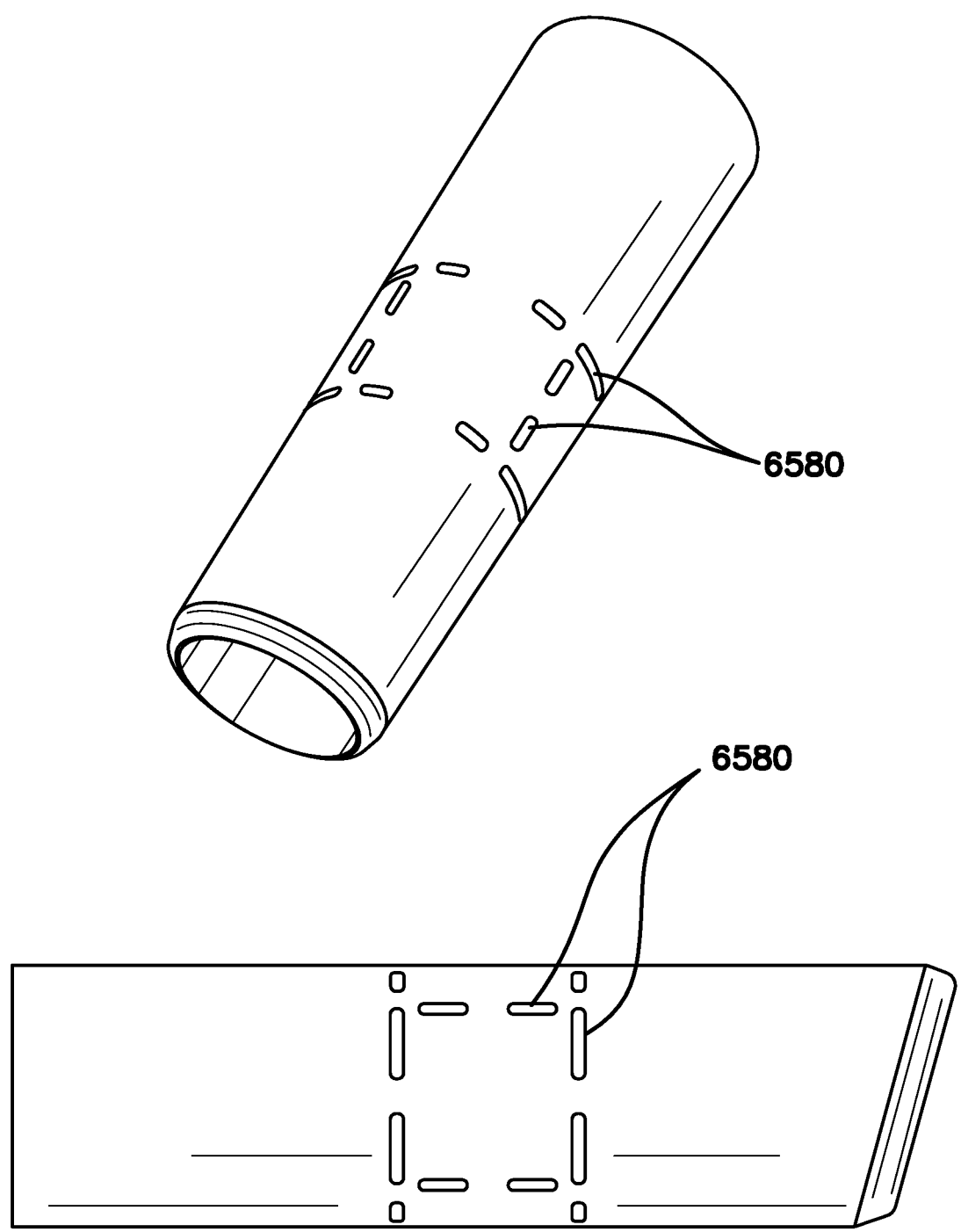
FIG. 7M is a perspective view and a side view of a perforated natural orifice retractor.

As will be appreciated, such cut-out portions may be provided in retractors having tubular bodies of both rigid and flexible construction, as well as tubular bodies formed as a single piece or in sections. FIG. 7M shows an example of a flexible tubular body of a retractor, both in side view and in perspective view, wherein the tubular body contains perforations 6580. The tubular body can be cut or torn at the perforations to vary the length of the tubular body and/or to incorporate cut-out portions into the tubular body. The tubular body of the embodiment shown in FIG. 7M is preferably formed from a relatively flexible material, such as KRATON® or PELLETHANE®.

In the illustrated embodiments of FIGS. 9A and 9B, the trocar access devices 6310 have a relatively low profile, that is, protrude minimally above the access surface 6320 and/or below the distal surface of the cap 6300. Accordingly, the trocar access devices 6310 are shorter than a length of a typical trocar and comprise a seal assembly positioned above the access surface 6320 and a cannula extending through the gel pad of the cap 6300. The reduced length of the trocar access devices 6310 allows increased angular or pivotal motion for instruments extending there through, and also permits the use of curved and/or angled instruments.

Figure 9C:
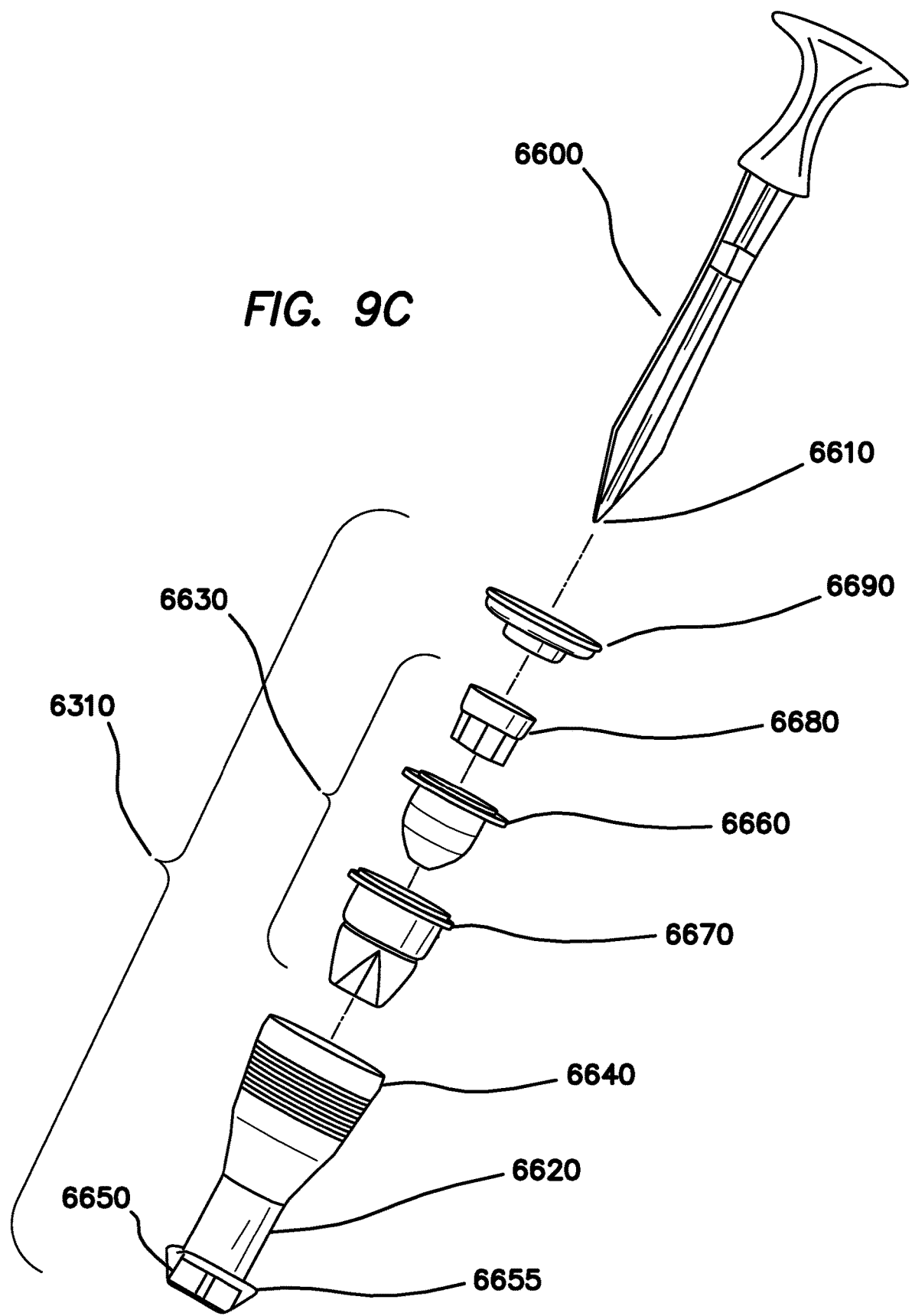
FIG. 9C is an exploded view of an embodiment of a trocar access device and optional obturator, which is a component of some embodiments of the access device system.

FIG. 9C is an exploded view of an embodiment of a trocar access device 6310 and optional obturator 6600, which is a component of some embodiments of the access device system. In the illustrated embodiment, the obturator 6600 comprises a pointed, puncture tip 6610.

The trocar access device 6310 comprises a proximal end, a distal end, and a longitudinal axis. The trocar access device 6310 comprises a cannula 6620 extending along the longitudinal axis. A trocar seal 6630 is disposed at the proximal end of the cannula 6620, contained within a housing 6640. A retainer 6650 is disposed at the distal end or tip of the cannula 6620.

The cannula 6620 comprises a tubular body dimensioned to accommodate an instrument or instruments received there through. In the illustrated embodiment, the cannula 6620 is a substantially cylindrical tube, and extends through the cap 6300 in use. In the illustrated embodiment, the cannula 6620 is comparatively short because the cannula need only traverse the cap 6300 (FIG. 9A-B), which has a known and consistent thickness, rather than a body wall. Accordingly, some embodiments of the cannula 6620 are not more than about 2-times longer, about 1.5-times longer, about 1.2-times longer, or about 1.1-times longer than the thickness of the gel pad. In some embodiments, the cannula 6620 is less than about 20 mm, about 10 mm, or about 5 mm longer than the thickness of the gel pad. In some embodiments, the cannula 6620 is about as long as the gel pad is thick. In other embodiments, the cannula 6620 has a different length, for example, a length typical for a cannula used for traversing a body wall. Shorter length cannula permit increased angular degrees of freedom for instruments passing there through. Embodiments of shorter cannula also accommodate curved instruments. The cannula 6620 comprises any suitable biocompatible material. In some embodiments, the cannula 6620 comprises a flexible material.

The illustrated trocar seal 6630 comprises an instrument or septum seal 6660 and a zero seal 6670. Optionally, a shield 6680 may be disposed within the instrument seal 6660. The instrument seal 6660 seals instruments passing there through, thereby maintaining pressurization in a body cavity such as pneumoperitoneum or pneumorectum. The zero seal 6670 provides a seal when no instrument passes through the trocar seal 6630. The instrument seal 6660 and zero seal 6670 are received in a housing 6640 disposed at the proximal end of the cannula 6620 and secured therein by a seal cover 6690.

The retainer 6650 is disposed at or near the distal end of the cannula 6620. In some embodiments, the retainer 6650 and cannula 6630 are integrated, while in other embodiments, the retainer 6650 and cannula 6630 are not integrated. In the illustrated embodiment, the proximal end of the retainer 6650 comprises a flange 6655 that is generally flat and perpendicular to the longitudinal axis, while the distal end is tapered, narrowing toward the distal end of the cannula 6620. The flange 6655 reduces the likelihood of accidental or inadvertent removal of the trocar access device 6310 from the cap. Some embodiments of the proximal face of the flange 6655 comprise additional anchoring features, for example, at least one of barbs, spikes, ridges, texturing, and the like, which are configured to penetrate or bite into a distal face of the cap 6300. In some embodiments, a diameter of the flange 6655 is from about 1.2 to about 2.5 times wider, or from about 1.5 to about 2.0 times wider than an outer diameter of the cannula 6630. Some embodiments of the trocar access device 6310 are 5-mm trocars, in which the outer diameter of the cannula 6620 is from about 7 mm to about 8 mm.

The tapered end of the retainer 6650 facilitates insertion of the trocar access device 6310 through the cap, either by itself, or when assembled with the obturator 6600 extending there through. For example, in some embodiments, the retainer 6650 is inserted through a preformed opening in the cap 6300.

In some embodiments in which the retainer 6650 and cannula 6620 are not integrated, that is, are separate components, the retainer 6650 is secured to the cannula 6620 after the cannula 6620 is inserted through the cap. In some embodiments, the cannula 6620 and retainer 6650 are secured mechanically, for example, using latches, screw threads, clips, lock rings, ratchets, and the like. In some embodiments, the cannula 6620 and retainer 6650 are secured adhesively. In some embodiments, the position of the retainer 6650 is adjustable, for example, to accommodate caps of different thicknesses. In some embodiments, the cannula 6620 and/or retainer 6650 is secured to the cap, for example, adhesively.

Figure 4:
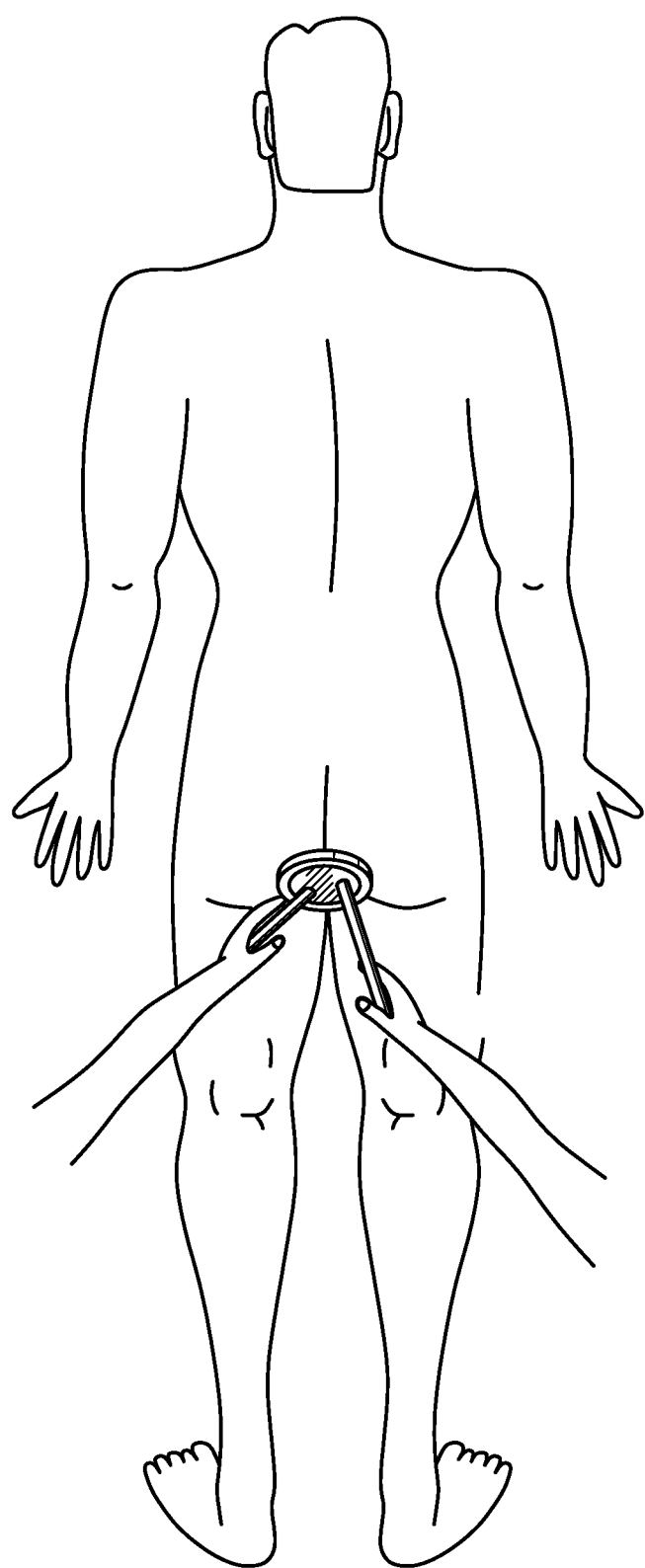
FIG. 4 is a top view illustrated a patient in the prone position with an embodiment of the access device deployed and in use at the anus of the patient.

An embodiment of a procedure for retracting a body orifice is described with reference to the embodiments of the retractor 6100 illustrated in FIGS. 6A-6C, 7A, 8A-8C, and 9A, and the embodiments of retractor 7100 illustrated in FIGS. 6D-6F, 7B, 8D, and 9B, although the procedure is applicable to all of the embodiments of the retractor disclosed herein. In use, the surgical wound retractor 6100, 7100 is inserted into a body orifice, such as the vagina (FIG. 2), mouth (FIG. 3) or anus (FIG. 4). The inner ring 6110, 7110 is folded or compressed into an oval or other suitable shape and urged through the incision or body orifice into an associated body cavity. Once the inner ring 6110, 7110 is fully disposed within the associated body cavity, it is allowed to resume its original, relaxed shape, for example, substantially circular, oval, or other original shape. In some embodiments, the inner ring 6110 is then pulled upward against the inner surface of the body cavity, for example, by pulling the outer ring 6120 upward. An outer surface of the tubular body 6130, 7130 retracts the natural orifice.

As illustrated in FIG. 5, some embodiments of the access device 5000 comprise a cap, cover, or lid 5500 coupled to the outer ring of the retractor 5100, which seals the retractor 5100, for example, for maintaining pressurization within a body cavity such as pneumoperitoneum or pneumorectum. In some embodiments, lid 5500 is removable, for example to provide access into the body cavity. Some embodiments of the lid 5500 comprise a transparent or translucent portion, thereby allowing a user to view into the body cavity without removing the lid 5500. As will be described below, one embodiment of a lid 5500 is a gel cap. In some embodiments, a cross-sectional shape of the outer ring 6120 (FIG. 6A), 7120 (FIG. 6D) of the retractor is selected to reduce or prevent the lid 5500 from partial and/or incorrect coupling to the outer ring 6110 (FIG. 6A), 7120 (FIG. 6D) of the wound retractor. Such cross-sectional shapes include oval and rectangular, or any other suitable cross-sectional shape that provides the desired functionality, for example, hexagonal, octagonal, and the like. Additionally, depending on the use and on surgeon preference, in some embodiments, each of the inner ring 6110, 7110 and outer ring 6120, 7120 of the wound retractor includes independently variable design configurations. For example, embodiments of the inner ring 6110, 7110 and/or the outer ring 6120, 7120 are rigid or flexible, and have footprints, cross-sectional shapes, and/or dimensions dependent on the intended use, for example, circular or oval footprints, diameters dependent on incision or orifice dimensions, or cross-sectional dimensions dependent on retraction force. In some embodiments, the inner ring 6100 may extend radially out from the tubular body 6130 when deployed, stabilizing the retractor within the body orifice (FIG. 7A). In other embodiments, the inner ring 7110 may be flush with the tubular body 7130, as where, for example, the length L2 of the tubular body is sufficient to stabilize the retractor within the body orifice (FIG. 7B).

Figure 10A:
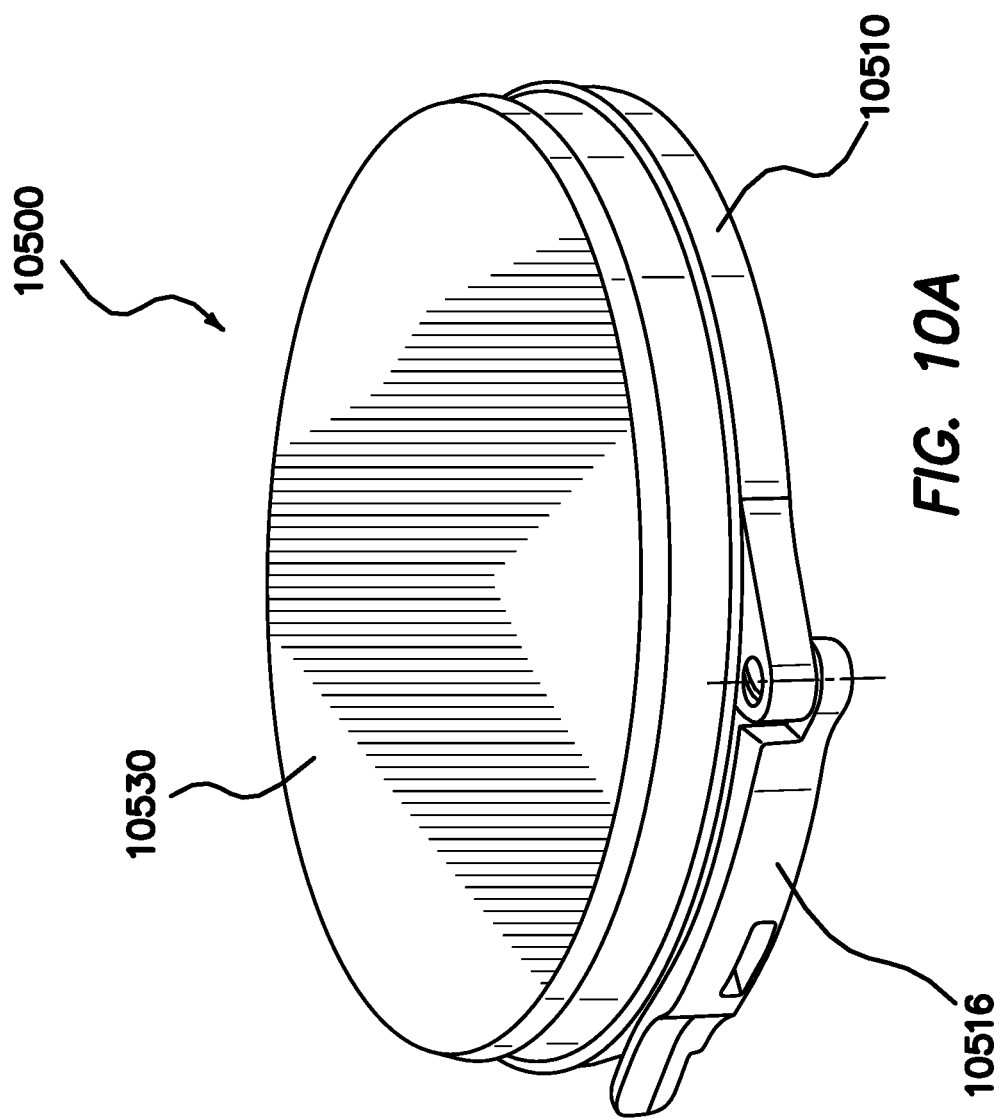
FIG. 10A is a top perspective view of an embodiment of a gel cap.

FIG. 10A illustrates in perspective an embodiment of a cap or cover 10500, which is a surgical access device that seals the opening between the body cavity and the area outside the body cavity while providing access into the body cavity from outside the body cavity. More particularly, the illustrated cap 10500 releasably and sealingly couples to the outer ring 6120 (FIG. 6A), 7120 (FIG. 6D) of the wound retractor. The cap 10500 comprises a cap ring 10510 dimensioned and configured for coupling to the outer ring 6120, 7120 of the wound retractor and a pad 10530 coupled to the cap ring 10510. Embodiments of the cap 10500 provide an artificial body wall with consistent properties compared with a natural body wall, for example, thickness, compliance, rigidity, uniformity, and the like.

The illustrated cap or cover 10500 is substantially circular. In other embodiment, the gel cap 10500 has another shape or footprint, for example, oval, elliptical, parabolic, square, rectangular, or another suitable curved or polygonal shape. In some embodiments, the outer ring 6120, 7120 of the retractor and cap ring 10510 of the cap have the same general shape or footprint. In other embodiments, the outer ring 6120, 7120 of the retractor and cap ring 10501 of the cap have substantially different shapes, for example, a generally circular outer ring 6120, 7120 and an oval cap ring 10510. In these embodiments, the outer ring 6120, 7120 is distorted or reshaped for coupling to the cap ring 10510, for example, by compressing opposed sides of the outer ring 6120, 7120. Non-circular shapes are useful, for example, for procedures in which space is limited. As discussed above, retracting a long, straight incision using an oval or elongated retractor requires less force than a similar procedure using a circular retractor.

In some embodiments, the pad 10530 comprises a gel. In such embodiments, the pad 10530 is referred to as a "gel pad" and the cap 10500 is referred to as a "gel cap". Descriptions of gel pads and gel caps generally apply to embodiments in which the pad 10530 does not comprise gel unless otherwise specified. In some embodiments, the gel pad 10530 does not comprise any preformed access channels there through, for example, for instrument access. Instruments may be inserted directly through the gel pad 10530, puncturing the gel pad 10530, and thereby creating access channels or portions in the gel pad 10530. Each access portion forms an instrument seal in the presence of an instrument inserted there through and a zero seal in the absence of an instrument inserted there through. The gel provides a gas tight seal around a variety of shapes and sizes of instruments inserted there through. Some embodiments of the gel pad 10530 also provide trocar access directly there through, which also provide instrument access into the body cavity. Embodiments of the gel pad 10530 have a working diameter of from about 40 mm to about 120 mm, which is the diameter of a portion of the gel pad 10530 through which instruments and/or trocars may be inserted. Embodiments of the gel cap 10500 are typically from about 10 mm to 50 mm wider than the working diameter.

Accordingly, embodiments of the gel cap 10500 maintain pressurization within a body cavity such as pneumoperitoneum or pneumorectum during multiple instrument exchanges and substantially prevent unintentional loss of pressurization. Embodiments of the gel cap 10500 also provide substantially continuous access and visibility during surgery. Embodiments of the gel cap 10500 have a small profile for use in procedures with limited surgical space.

In some embodiments, the gel is an ultragel, which is characterized by an ultimate elongation greater than about 1000 percent and a durometer less than about 5 Shore A. Some embodiments of the ultragel comprising KRATON® and mineral oil exhibit an ultimate elongation exceeding about 1500 percent and improved sealing properties, for example, sealing with instruments of a wider size range than other seal materials. In some embodiments, the seals comprising ultragels also form zero seals when the instrument is removed therefrom. Accordingly, in some embodiments of seals comprising ultragels, a single seal is acts as both the instrument seal as well as the zero seal.

Figure 10B:
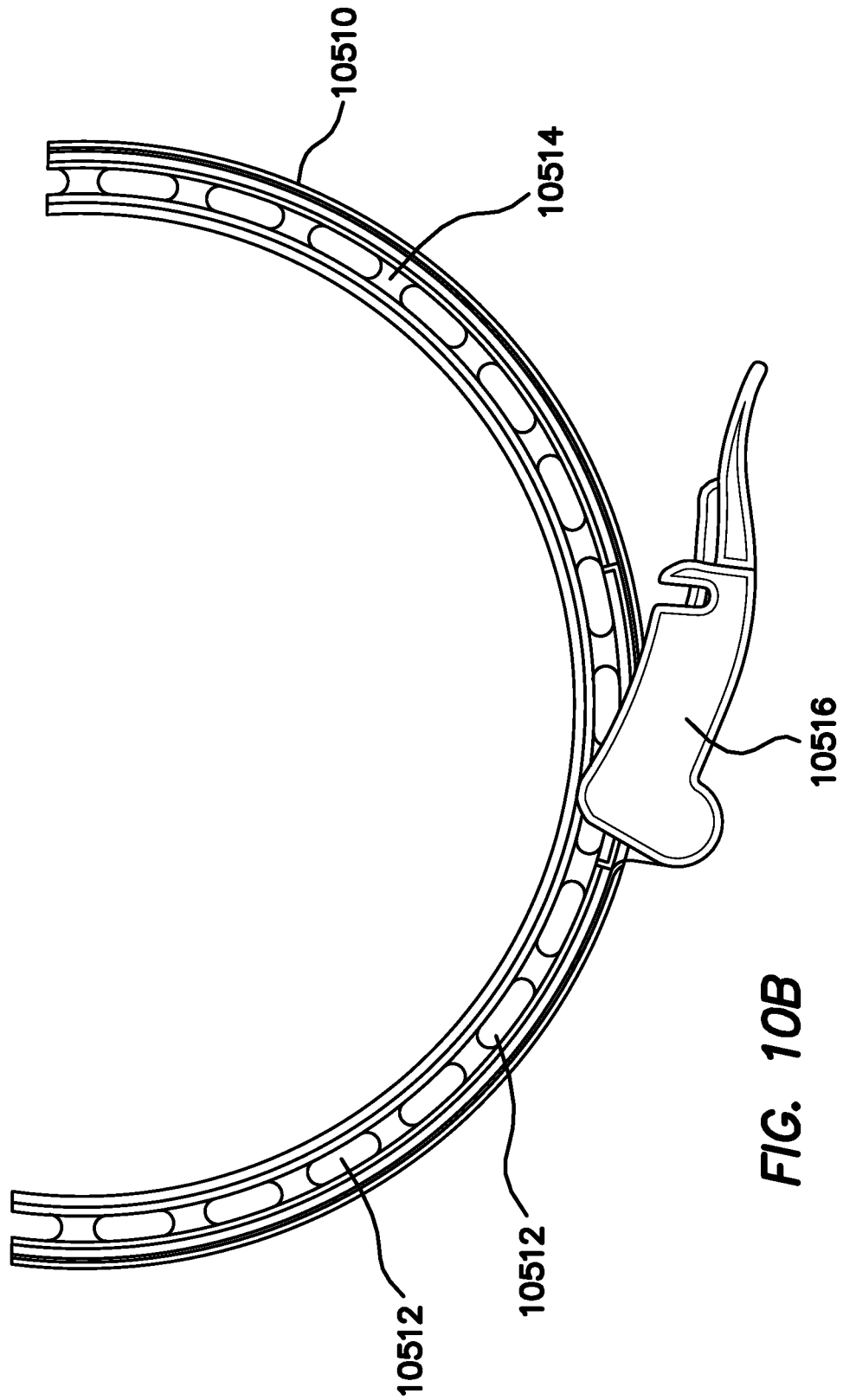
FIG. 10B is a bottom view of an embodiment of a cap ring.

Some embodiments of the cap ring 10510 comprise a substantially cylindrical ring comprising a proximal portion, a distal portion, and a longitudinal axis extending from the proximal portion to distal portions. In other embodiments, the cap ring 10510 has another shape or footprint, for example, oval. As best seen in FIG. 10B, which is a bottom view of a cap ring 10510, in the illustrated embodiment, the proximal portion of the cap ring 10510 comprises a plurality of apertures 10512 distributed about the periphery thereof. The apertures 10512 extend through a wall 10514 at the proximal portion of the cap ring. In other embodiments, the apertures 10512 are disposed in at least one member extending either longitudinally inward or longitudinally outward from the wall 10514 of the cap ring. The gel pad 10530 is disposed at the proximal portion of the cap ring 10510 in the illustrated embodiment, with portions of the gel pad 10530 extending through the apertures 10512, thereby creating an interlocking structure between the cap ring 10510 and the gel pad 10530, mechanically locking the cap ring 10510 and the gel pad 10530 together.

The distal portion of the cap ring 10510 is substantially cylindrical in the illustrated embodiment, and is dimensioned and configured to receive the outer ring 6120 (FIG. 6A), 7120 (FIG. 6D) of the wound retractor. The cap ring 10510 comprises a latch mechanism 10516 that removably couples the cap ring 10510 to the outer ring 6120, 7120. Those skilled in the art will understand that other mechanisms are also useful for coupling the cap ring 10510 to the outer ring 6120, 7120 of the wound retractor, for example, protruding lips, levers, clips, latches, tongues, grooves, screw threads, bayonet mounts, screws, friction fittings, compression fitting, snap caps, and the like. In the illustrated embodiment, when the outer ring 6120, 7120 of the wound retractor is received in the distal portion of the cap ring 10510, the outer ring 6120, 7120 of the wound retractor contacts and embeds within a portion of the gel pad 10530 disposed at the distal portion of the cap ring 10510, thereby displacing a portion of the gel, and forming a seal between the gel pad 10530, and the outer ring 6120, 7120 and tubular body 6130, 7130 of the wound retractor. Thus, the distal portion of the gel pad 10530 is in juxtaposition with the incision or body orifice. In other embodiments, the cap ring 10510 is permanently coupled or fixed to the outer ring 6120, 7120.

The cap ring 10510 in some embodiments comprises a polymer. Examples of suitable polymers include, at least one of polyethylene (PE), low density polyethylene (LDPE), high density polyethylene (HDPE), ultra high molecular weight polyethylene (UHMWPE), polycarbonate, thermoplastic elastomers (DYNAFLEX®, GLS Corp.; KRATON®, Kraton Polymers), polyphenylene oxide (PPO), polystyrene, and the like. The polymer component of the cap ring is fabricated by any suitable method, including injection molding, melt casting, blow molding, and the like.

Some embodiments of a process in which the gel pad 10530 is cast in the cap ring 10510 are include steps performed at temperatures above about 130° C. over several hours, for example, from about three (3) to about four (4) hours. Accordingly, in some of these embodiments, the cap ring 10510 does not deform under these conditions.

Some embodiments of the gel pad 10530 comprise an elastomeric gel. Examples of such gels are described in U.S. patent application Ser. No. 10/381,220, filed Mar. 20, 2003, the disclosure of which is hereby incorporated by reference as if set forth in full herein. Embodiments of the gel are prepared by mixing at least one triblock copolymer with a solvent that dissolves the midblocks of the triblock copolymer. The mixture is typically a slurry. The endblocks typically comprise a thermoplastic material, such as styrene, while the midblocks typically comprise a thermoset elastomer such as, ethylene/butylene, isoprene, or butadiene. Examples of the triblock copolymer include styrene-ethylene/butylene-styrene (SEBS), styrene-isoprene-styrene (SIS), and styrene-butadiene-styrene (SBS). In some embodiments, the solvent is an oil, for example, mineral oil. Upon heating a mixture or slurry of the triblock copolymer, the midblocks dissolve in the mineral oil, thereby forming a network of the insoluble endblocks. The resulting network has enhanced elastomeric properties compared with the parent copolymer. In some embodiments, the triblock copolymer used is KRATON® G1651, which has a styrene to rubber ratio of 33/67. Once formed, the gel is substantially permanent and, by the nature of the endblocks, proces sable as a thermoplastic elastomer henceforward. The mixture or slurry has a minimum temperature at which it becomes a gel, which is referred to as the minimum gelling temperature (MGT). This temperature typically corresponds to the glass transition temperature of the thermoplastic endblock plus a few degrees. For example, the MGT for a mixture of KRATON® G1651 and mineral oil is about 120° C. When the slurry reaches the MGT and the transformation to a gel state takes place, the gel becomes more transparent, thereby providing a visual endpoint confirming the complete transformation of the slurry to the gel state, whereupon the gel may be cooled. Some embodiments of the gel comprise a diblock copolymer, either instead of or in addition to the triblock copolymer. Embodiments of the diblock copolymer comprise a thermoplastic first endblock, for example, styrene, and a thermoset elastomeric second endblock, for example, ethylene/butylene, isoprene, or butadiene. An example of a suitable diblock copolymer is styrene-ethylene/butylene (SEB).

For a given mass of slurry to form a complete gel, the entire mass of the slurry is heated to or above the MGT and held at or above the MGT for a sufficient time for the end blocks to form a network or matrix of interconnections. The slurry will continue to form a gel at temperatures between the MGT and temperatures at which the components of the slurry/gel begin to decompose and/or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel depends on the speed with which the entire mass of slurry reaches the MGT. Also, at temperatures higher than the MGT, the end block networks distribute and form more rapidly, thereby speeding the gel formation.

The various base gel formulas may also be mixed or alloyed with one another to provide gels with a variety of intermediate properties. For example, KRATON® G1701X is a mixture of seventy percent (70%) SEB and thirty percent (30%) SEBS, with an overall styrene to rubber ratio of 28/72. Those skilled in the art will appreciate that an almost unlimited number of combinations, alloys, and styrene to rubber ratios can be formulated, each providing and embodiment exhibiting one or more advantages, for example, low durometer, high elongation, and good tear strength.

Some embodiments of the gel material further comprise a polymer that, with a foaming agent, improves the sealing properties of the gel, for example, silicone, soft urethanes, and even harder plastics. Examples of suitable silicones include those used for electronic encapsulation. Examples of suitable harder plastics include polyvinylchloride (PVC), isoprene, KRATON® neat, and other KRATON®/oil mixtures. In the KRATON®/oil mixture, suitable oils include vegetable oils, petroleum oils, and silicone oils, as well as mineral oil.

Some embodiments of the gel comprise one or more additives that provide one or more desirable properties, for example, at least one of enhanced lubricity, improved appearance, and wound protection. Additives are incorporated directly into the gel and/or applied as a surface treatment. In some embodiments, other compounds are added to the gel to modify its physical properties and/or to assist in subsequent modification of the surface by providing bonding sites and/or surface charges. Additionally, oil-based colorants are added to the slurry to create gels of different colors in some embodiments.

Some embodiments of the gel pad 10530 comprise a layer of polyethylene on at least one surface. Polyethylene is dissolved in mineral oil and the solution applied to one or more surfaces of the gel pad 10530. The mineral oil does not evaporate, but instead, absorbs into the gel pad over time, leaving behind the polyethylene as a layer on the surface of the gel pad.

In some embodiments, the triblock copolymer/solvent mixture/slurry used to manufacture the gel pad 10530 comprises about ninety percent (90%) by weight of mineral oil and about ten percent (10%) by weight of KRATON® G1651. From a thermodynamic standpoint, this mixture behaves similarly to mineral oil. Because mineral oil has a relatively high heat capacity, transforming 0.45 kg (1 pound) of the slurry into a homogenous gel at about 130° C. may take from bout three (3) to about four (4) hours. Once formed, the gel can be cooled as quickly as practicable with no apparent deleterious effects on the gel. In some embodiments, the gel is cooled by cold-water immersion. In other embodiments, the gel is air-cooled. Those skilled in the art will recognize that other cooling techniques are used in other embodiments.

Certain properties of the KRATON®/oil gel will vary with the weight ratio of the components. In general, a higher proportion of mineral oil results in a softer gel, while a higher proportion of KRATON® results in a firmer gel. A too-soft gel exhibits excessive tenting or doming of the gel cap 10500 during surgery when a patient's body cavity is insufflated. Some embodiments of gels that are too soft also do provide an adequate instrument seal and/or zero seal. The gel should be sufficiently soft to provide an adequate seal both in the presence of an instrument and in the absence of an instrument, however.

On prolonged or extended sitting or standing, the copolymer, such as KRATON®, and the solvent, such as mineral oil, in the slurry may separate. The slurry may be mixed to greater homogeneity, for example, with a high shear mixer. Mixing the slurry may introduce or add air to the slurry, however. To remove air from the slurry, the slurry may be degassed. In some embodiments, the slurry is degassed under a vacuum, for example, within a vacuum chamber. In some embodiments, the applied vacuum is about 0.79 meters (about 29.9 inches) of mercury, or about one (1) atmosphere. Optionally, stirring or mixing the slurry under vacuum facilitates removal of the air. During degassing under vacuum, the slurry typically expands, then bubbles, and then reduces in volume. The vacuum is typically discontinued when the bubbling substantially ceases. Degassing the slurry in a vacuum chamber reduces the volume of the slurry by about ten percent (10%). Degassing the slurry also reduces oxidation of the finished gel in some embodiments.

Degassing the slurry tends to result in a firmer gel. A gel made from a degassed slurry comprising about 91.6% by weight of mineral oil and about 8.4% by weight of KRATON® G1651, an eleven-to-one ratio, has about the same firmness as a gel made from a slurry that is not degas sed and that comprises about ninety percent (90%) by weight of mineral oil and about ten percent (10%) by weight of KRATON® G1651, a nine-to-one ratio.

Because mineral oil typically has a lower density than KRATON®, the two components will separate after mixing, with the less dense mineral oil rising to the top of the container. This phase separation typically occurs when transforming a static slurry into a gel over several hours. Consequently, the resulting gel is non-homogeneous, with a higher concentration of mineral oil at the top and a lower concentration at the bottom. The speed of separation is a function of the depth or head height of the slurry being heated. Factors relevant to the relative homogeneity of the gel include the mass of slurry, the head height, the temperature at which the gel sets, and the speed at which the energy is transferred to the gel.

The gel pad 10530 or gel cap 10500 are gamma sterilized in some embodiments, which is relatively and/or comparatively simpler to qualify compared with other sterilization process, for example, versus ethylene oxide. Gamma sterilization can cause large bubbles to form in the gel pad, however, which are cosmetic and/or aesthetic issues in the sterilized devices. Because bubbles typically comprise greater than ninety-nine percent (99%) room air, the dissolved air is advantageously removed from the slurry prior to transforming the slurry into a gel. For example, the slurry may be degassed under vacuum, as described above, then gelled by heating. Some bubbles may still form in the gel during gamma sterilization, but typically disappear over a period of from about twenty-four (24) hours to about seventy-two (72) hours. Typically, mineral oil at room temperature has about ten percent (10%) dissolved gas. As discussed above, removing air from the gel makes the gel firmer. This effect is counterbalanced by a softening of the gel by the gamma radiation during gamma sterilization, however.

In some embodiments in which the gel pad 10530 is gamma sterilized, the gel comprises about ninety percent (90%) mineral oil by weight and about ten percent (10%) KRATON® by weight. As stated above, degassing the slurry makes the gel firmer. The counteracting softening by the gamma radiation, however, results in a gel with substantially the same firmness as a gel comprising about ninety percent (90%) mineral oil by weight and about ten percent (10%) KRATON® by weight that is not degassed and gamma sterilized.

In some embodiments, the gel pad 10530 is coupled to, attached to, formed with, or integrated with the cap ring 10510 to provide a gas-tight seal between the cap ring 10510 and the tubular body 6130 (FIG. 6A), 7130 (FIG. 6D). The gel pad 10530 covers and seals the entire opening in the cap ring 10510, as well as covering substantially the entire wound or orifice opening. As stated above, the gel pad 10530 provides a gas tight seal around a variety of shapes and sizes of instruments inserted there through.

Embodiments in which a gel pad support structure of the cap ring 10510 comprises a thermoplastic elastomer, for example, DYNAFLEX® or KRATON®, and the gel pad 10530 comprises a similar thermoplastic elastomer, for example, KRATON®, exhibit improved adhesion between the gel pad 10530 and the cap ring 10510. The polystyrene component of KRATON® in the gel pad 10530 improves adhesion with polyphenylene oxide (PPO), polystyrene, and other similar polymers.

In some embodiments of cap rings 10510 comprising polycarbonate, the polycarbonate component of the cap ring 10510 does not bond with the gel pad 10530 at 130° C., which is a typical manufacturing temperature for a gel pad 10530 comprising KRATON®. Raising the temperature to about 150° C. for a few minutes during casting, however, bonds the gel pad 10530 to the cap ring 10510. It is believed that heating the gel pad 10530 and cap ring 10510 to a temperature at which both the polystyrene component of the gel and the polycarbonate are simultaneously above their melt points allows bonds to form there between. In other embodiments, the uncured gel and the cap ring 10510 are heated to near or at the glass transition temperature of the polycarbonate in the cap ring 10510, thereby bonding the gel pad 10530 to the cap ring 10510.

In some embodiments, the gel comprises mineral oil and the cap ring 10510 comprises a polymer that dissolves in mineral oil under the manufacturing conditions, for example, polyethylene (PE), low density polyethylene (LDPE), high density polyethylene (HDPE), and ultra high molecular weight polyethylene (UHMWPE). Using polyethylene (PE) as an example, PE has a higher molecular weight than mineral oil and dissolves in mineral oil at the temperatures used to cast the gel pad 10530. As such, as a portion of the PE in the cap ring 10510 dissolves in the mineral oil in the gel pad 10530 at the processing temperatures, for example, above about 130° C., a bond between the PE in the cap ring 10510 and gel pad 10530 is formed.

In an embodiment of a method for manufacturing a gel cap, the cap ring 10510 is placed into a mold that together with the cap ring 10510 includes a negative space in the desired shape of the gel pad and uncured gel is added to the mold. Sufficient uncured gel is then added to the mold to cover and fill the apertures 10512. The uncured gel flows through, fills, and remains within the apertures. Also, in some embodiments, the mold is filled with sufficient uncured gel to extend into the distal portion of the cap ring 10510. After the gel cures, the gel in the apertures connects and couples the gel on a first side of each aperture 10512 to the gel on a second side of the aperture, thereby mechanically locking the gel pad 10530 to the cap ring 10510.

Some embodiments include another method for coupling the gel pad 10530 to the cap ring 10510, either in addition to or instead of the mechanical interlocking discussed above. Such methods are useful, for example, for coupling separately formed gel pads or gel slugs 10530 and cap rings 10510. Some embodiments use a glue or adhesive to couple the gel pad 10530 to the cap ring 10510, for example, cyanoacrylate (SUPERGLUE® or KRAZY GLUE®). The glue is believed to bond to either the rubber or the styrene component of the triblock copolymer with a bond is frequently stronger than the gel material itself. Some embodiments use solvent welding in which a solvent dissolves a plastic in the cap ring 10510 and the polystyrene in the gel pad 10530. The solvent is applied to the gel pad 10530 and cap ring 10510 by any suitable method, for example, by spraying and/or by dipping. In effect, the solvent melts both the plastic of the cap ring 10510 as well as the polystyrene in the gel pad 10530, thereby forming a bond between the two, which remains after the solvent evaporates.

In an embodiment for manufacturing a gel cap 10500, the gel pad 10530 is cast into the cap ring 10510 to form the gel cap 10500. The cap ring 10510 is positioned in or placed into a mold cavity of a casting mold. Embodiments of the mold cavity include support for the annular walls of the cap ring 10510. Embodiments of the mold comprise a material with sufficient heat dissipation properties, for example, at least one of aluminum, copper, and brass. Those skilled in the art will recognize that other mold materials with lower heat dissipation properties will produce acceptable parts in some embodiments. Furthermore, some embodiments of the mold comprise active cooling elements, for examples, channels through which coolants are pumped.

The mold cavity and cap ring 10510 assembly is then filled with a desired amount of the triblock copolymer/mineral oil slurry such that the slurry contacts the cap ring 10510. In some embodiments, the slurry is preheated, for example, to about 52° C. (125° F.), which facilitates a complete filling of the mold cavity by the slurry, thereby reducing the probability of voids in the gel. Preheating the slurry to a temperature below the MGT reduces the viscosity of the slurry and allows the slurry to flow more easily. As stated above, some embodiments of the slurry are degassed in a vacuum before casting. In some embodiments, the slurry is also degassed after it is filled in the mold cavity to remove any air that may have been introduced during the filling of the mold cavity, as well as to facilitate flow of the slurry into voids in the mold. The mold, cap ring, and slurry are heated, for example, in an oven, until the slurry reaches a temperature of about 150° C. As stated above, the slurry turns into gel at about 120° C.; however, at about 150° C., the gel bonds to a polycarbonate cap ring 10510. Depending on the material used in the cap ring 10510, bonding may take place at a temperature other than about 150° C. In embodiments in which the cap ring 10510 is comprises a material with a lower melting point than the MGT, for example 120° C., the gel pad 10530 is molded separately as a gel slug, which is then bonded to the cap ring 10510 as discussed above.

When the transformation of the slurry into a gel is complete, for example, when the temperature of the gel pad reaches about 150° C., the gel cap 10500 is cooled, for example, by air-cooling, cold-water immersion, or another suitable method. At 150° C. the gel pad 10530 is soft and easily distorted. Distortions in the gel pad 10530 present during cooling would be set after cooling. Accordingly, in some embodiments, the gel cap 10500 is cooled within the mold, thereby reducing the likelihood of distorting the gel pad 10530. Factors affecting the cooling time include the size and configuration of the mold, the quantity of gel, temperature and quantity of cooling medium, the properties of the cooling medium, and the mold material. As an example, the cooling time for a particular gel cap 10500 may be about two (2) hours for air cooling and about fifteen (15) minutes for water cooling. Whether cooling with air or water, the final properties of the gel are substantially the same. The gel cap 10500 is typically cooled to about ambient room temperature, but may be cooled to a lower temperature if desired. At about 0° C., the gel hardens, which is useful, for example, in secondary operations such as when coupling separately manufactured gel pads 10530 and cap rings 10510. The gel cap 10500 may be removed from the mold at any time after the gel has set.

When removed from the mold, the gel pad 10530 typically has a tacky surface. Coating the gel pad 10530 with a powder, such as cornstarch, substantially reduces or eliminates the tackiness of the cured gel pad 10530.

As stated above, in some embodiments, the gel pad 10530 is molded separately from the cap ring 10510, and coupled to the cap ring 10510 in a secondary operation, for example, bonding. In some embodiments, the gel pad 10530 is molded as a gel slug with an outer perimeter smaller than the perimeter of the inner cylindrical wall of the cap ring 10510 and a height greater than the height of the cap ring 10510. Because the gel pad 10530 is molded separate from the cap ring 10510, the slurry need only be heated to the MGT, for example, about 120° C., to complete the transformation of the slurry into a gel, whereupon the gel becomes substantially transparent. As discussed above, the gel slug may be cooled, for example, to about 0° C., then placed within the inner cylindrical wall of the cap ring 10510.

In some embodiments, the gel slug is coupled to the cap ring 10510 through compression molding, in which the gel slug is compressed longitudinally, thereby expanding the outer perimeter of the gel slug and compressing the gel slug against the inner cylindrical wall of the cap ring 10510. The compressed gel slug and cap ring 10510 are then heated to a sufficient temperature for the polystyrene in the gel and the polymer of the cap ring 10510 to form bonds there between. Molding the gel slug separately from the cap ring 10510 followed by heat bonding the gel slug to the cap ring is especially useful in embodiments in which the cap ring 10510 comprises a material with a melting temperature lower than the MGT of the gel. In such situations, the gel slug can be molded separately and heat bonded to the cap ring 10510 without melting the cap ring 10510.

An embodiment of a method for retracting an incision or body orifice using the retractor 6100, 7100 is discussed in detail above. The method results in the outer ring 6120, 7120 of the retractor substantially in contact with the exterior surface of the body wall. The gel cap 10510 is then coupled to the outer ring 6120, 7120 of the retractor, thereby sealing the opening between the body cavity and the area outside the body cavity and allowing the surgeon to insufflate the body cavity.

As discussed above, embodiments of the gel cap 10500 comprise no preformed access channels in the gel pad 10530. In use, instruments may be inserted directly through the gel pad 10530, thereby creating access channels through the gel pad 10530. Each access channel created in the gel cap forms an instrument seal in the presence of an instrument passing there through because the gel provides a gas tight seal around a variety of shapes and sizes of instruments. When the instrument is removed from the gel pad 10530, the channel created in the gel pad by the instrument closes to form a zero seal.

Some embodiments of the cap use access devices such as trocars inserted through the gel pad 10530 for instrument access, in particular, where an access channel experiences repeated instrument manipulation, for example, insertion, removal, advancement, retraction, rotation and/or other manipulation. Each trocar inserted through the gel pad 10530 permits repeated introduction, removal, and/or manipulation of instruments there through.

In some embodiments, the gel cap 10500 initially comprises no access channels, and the surgeon is at liberty to determine the placement of instruments there through. Moreover, the surgeon has unlimited flexibility in the placement and repositioning of ports within the area of the gel cap 10500, as well as the option of selecting different trocar sizes for different clinical procedures. Being detachable, the gel cap 10500 allows for the removal of large specimens. Once removed, the gel cap 10500 can be re-coupled to the outer ring 6120, 7120 of the retractor, thereby restoring the seal and allow the surgeon to re-insufflate the body cavity.

Moreover, embodiments of the gel are deformable without losing physical integrity, and while maintaining substantially gas tight instrument seals with any instruments extending there through, as well as gas tight zero seals for any access channels without any instruments extending there through. Accordingly, embodiments of the gel cap 10500 permit both translational or positional, and angular or pivotal "float" or degrees of freedom for the instruments passing through the gel pad 10530. This float permits instrument motion both relative to the cap ring 10510 as well as relative to other instruments. In contrast, other single or limited port systems do not exhibit one or both translational or angular float for instruments.

Figure 11A:
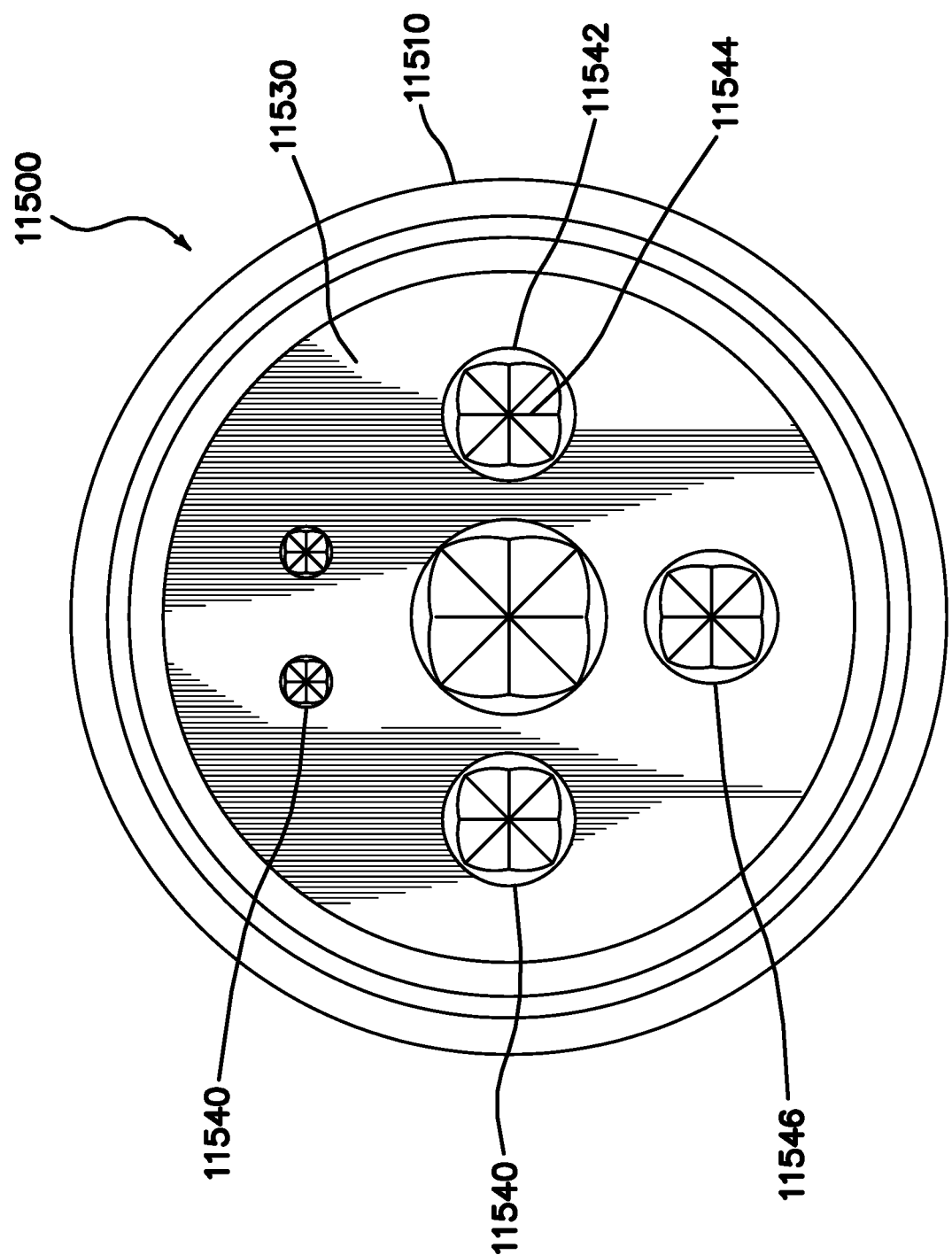
FIG. 11A is a top view of an embodiment of a gel cap comprising a plurality of access ports embedded in the gel pad.
Figure 11B:
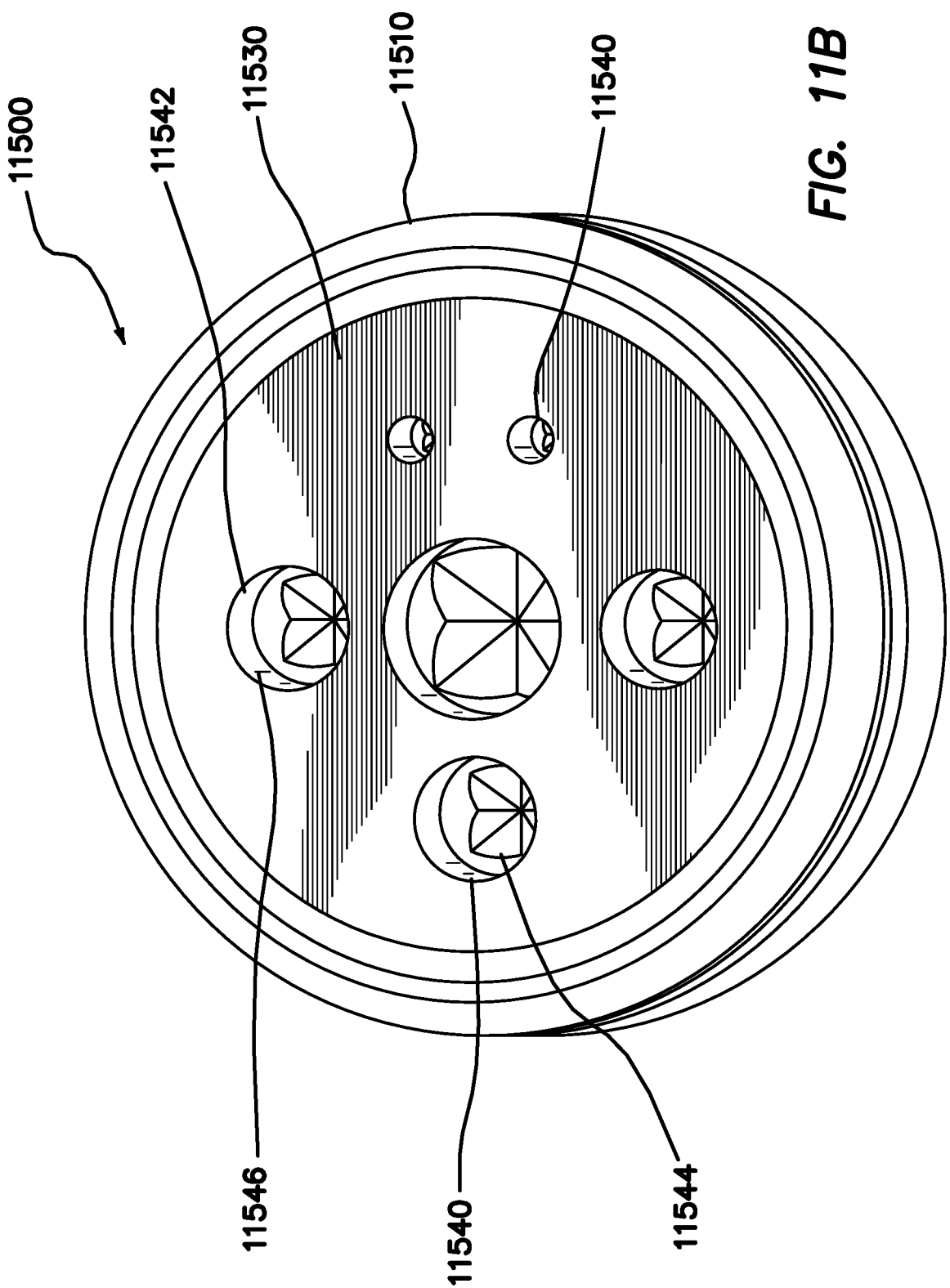
FIG. 11B is a top perspective view of the gel cap illustrated in FIG. 11A.
Figure 11C:
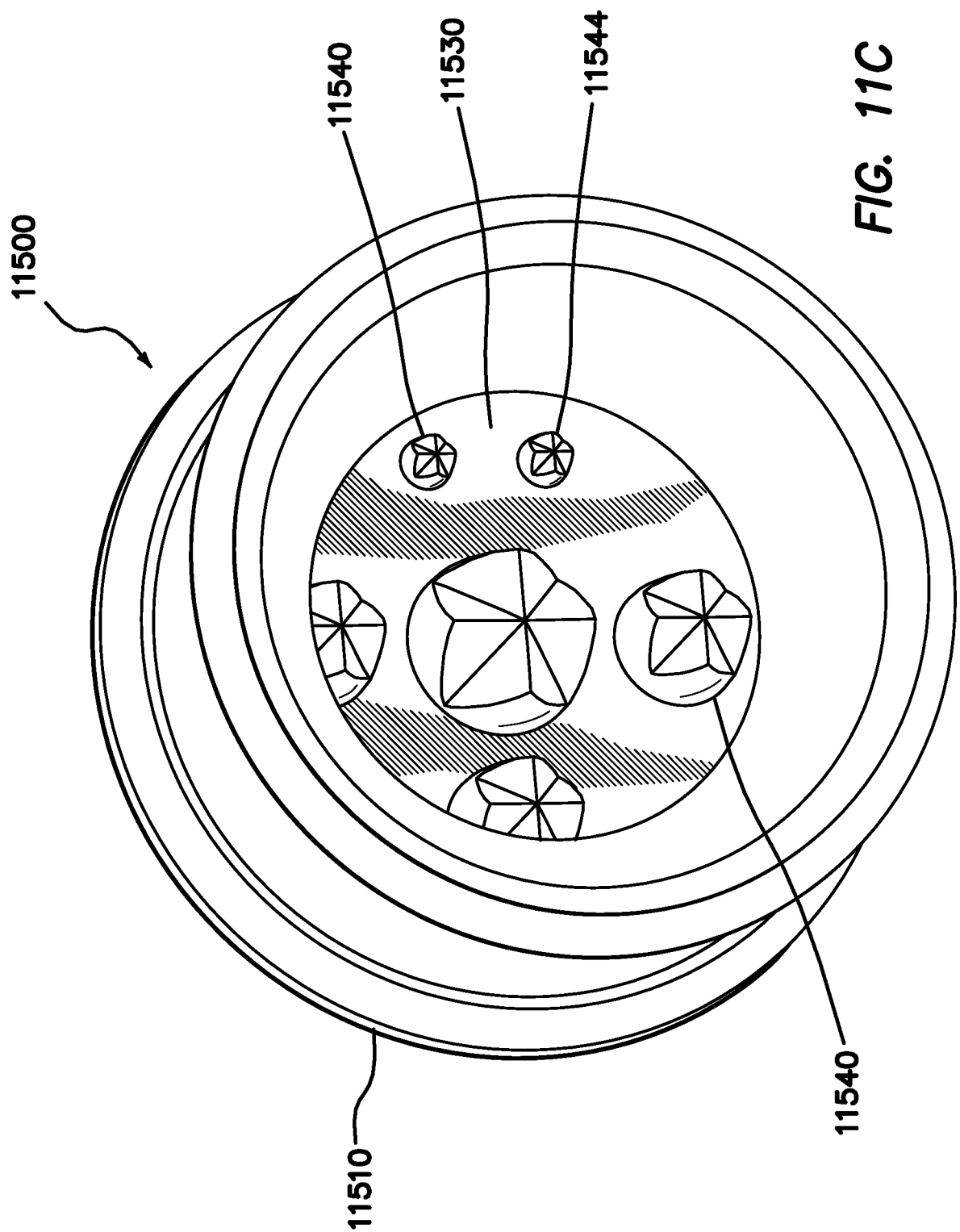
FIG. 11C is a bottom perspective view of the gel cap illustrated in FIG. 11A.

FIG. 11A is a top view of an embodiment of a gel cap 11500 comprising a plurality of access ports, seals, or sealing valves disposed in the gel pad. FIG. 11B is a perspective top view of the gel cap 11500 mounted on a retractor. FIG. 11C is a perspective bottom view of the gel cap 11500 mounted on a retractor. The gel cap 11500 comprises a cap ring 11510 and a gel pad 11530, which are generally similar to the cap ring and gel pad of the embodiment described above.

The gel cap 11500 further comprises a plurality of access ports 11540, at least a portion of which is disposed within or embedded within the gel pad 11530. In the illustrated embodiment, the access ports 11540 have a low profile, that is, do not protrude or protrude minimally above the proximal surface of the gel pad 11530 and/or below the distal surface of the gel pad 11530. Accordingly, the lengths of the access ports 11540 are similar to the thickness of the gel pad 11530, which is shorter than a length of a typical trocar inserted in the gel pad 11530, which comprises a seal assembly positioned above the gel pad 10530, and a cannula extending through the gel pad 11530. The reduced length of the access port 11540 allows increased angular or pivotal motion for instruments extending there through, and also permits the use of curved and/or angled instruments. In the illustrated embodiment, the access ports 11540 are substantially permanent or non-removable under the conditions under which the gel cap 11500 is used. Trocars can also be inserted through the gel pad 11530 if additional ports are desired.

Each port 11540 comprises longitudinal axis extending from a proximal side to a distal side of the gel pad 11530, a first seal 11542 disposed at the proximal side of the gel pad 11530, and a second seal 11544 disposed distal to the first seal 11542. A sight of each of the ports or seals 11540 has an aperture through the gel pad 11530 and coincides with the longitudinal axis. In the illustrated embodiment, the first seal 11542 forms an instrument seal with an instrument extending there through and the second seal 11544 forms a zero seal in the absence of an instrument extending there through.

In the illustrated embodiment, the first seal 11542 comprises a septum seal. Each septum seal comprises an aperture 11546 there through that is slightly smaller than a cross-section of the smallest instrument to be inserted there through. The aperture 11546 of the septum seal is substantially aligned with the aperture through the gel pad and the longitudinal axis of the port 11540. When an instrument is inserted through the aperture 11546 of the septum seal, the aperture 11546 expands and engages the outer surface of the instrument, thereby forming a seal therewith. The septum seal comprises an elastomeric material that biases the aperture against an instrument is inserted there through. Those skilled in the art will understand that other types of instrument seals are used in other embodiments.

Figure 11D:
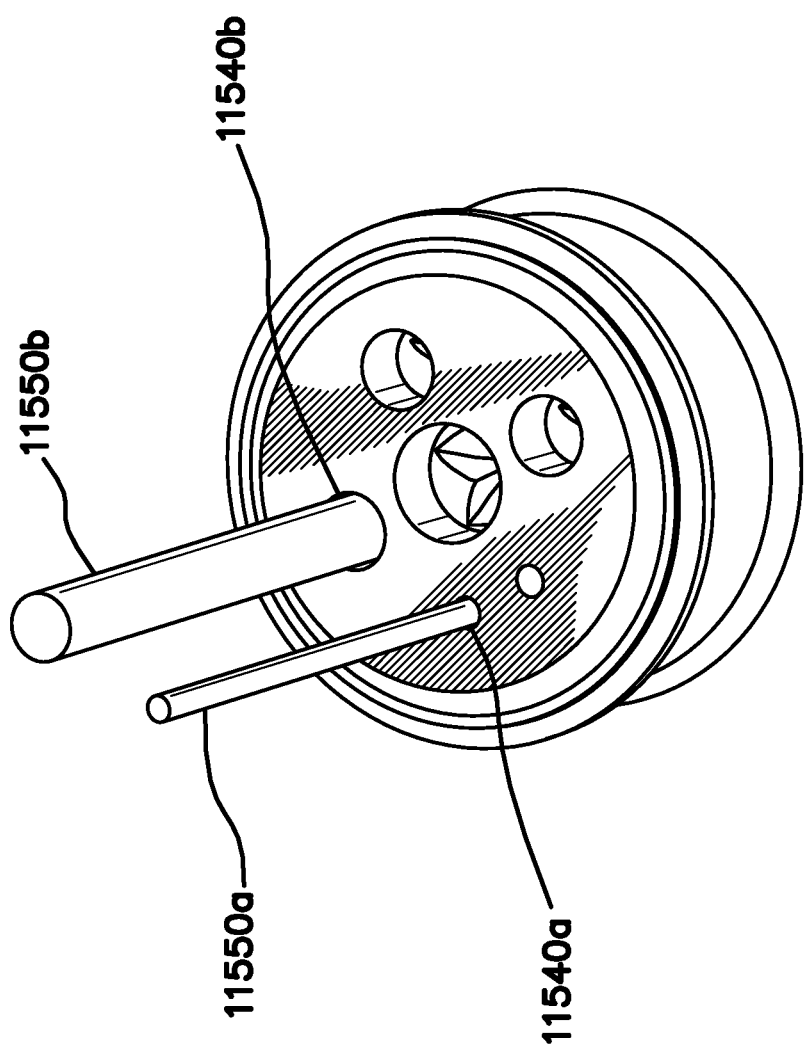
FIG. 11D is a top perspective view of the gel cap illustrated in FIG. 11A with instruments inserted through two of the access ports.
Figure 11E:
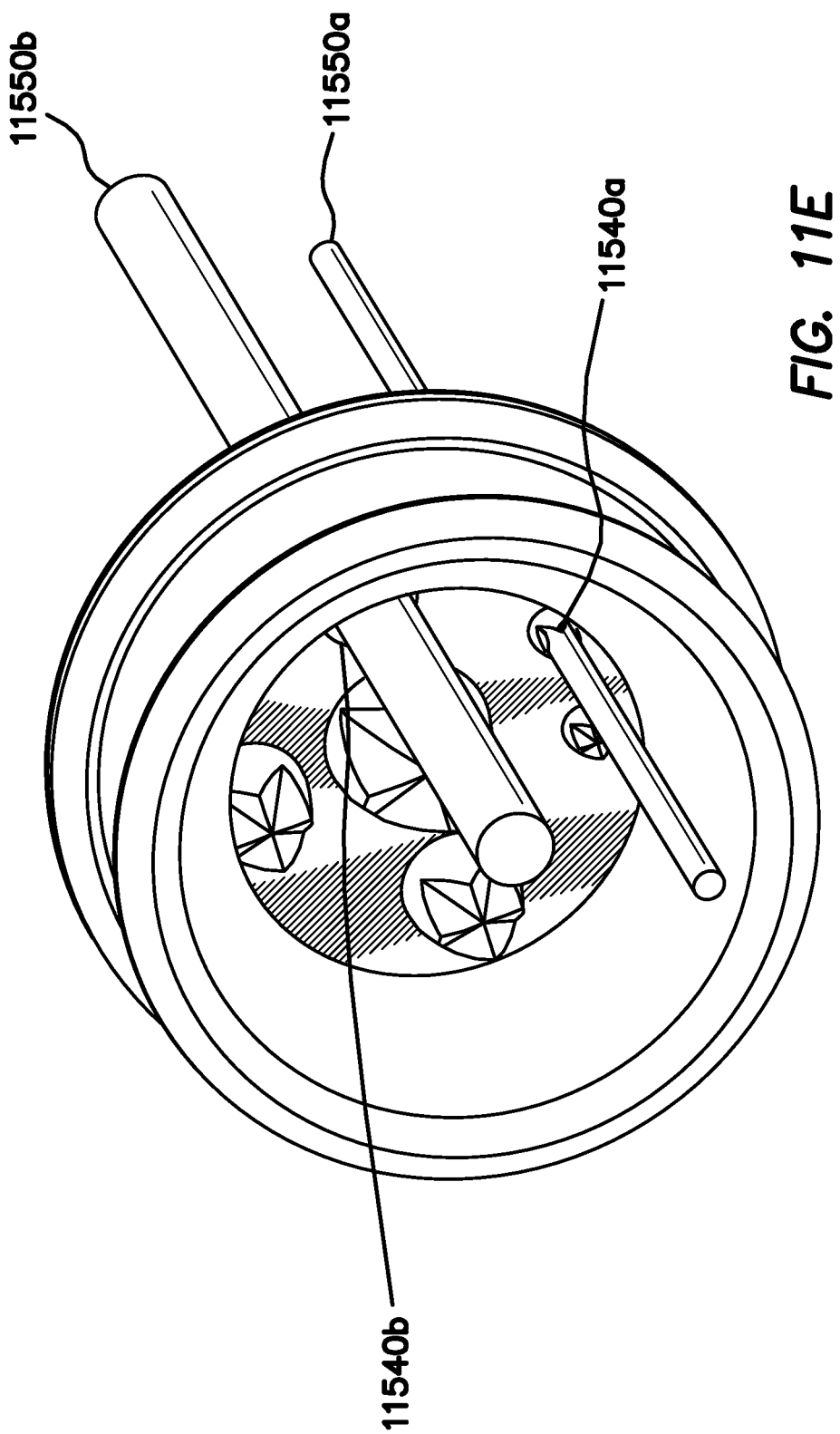
FIG. 11E is a bottom perspective view of the gel cap and instruments illustrated in FIG. 11D.
Figure 11F:
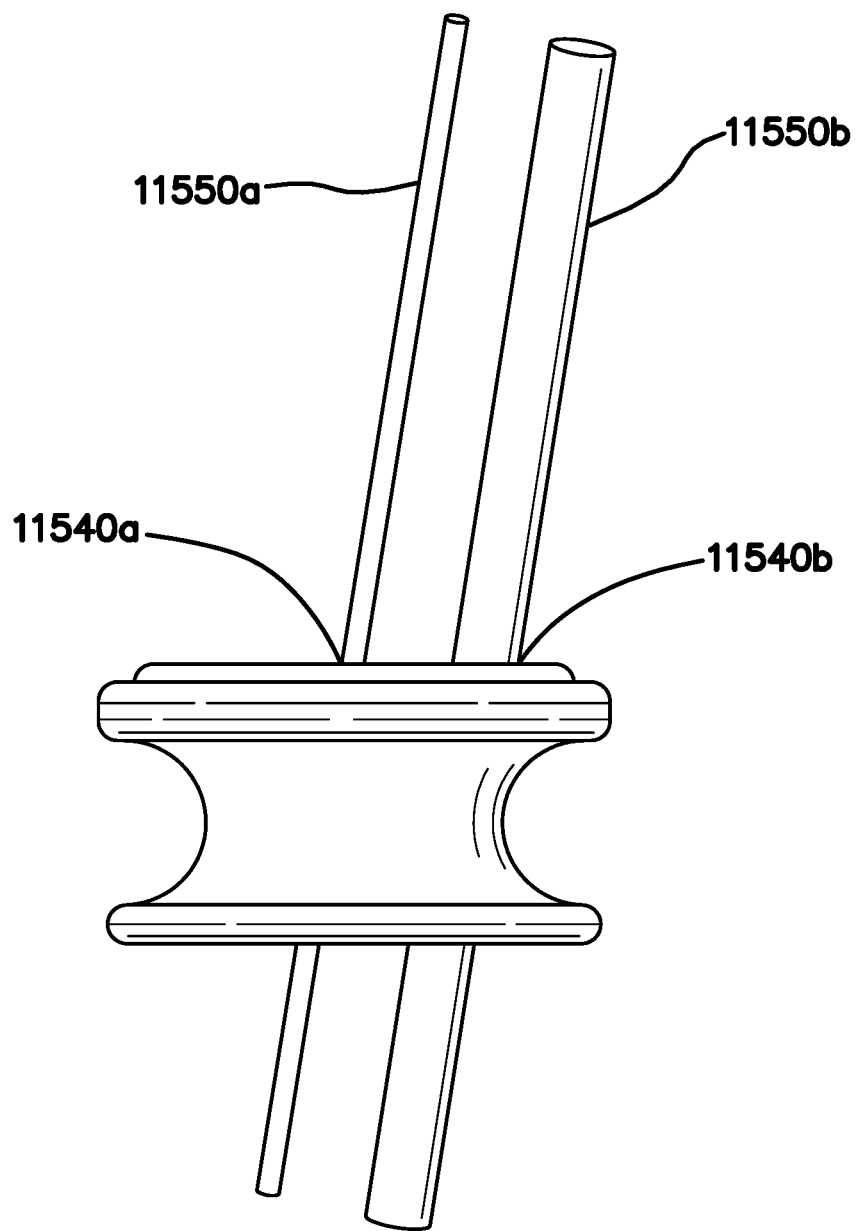
FIG. 11F is a side view of the gel cap and instruments illustrated in FIG. 11D.

In the illustrated embodiment, the second seal 11544 comprises a double-duckbill valve, which functions as a zero-closure seal that provides a zero seal in the absence of an instrument inserted there through. Those skilled in the art will understand that the second seal comprises another type of seal, for example, a duckbill valve, a flap valve, and the like. The double-duckbill valve comprises as elastomeric material. In some embodiments, each of the first seal 11542 and the second seal 11544 independently comprise an elastomeric material, for example, at least one of rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (NEOPRENE®), perfluoroelastomer (KALREZ®), and the like Thus, during use, the septum seal provides an instrument seal in the presence of an instrument inserted there through, and the duckbill valve provides a zero seal in the absence of an instrument inserted there through. The illustrated embodiment comprises ports or seals 11540 in the gel pad of different sizes. Each size of port 11540 sealing accommodates a different range of instrument sizes inserted there through. The size of a port is typically given as the diameter of the largest instrument that the port will accommodate, for example, 5 mm, 11 mm, or 12 mm. FIGS. 11D, 11E, and 11F are a perspective top view, a perspective bottom view, and a side view of a thinner instrument 11550*a* and a thicker instrument 11550*b* inserted through a smaller port 11540*a* and a larger port 11540*b*, respectively, of the embodiment of the gel cap 11500 illustrated in FIGS. 11A-11C.

FIG. 11G is a top perspective view of an embodiment of a gel cap 11500 further comprising a fixed port position, for example, for a camera or a laparoscope. The fixed port 11560 comprises a lock mechanism 11562 that maintaining the position of a camera or laparoscope inserted there through. In some embodiments, one of the ports 11540 further comprises a stopcock and/or gas fitting used as a gas inlet and/or outlet port for insufflating, depressurizing, and/or venting the body cavity of gas. In some embodiments, a gas inlet/outlet port is disposed on the cap ring 11510.

Figure 12:
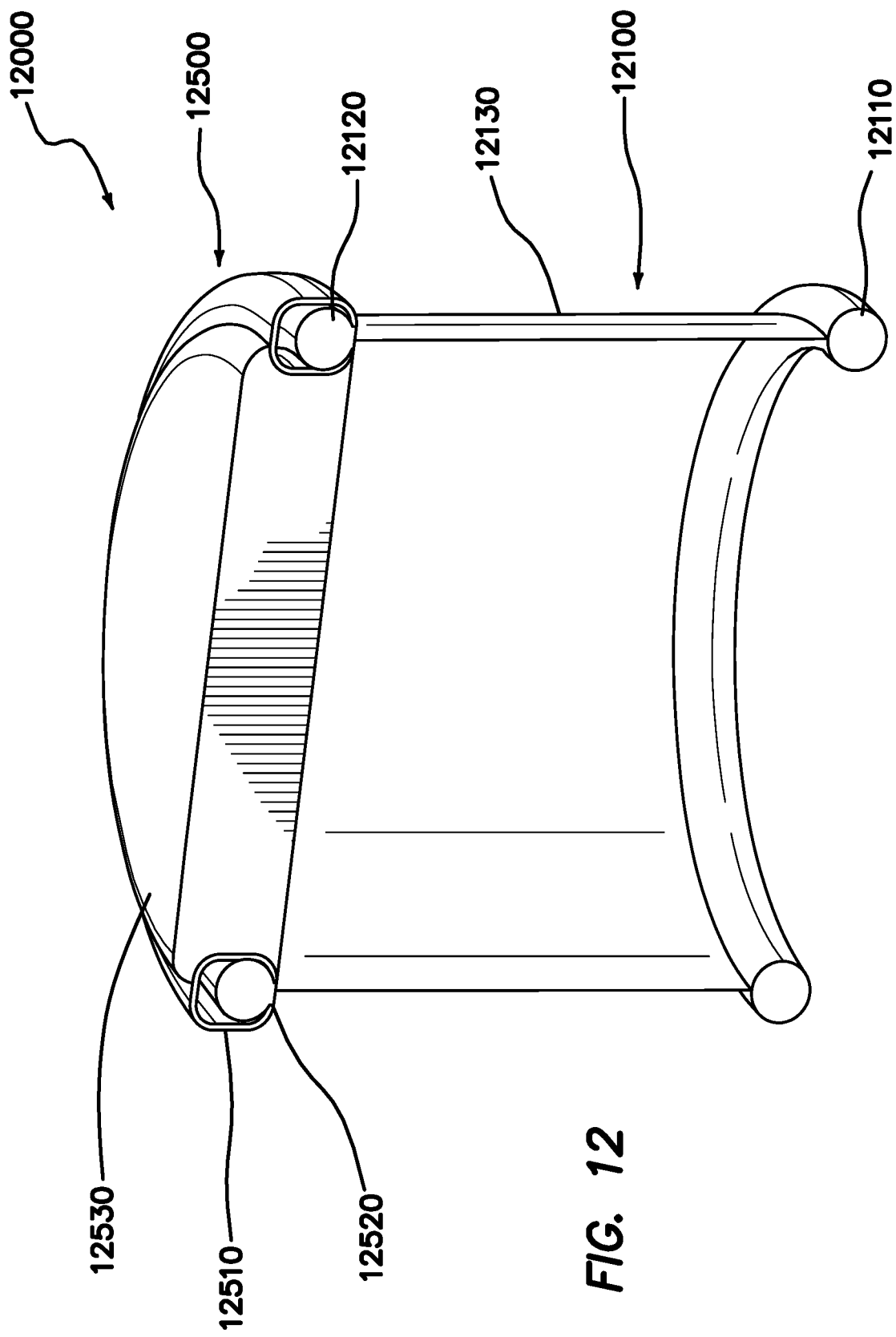
FIG. 12 is a cutaway perspective view of an embodiment of an access device system comprising a gel cap that snap fits to a retractor.

FIG. 12 is a cutaway perspective view of an embodiment of an access device system 12000 comprising retractor 12100 and a cap or cover 12500, which are similar to embodiments of retractors and gel caps described above. The retractor 12100 comprises an inner ring 12110, an outer ring 12120, and a sleeve 12130 extending between the inner ring 12110 and the outer ring 12120. In the illustrated embodiment, the cap 12500 is a gel cap comprising a proximal side, a distal side, a cap ring 12510, and a gel pad 12530. In the illustrated embodiment, the cap ring 12510 comprises a tubular ring dimensioned to receive the outer ring 12120 of the retractor therewithin. The distal side of the cap ring 12510 comprises an annular slot 12520, which is sufficiently radially deformable for the outer ring 12120 to reversibly pass there through. Accordingly, the illustrated embodiment of the cap ring 12510 secures the cap 12500 to the outer ring 12120 with a snap or friction fit.

Figure 13:
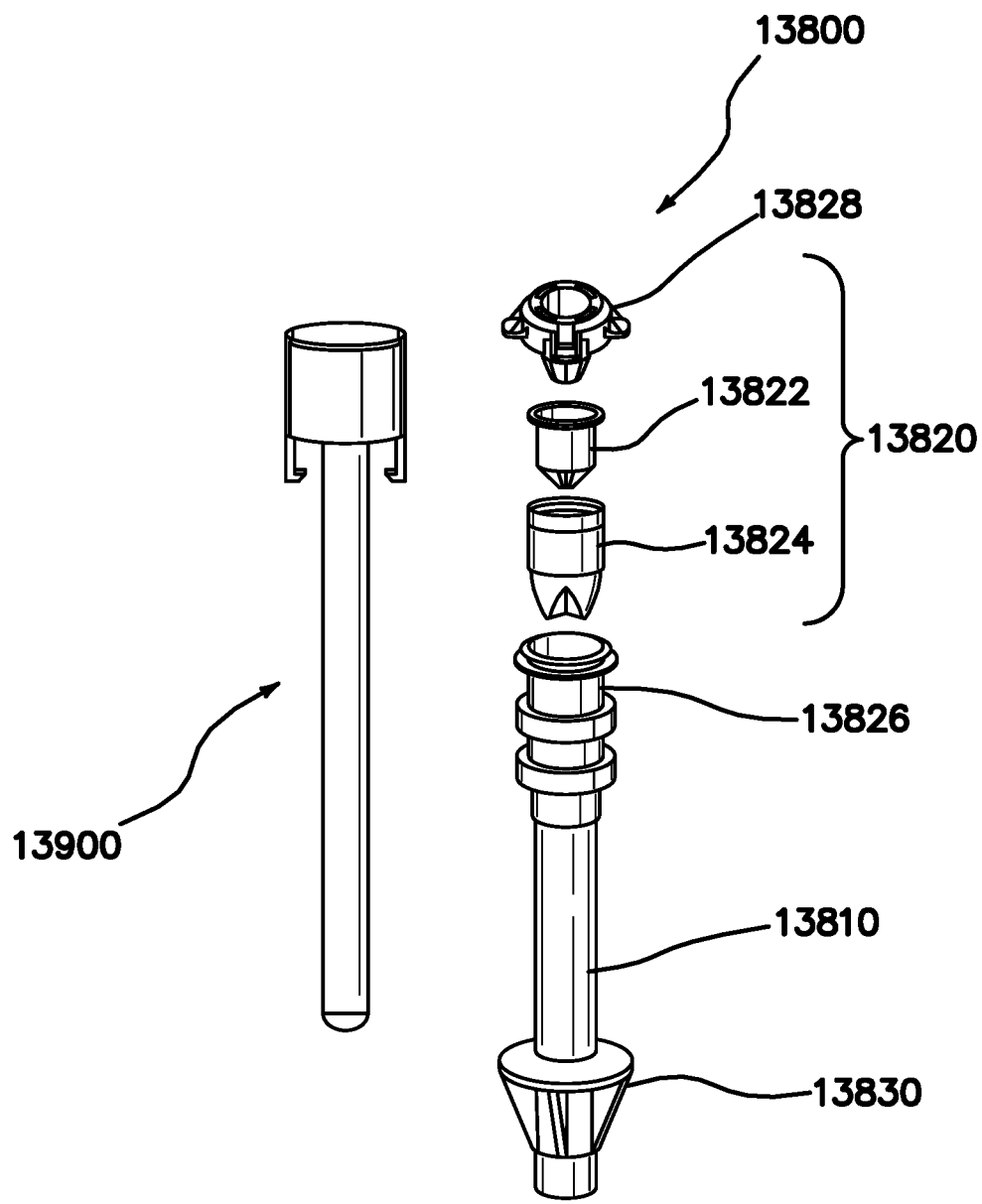
FIG. 13 is an exploded view of an embodiment of a trocar.

FIG. 13 is an exploded view of an embodiment of a trocar 13800 and optional obturator 13900, which is a component of some embodiments of the access device system. In the illustrated embodiment, the obturator 13900 comprises a pointed, puncture tip 13910. In embodiments in which the trocar 13800 and obturator 13900 are inserted through a gel pad 10530 rather than a body wall, potential damage to underlying tissue by contact with the tip 13910 is reduced because the gel pad 10530 serves as an artificial body wall that is spaced from the underlying tissue as discussed above. In other embodiments, the obturator tip 13910 has another shape, for example, blunt and/or bladeless, which, for example, reduces the likelihood of damage to other components of the access system, for example, a retraction sheath of a retractor.

The trocar 13800 comprises a proximal end, a distal end, and a longitudinal axis. The trocar 13800 comprises a cannula 13810 extending along the longitudinal axis. A trocar seal 13820 is disposed at the proximal end of the cannula 13810. A retainer 13830 is disposed at the distal end or tip of the cannula 13810. In the illustrated embodiment, the distal end or tip of the cannula 13810 is not angled. Other embodiments comprise an angled distal end or tip of the cannula 13810. The illustrated embodiment of the trocar 13800 does not comprise an insufflation gas inlet. Consequently, the trocar 13800 is typically used in procedures in which a body cavity is not insufflated, or in which insufflation is provided through another device. Other embodiments of trocars are disclosed in U.S. patent application Ser. No. 11/677,994, filed Feb. 22, 2007, the disclosure of which is incorporated by reference.

The cannula 13810 comprises an elongate, tubular cannula body 13812 dimensioned to accommodate an instrument or instruments received there through. In the illustrated embodiment, the cannula body 13812 is a substantially cylindrical tube, and extends through the gel pad 10530 in use. In the illustrated embodiment, the cannula body 13812 extends from the proximal end of the cannula 13810 to which the trocar seal 13820 is coupled, and which has a larger outer diameter than the cannula body 13812.

In some embodiments, the cannula 13810 is comparatively short because the cannula body 13812 need only traverse the gel pad 10530 (FIG. 10A), which has a known and consistent thickness, rather than a body wall. Accordingly, some embodiments of the cannula body 13812 are not more than about 2-times longer, about 1.5-times longer, about 1.2-times longer, or about 1.1-times longer than the thickness of the gel pad. In some embodiments, the cannula body 13812 is less than about 20 mm, about 10 mm, or about 5 mm longer than the thickness of the gel pad. In some embodiments, the cannula body 13812 is about as long as the gel pad is thick. In other embodiments, the cannula body 13812 has a different length, for example, a length typical for a cannula used for traversing a body wall. Shorter length cannula bodies permit increased angular degrees of freedom for instruments passing there through. Embodiments of shorter cannula bodies also accommodate curved instruments. The cannula 13810 comprises any suitable biocompatible material. In some embodiments, the cannula 13810 comprises a flexible material.

The illustrated trocar seal 13820 comprises an instrument or septum seal 13822 and a zero seal 13824. The instrument seal 13822 seals instruments passing there through, thereby maintaining pressurization in a body cavity such as pneumoperitoneum or pneumorectum. The zero seal 13824 provides a seal when no instrument passes through the trocar seal 13820. The instrument seal 13822 and zero seal 13824 are received in a housing 13826 disposed at the proximal end of the cannula 13810 and secured therein by a seal cover 13828.

The retainer 13830 is disposed at or near the distal end of the cannula 13810. In the illustrated embodiment, the distal end of the cannula 13810 is generally perpendicular to the longitudinal axis thereof, or not angled. Other embodiments comprise an angled distal end or tip. In some embodiments, the retainer 13830 and cannula 13810 are integrated, while in other embodiments, the retainer 13830 and cannula 13810 are not integrated. In the illustrated embodiment, the proximal end of the retainer 13830 comprises a flange 13832 that is generally flat and perpendicular to the longitudinal axis, while the distal end is tapered, narrowing toward the distal end of the cannula 13810. The flange 13832 reduces the likelihood of accidental or inadvertent removal of the trocar 13800 from the gel pad. Some embodiments of the proximal face of the flange 13832 comprise additional anchoring features, for example, at least one of barbs, spikes, ridges, texturing, and the like, which are configured to penetrate or bite into a distal face of the gel pad 10530. In some embodiments, a diameter of the flange 13832 is from about 1.5 to about 2.5 times wider, or from about 2 to about 2.2 times wider than an outer diameter of the cannula body 13812. Some embodiments of the trocar 13800 are 5-mm trocars, in which the outer diameter of the cannula body 13812 is from about 7 mm to about 8 mm.

The tapered end of the retainer 13830 facilitates insertion of the trocar 13800 through the gel pad, either by itself, or when assembled with the obturator 13900 extending there through. For example, in some embodiments, the retainer 13830 is inserted through a preformed opening in the gel pad 10530. Because embodiments of the gel material of the gel pad 10530 have high elongation values, as discussed above, the retainer 13830 is insertable through a relatively small opening in the gel pad 10530, yet resists inadvertent removal, as discussed above.

In some embodiments in which the retainer 13830 and cannula 13810 are not integrated, that is, are separate components, the retainer 13830 is secured to the cannula 13810 after the cannula 13810 is inserted through the gel pad. In some embodiments, the cannula 13810 and retainer 13830 are secured mechanically, for example, using latches, screw threads, clips, lock rings, ratchets, and the like. In some embodiments, the cannula 13810 and retainer 13830 are secured adhesively. In some embodiments, the position of the retainer 13830 is adjustable, for example, to accommodate gel pads of different thicknesses. In some embodiments, the cannula 13810 and/or retainer 13830 is secured to the gel pad, for example, adhesively.

Figure 14A:
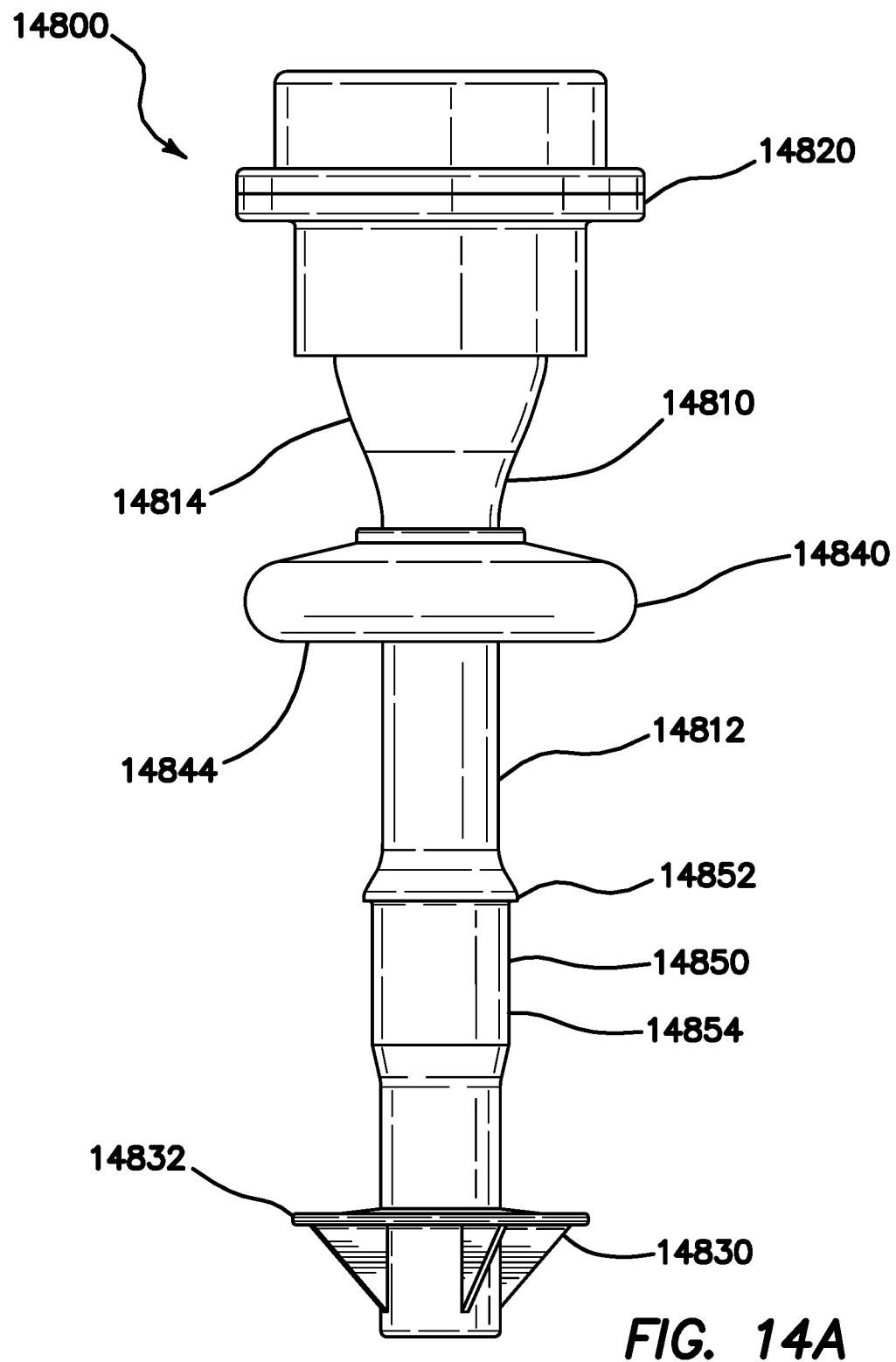
FIGS. 14A and 14B are side views of an embodiment of a trocar comprising a fixation cannula in an insertion configuration and a fixation configuration, respectively.

FIG. 14A is a side view of another embodiment of a trocar 14800 that is suitable as a component of a single-port surgical access system described above, for example, comprising a gel pad 10530 and retractor. Some embodiments of the access system comprise a plurality of trocars 14800. The trocar 14800 is generally similar to the trocar 13800 described above, and comprises a cannula 14810, a trocar seal assembly 14820, and a retainer 14830, which are generally similar to the corresponding features described above. The illustrated embodiment of the trocar 14800 further comprises a bolster 14840 and a locking component 14850. The illustrated embodiment of the cannula 14810 is also referred to as a "fixation cannula" as will become apparent from the discussion below.

In the illustrated embodiment, the bolster 14840 comprises a torus or doughnut. A cannula body 14812 extends through an opening in the bolster 14840. A diameter of the opening of the bolster 14840 is sufficiently larger than an outer diameter of the cannula body 14812 to permit free movement along the cannula body 14812. The illustrated embodiment of the bolster 14840 comprises a deformable material, for example, a polymer resin and/or elastomer, as will be described in greater detail below. Examples of suitable materials include rubber, natural rubber, synthetic rubber, polyisoprene, styrene-butadiene rubber, silicone rubber, ethylene-propylene copolymer, ethylene-propylene-diene monomer rubber, polybutadiene, polychloroprene, polyurethane, and the like. Some embodiments of the bolster 14840 comprise a lubricious layer or coating in an area or region that contacts the cannula 14810, which facilitates movement along the cannula 14810.

An outer diameter of some embodiments of the bolster 14840 is from about 0.8 to about 2 times, or from about 1 to about 1.5 times a diameter of a flange 14832 of the retainer 14830. A thickness of the bolster is from about 3 mm (0.12 inch) to about 10 mm (0.4 inch), or from about 4 mm (0.16 inch) to about 6 mm (0.24 inch). In some embodiments, a distal face 14844 of the bolster is concave, thereby providing additional clamping or fixation force on the gel pad 10530, as well as conforming to gel pads 10530 with different and/or non-uniform thicknesses. The particular dimensions of the bolster 14830 are selected based on the properties of the bolster material and the gel material, and the dimensions of the cannula body 14812, the locking component 14850, and the gel pad 10530.

The locking component 14850 is disposed on the cannula body 14812 proximal of the retainer 14830, and comprises a lip 14852 proximal of an enlarged section 14854. The lip 14852 extends radially from the cannula body 14812 with a diameter greater than the diameter of the opening of the bolster 14840. The elastomeric material of the bolster 14840 permits the bolster 14840 to be urged over and past the lip 14852. In the illustrated embodiment, the lip 14852 comprises a ratchet dimensioned to facilitate the bolster 14840 sliding distally and to resist the bolster 14840 from sliding proximally. Also, in the illustrated embodiment, the lip 14852 is a continuous structure encircling the cannula body 14812. In other embodiments, the lip 14852 comprises a plurality of structures disposed around the cannula body 14812.

The enlarged section 14854 is generally cylindrical with a diameter that is about the same as or slightly larger than the diameter of the opening in the bolster 14840, thereby frictionally engaging the bolster 14840 thereto. In the illustrated embodiment, the enlarged section 14854 is longer than a thickness of the bolster 14840. In the illustrated embodiment, the enlarged section 14854 does not extend to or contact the flange 14832 of the retainer 14830, thereby not reducing a surface area of a proximal face thereof, and thereby improving the removal resistance thereof. In other embodiments, the enlarged section 14854 extends to the retainer 14830. Other embodiments do not comprise an enlarged section.

A distance between a distal end of the lip 14852 and a proximal face of the flange 14832 is equal to or slightly less than a sum of a thickness of the bolster 14840 and the gel pad 10530. In some embodiments, the gel pad is from about 5 mm (about 0.4 inch) to about 30 mm (about 1.2 inch) thick, or from about 13 mm (about 0.5 inch) to about 25 mm (about 1 inch) thick.

Figure 14B:
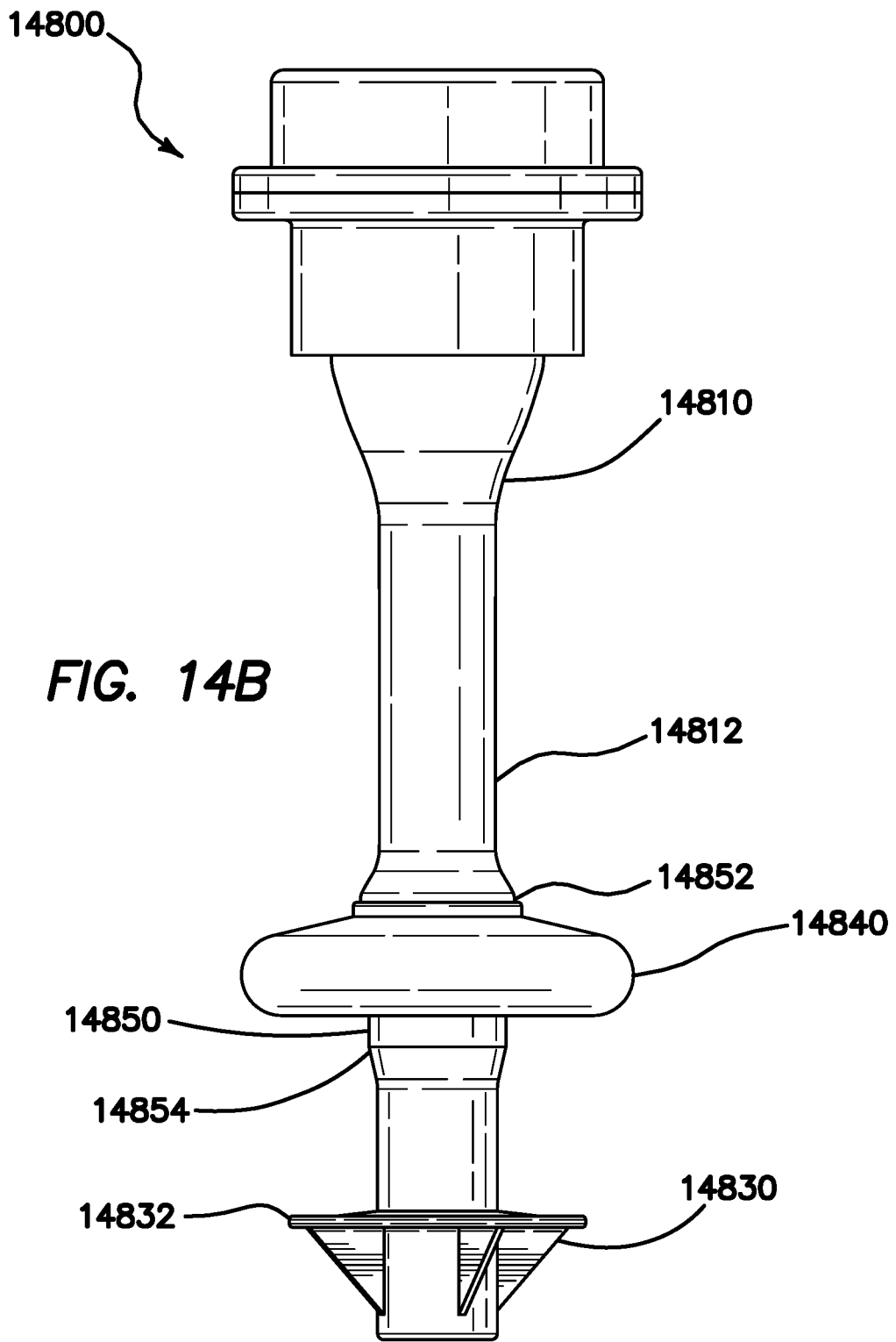

The trocar 14800 has at least two configurations: a first or insertion configuration illustrated in FIG. 14A, and a second or fixation configuration illustrated in FIG. 14B.

In an embodiment of a method for using the trocar 14800, the trocar 14800 is placed in the insertion configuration in which the bolster 14840 is first positioned on the cannula body 14812. The trocar 14800 is placed in the artificial body wall either before the artificial body wall is coupled to a patient's body and/or after coupling thereto.

In the embodiment illustrated in FIG. 14A, the bolster 14840 is positioned at the proximal end of the cannula body 14812, where the bolster 14840 frictionally engages a distal portion of a cannula bell 14814, which is an enlarged portion at the proximal end of the cannula 14810 to which the seal assembly 14820 couples.

The distal end of the trocar 14800 is positioned on, then the retainer 14830 inserted through an artificial body wall, for example, a gel pad 10530. In some embodiments, an obturator 13900 (FIG. 13) is first inserted through the seal assembly 14820 at the proximal end of the trocar with the tip 13910 extending from the distal end thereof before this step. In other embodiments, an opening is first made in the artificial body wall using another instrument. In other embodiments, the distal end of the trocar 14800 is forced through the artificial body wall, generating an opening in the process.

The trocar 14800 is then converted into the fixation configuration illustrated in FIG. 14B by sliding the bolster 14840 down the cannula body 14812, and over the lip 14852 onto the enlarged section 14852. In the illustrated configuration, the artificial body wall is captured and compressed between the flange 14830 of the retainer and the bolster 14840. The lip 14852 locks the bolster 14840 in place, preventing it from moving proximally, thereby fixing or locking the trocar 14800 to the artificial body wall.

In the fixation configuration, the trocar 14800 fixed relative to a local portion of the artificial body wall to which it is engaged. As discussed above, however, embodiments of artificial body walls exhibit high elongations. Accordingly, the trocar 14800 is translatable and/or pivotable relative to an original position and orientation by deforming the artificial body wall.

In embodiments using an obturator 13910, the obturator is withdrawn. The trocar 14800 serves as an access port for one or more instruments during a surgical procedure.

If desired, the trocar 14800 is removed from the artificial body wall, for example, by first disengaging the bolster 14840 from the locking component 14850, then pulling the retainer 14830 from the artificial body wall. In some embodiments, the trocar 14800 and artificial body wall are not disengaged and are disposed of as a unit. In some embodiments, the bolster 14840 is not disengagable from the locking component 14850.

FIG. 15 is a side view of another embodiment of a retention trocar 15000, which is generally similar to the embodiment illustrated in FIGS. 14A and 14B and described above. The trocar 15000 comprises an elongate, tubular cannula 15810 comprising a proximal end, a distal end, and a cannula body 15812; a seal assembly 15820 coupled to the proximal end of the cannula 15810; a retainer 15830 disposed at the distal end of the cannula 15810; a bolster 14840 through which the cannula body 15812 extends; and a locking component 15850 disposed on the cannula body proximal of the retainer 15830.

In the illustrated embodiment, the locking component 15850 comprises an enlarged section 15854 on which are disposed screw threads 15852. The bolster 15840 comprises matching threads. Consequently, the bolster 15840 is threadably engagable to the locking component 15850. The threading also permits adjusting the relative positions of the bolster 15840 and a flange 15832 of the retainer in the fixation configuration of the trocar 15800, thereby permitting fixation to an artificial body wall with a non-uniform thickness and/or to artificial body walls of different thicknesses.

Figures 16A, 16B:
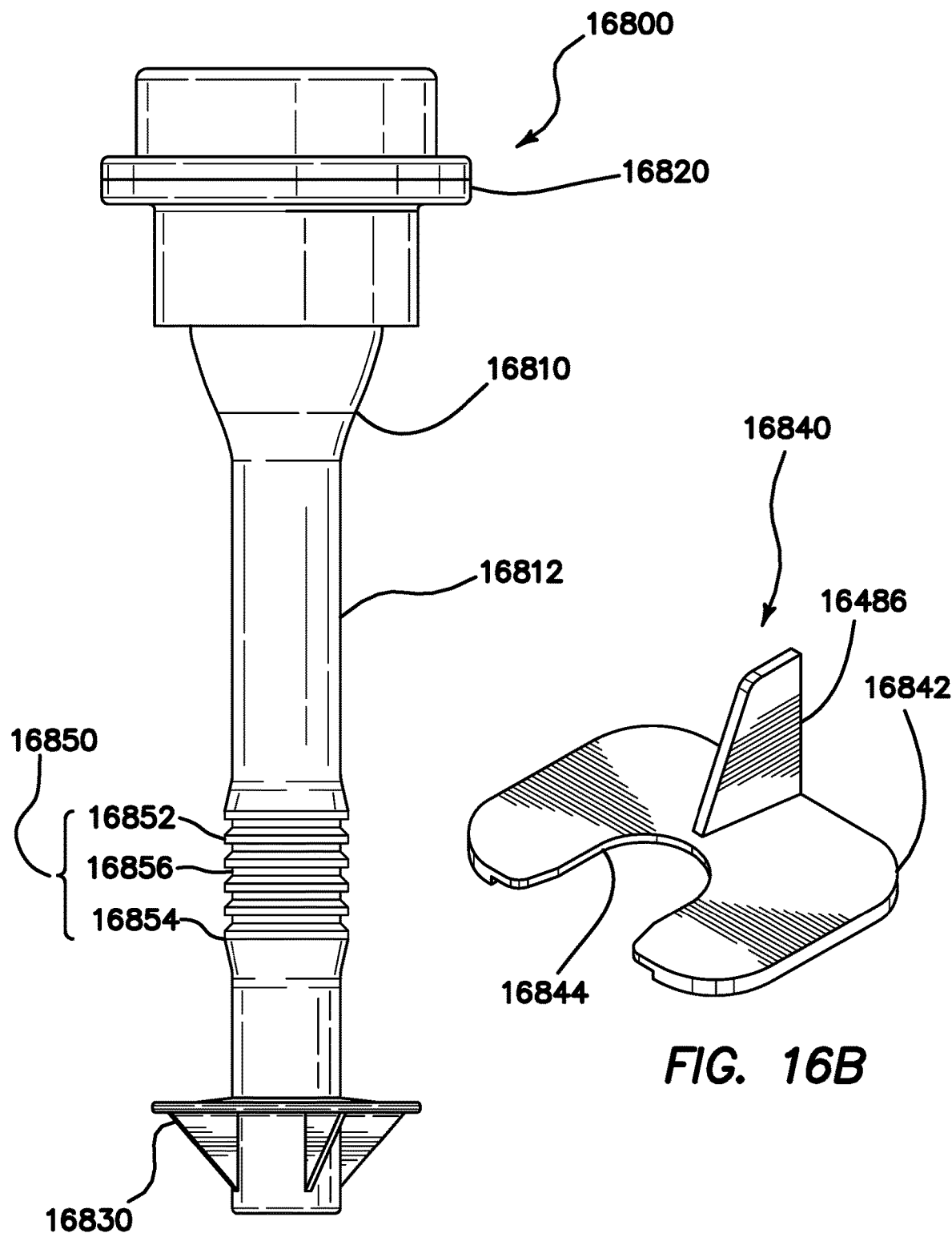
FIG. 16A is a side view of another embodiment of a trocar comprising a fixation cannula.
FIG. 16B is a perspective view of an embodiment of a bolster suitable for use with the trocar illustrated in FIG. 16A.

FIG. 16A is a side view of another embodiment of a trocar 16800. FIG. 16B is a perspective view of an embodiment of a bolster 16840 usable with the trocar 16800. The combination of the trocar 16800 and bolster 16840 are generally similar to the embodiments of trocars illustrated in FIGS. 14A, 14B, and 15. The trocar 16800 comprises an elongate, tubular fixation cannula 16810 comprising a proximal end, a distal end, and a cannula body 16812; a seal assembly 16820 coupled to the proximal end of the cannula 16810; a retainer 16830 disposed at the distal end of the cannula 16810; and a locking component 16850 disposed on the cannula body proximal of the retainer 16830.

In the illustrated embodiment, the locking component 16850 comprises an enlarged section 16854 comprising a plurality of annular rings 16852 extending radially from the cannula body 16812, which define a plurality of annular slots 16856. In the illustrated embodiment, a proximal edge of each ring 16856 is beveled; however, some embodiments do not comprise a beveled edge.

FIG. 16B illustrates an embodiment of a bolster 16840 in the form of a clip comprising a flattened body 16842 comprising a cut-out 16844 comprising a semicircular portion. The cut-out 16844 is dimensioned to engage the slots 16856. A thickness of the body 16842 at the cut-out 16844 is also dimensioned to engage the slots 16856. The bolster 16840 comprises a grip 16846 extending vertically from the body 16842, which provides a user grip for installing and/or adjusting the bolster 16840. In other embodiments, the cut-out 16844 has another shape, for example, polygonal, rectangular, a portion of a hexagon, and the like.

In use, the retainer 16830 of the trocar is inserted through an artificial body wall as discussed above, and fixed therein by engaging the bolster 16840 in a slot 16856 providing a desired fixation force. The degree of fixation is adjustable by selecting a different slot.

In some embodiments, the bolster cut-out 16844 engages a plurality of slots, thereby providing additional stability in the fixation configuration. Other embodiments comprise a bolster through with the cannula body 16812 extends, similar to the embodiments discussed above. In some of these embodiments, the locking component 16850 serves as a ratchet. The bolster comprises one or more pawls, which are optionally disengagable, thereby enhancing adjustability.

Figures 17A, 17B:
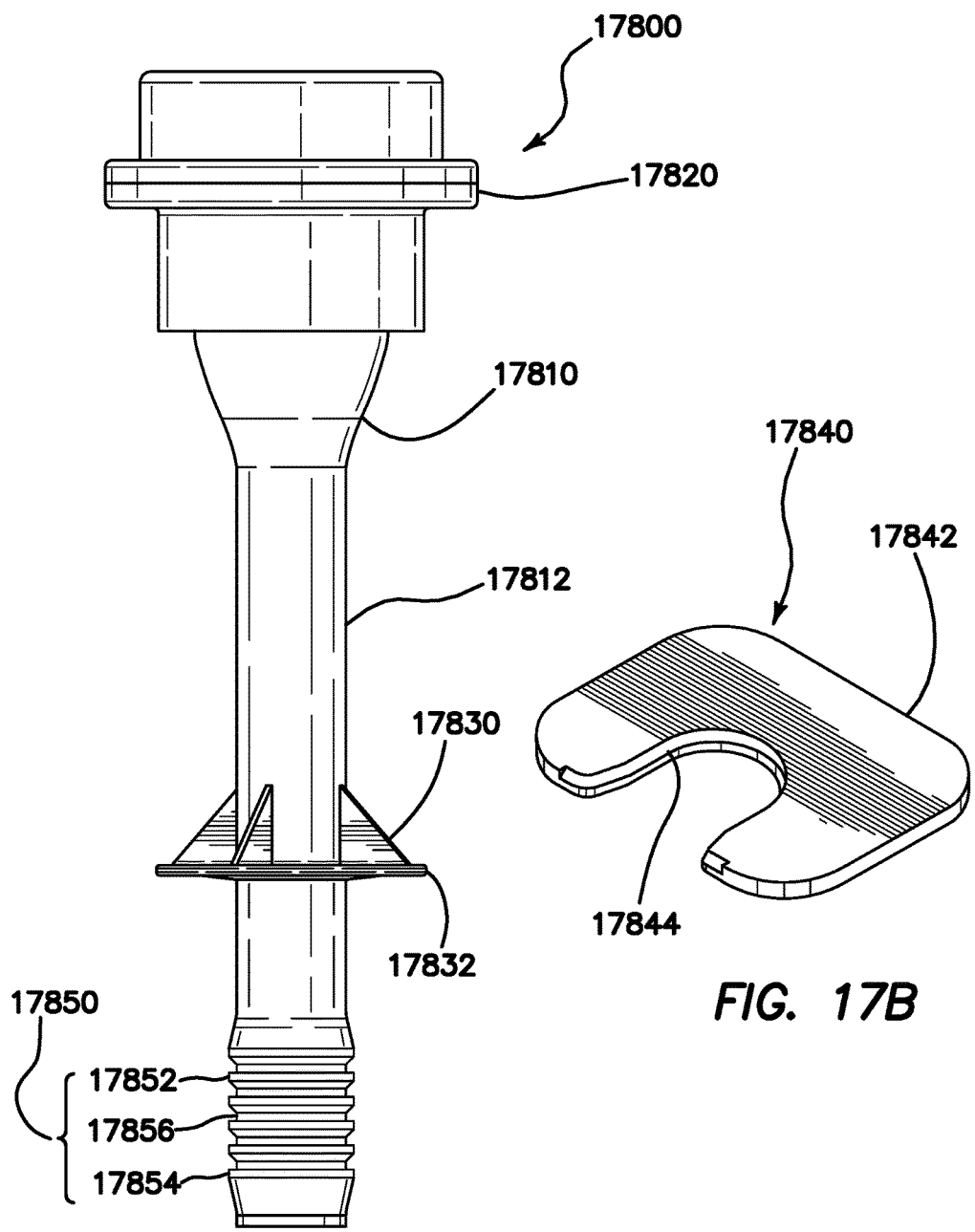
FIG. 17A is a side view of another embodiment of a trocar comprising a fixation cannula.
FIG. 17B is a perspective view of an embodiment of a bolster suitable for use with the trocar illustrated in FIG. 17A.

FIG. 17A illustrates a side view of an embodiment of a trocar 17800 comprising a fixation cannula and FIG. 17B is a perspective view of an embodiment of a bolster. The embodiments illustrated in FIGS. 17A and 17B are generally similar to the embodiments of trocars illustrated in FIGS. 14A-16B and described above.

The trocar 17800 comprises an elongate, tubular fixation cannula 17810 comprising a proximal end, a distal end, and a cannula body 17812; a seal assembly 17820 coupled to the proximal end of the cannula 17810; a retainer 17830 disposed on the cannula body 17812; and a locking component 17850 disposed at the distal end of the cannula 17810. The illustrated embodiment of the trocar 17800 is similar to the embodiment illustrated in FIG. 16A with the positions of the retainer 17830 and the locking component 17850 reversed. In the illustrated embodiment, a flange 17832 of the retainer faces distally.

The locking component 17850 comprises an enlarged section 17854 comprising a plurality of annular rings 17852 extending radially from the cannula body 17812, which define a plurality of annular slots 17856.

FIG. 17B illustrates an embodiment of a bolster 17840 in the form of a clip comprising a flattened body 17842 comprising a cut-out 17844 comprising a semicircular portion. The cut-out 17844 is dimensioned to engage slots 17856 in the locking component. A thickness of the body 17842 at the cut-out 17844 is also dimensioned to engage the slots 17856. The illustrated embodiment of the bolster does not comprise a grip; however, other embodiments comprise a grip.

In some embodiments for using the embodiment of the trocar 17800, the cannula 17810 is fixed to an artificial body wall before the artificial body wall is coupled to a patient's body. For example, in some embodiments, one or more trocars 17800 are fixed on a gel pad 10530 (FIG. 10A) of a gel cap 10500 before the gel cap 10500 is coupled to a retractor 6100, 7100 (FIGS. 6A-F).

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical access system adapted for performing laparoscopic surgical procedures at a natural orifice, the system comprising:
    an outer ring, wherein the outer ring is configured to be disposed proximate the natural orifice of a patient and substantially surrounds the natural orifice;
    a tubular body having a proximal end, a distal end, and a longitudinal axis, wherein the tubular body has a length and diameter adapted to accommodate an anatomy of the natural orifice, wherein the tubular body defines a generally cylindrical passage large enough to accommodate at least two laparoscopic instruments there through to access a body cavity at the distal end of the tubular body, wherein the tubular body further comprises at least one perforation that is adapted to be cut or torn, and wherein the at least one perforation is cut or torn to vary the length of the tubular body or to incorporate openings or windows into the tubular body, wherein the openings or windows provide additional access into the body cavity for the at least two laparoscopic instrument, and wherein the additional access include access into the body cavity different from the distal end of the tubular body or access into the body cavity previously obscured by the tubular body; and
    a funnel segment extending between and coupling the outer ring and the proximal end of the tubular body, wherein the funnel segment provides a diametric reduction between a large diameter of the outer ring and a smaller diameter of the tubular body, and wherein the funnel segment is sized to fit within the natural orifice with minimal distention of the natural orifice.

2. The surgical access system of claim 1, wherein the tubular body comprises a substantially flexible material.

3. The surgical access system of claim 1, wherein the tubular body comprises a polycarbonate.

4. The surgical access system of claim 1, wherein the tubular body is sufficiently large such that the at least two laparoscopic instruments positioned within the tubular body can be translated or pivoted relative to one another.

5. The surgical access system of claim 1, wherein the tubular body comprises one or more coatings.

6. The surgical access system of claim 5, wherein the one or more coatings comprise an anti-microbial coating.

7. The surgical access system of claim 1 further comprising a cap, cover, or lid, wherein the cap, cover, or lid is removably coupled to the outer ring of the surgical access device to provide a seal.

8. The surgical access system of claim 7, wherein the cap, cover, or lid comprises a gel adapted to receive the at least two laparoscopic instruments via direct insertion through the gel, and wherein the gel creates an instrument seal with the at least two laparoscopic instruments inserted through the gel.

9. The surgical access system of claim 8, wherein the cap, cover, or lid further comprise one or more trocars inserted through the gel that are adapted to receive the at least two laparoscopic instruments.

10. A method of using a surgical access system adapted for performing laparoscopic surgical procedures at a natural orifice, the method comprising:
    disposing the outer ring of a surgical access system proximate to the natural orifice of a patient and substantially surrounding the natural orifice;
    inserting the funnel segment and tubular body through the natural orifice, wherein the funnel segment extends between and couples the outer ring and a proximal end of the tubular body, wherein the funnel segment provides a diametric reduction between a large diameter of the outer ring and a smaller diameter of the tubular body, and wherein the funnel segment is sized to fit within the natural orifice with minimal distention of the natural orifice;
    positioning the tubular body with respect to the natural orifice thereby providing access to a body cavity past the natural orifice, wherein the tubular body has the proximal end, a distal end, and a longitudinal axis, wherein the tubular body has a length and diameter adapted to accommodate an anatomy of the natural orifice, wherein the tubular body defines a generally cylindrical passage large enough to accommodate at least two laparoscopic instruments there through to access a body cavity at the distal end of the tubular body, and wherein the tubular body further comprises at least one perforation that is adapted to be cut or torn; and cutting or tearing the at least one perforation of the tubular body to vary the length of the tubular body based on the natural orifice and the body cavity.

11. The method of claim 10 further comprising maneuvering the at least two laparoscopic instruments through the outer ring, the funnel segment, and the tubular body of the surgical access system to access the body cavity.

12. The method of claim 10, wherein the cutting or tearing the at least one perforation of the tubular body further creates cut-out portions or windows with the tubular body that provide additional access to the body cavity for the at least two laparoscopic instruments, and wherein the additional access include access into the body cavity different from the distal end of the tubular body or access into the body cavity previously obscured by the tubular body.

13. The method of claim 12, further comprising maneuvering the at least two laparoscopic instruments through the outer ring, the funnel segment, the tubular body and one of the cut-out portions or windows of the surgical access system to access the body cavity.

* * * * *